(12) United States Patent
Ionescu-Zanetti et al.

(10) Patent No.: US 8,293,524 B2
(45) Date of Patent: Oct. 23, 2012

(54) METHODS AND APPARATUS FOR THE MANIPULATION OF PARTICLE SUSPENSIONS AND TESTING THEREOF

(75) Inventors: Cristian Ionescu-Zanetti, Berkeley, CA (US); Michelle Khine, San Francisco, CA (US); Michael Schwartz, San Francisco, CA (US); Andrew Blatz, San Mateo, CA (US)

(73) Assignee: Fluxion Biosciences Inc., San Francisco, CA (US)

( * ) Notice: Subject to any disclaimer, the term of this patent is extended or adjusted under 35 U.S.C. 154(b) by 980 days.

(21) Appl. No.: 11/690,831

(22) Filed: Mar. 25, 2007

(65) Prior Publication Data

US 2007/0243523 A1    Oct. 18, 2007

Related U.S. Application Data

(60) Provisional application No. 60/744,034, filed on Mar. 31, 2006, provisional application No. 60/868,864, filed on Dec. 6, 2006, provisional application No. 60/870,842, filed on Dec. 19, 2006.

(51) Int. Cl.
*C12M 1/34* (2006.01)
*C12M 3/00* (2006.01)

(52) U.S. Cl. ............... 435/297.2; 435/287.1; 435/287.3; 435/395; 435/287.2

(58) Field of Classification Search ............... 435/287.1, 435/288.5, 305.2, 286.2, 287.3, 297.1, 297.2, 435/287.2, 395; 422/82.01
See application file for complete search history.

(56) References Cited

U.S. PATENT DOCUMENTS

| | | | |
|---|---|---|---|
| 5,744,366 | A | 4/1998 | Kricka |
| 5,842,787 | A | 12/1998 | Kopf-sill et al. |
| 5,885,470 | A | 3/1999 | Parce et al. |
| 5,942,443 | A | 8/1999 | Parce et al. |
| 6,068,752 | A | 5/2000 | Dubrow et al. |
| 6,153,073 | A | 11/2000 | Dubrow et al. |
| 6,238,538 | B1 | 5/2001 | Parce et al. |
| 6,251,343 | B1 | 6/2001 | Dubrow et al. |
| 6,274,337 | B1 | 8/2001 | Parce et al. |
| 6,315,940 | B1 | 11/2001 | Nisch et al. |
| 6,403,348 | B1 | 6/2002 | Rubinsky et al. |
| 6,413,782 | B1 | 7/2002 | Parce et al. |

(Continued)

FOREIGN PATENT DOCUMENTS

EP    0708331    4/1996

(Continued)

OTHER PUBLICATIONS

Abidor, et al. 246-Electric breakdown of bilayer lipid membranes. I. The main experimental facts and their qualitative discussion. Bioelectrochem. Bioenerg. 1979; 6:37-52.

(Continued)

*Primary Examiner* — Michael Marcheschi
*Assistant Examiner* — Shanta G Doe
(74) *Attorney, Agent, or Firm* — Dorsey & Whitney LLP

(57) ABSTRACT

Apparatus and methods are provided for analysis of individual particles in a microfluidic device. The methods involve the immobilization of an array of particles in suspension and the application of experimental compounds. Such methods can also include electrophysiology studies including patch clamp recording, electroporation, or both in the same microfluidic device. The apparatus provided includes a microfluidic device coupled to a multi-well structure and an interface for controlling the flow of media within the microchannel device.

34 Claims, 47 Drawing Sheets

U.S. PATENT DOCUMENTS

| | | |
|---|---|---|
| 6,429,025 B1 | 8/2002 | Parce et al. |
| 6,432,630 B1 | 8/2002 | Blankenstein |
| 6,437,551 B1 | 8/2002 | Krulevitch et al. |
| 6,454,945 B1 | 9/2002 | Weigl et al. |
| 6,479,299 B1 | 11/2002 | Parce et al. |
| 6,540,895 B1 | 4/2003 | Spence et al. |
| 6,562,604 B2 | 5/2003 | Rubinsky et al. |
| 6,589,729 B2 | 7/2003 | Chan et al. |
| 6,592,821 B1 | 7/2003 | Wada et al. |
| 6,632,619 B1 | 10/2003 | Harrison et al. |
| 6,653,089 B2 | 11/2003 | Takayama et al. |
| 6,686,184 B1 | 2/2004 | Anderson et al. |
| 6,686,193 B2 | 2/2004 | Maher et al. |
| 6,699,697 B2 | 3/2004 | Klemic et al. |
| 6,742,661 B1 | 6/2004 | Schulte et al. |
| 6,759,191 B2 | 7/2004 | Farinas et al. |
| 6,770,434 B2 | 8/2004 | Shvets et al. |
| 6,776,896 B1 | 8/2004 | Osipchuk |
| 6,899,800 B2 | 5/2005 | Osipchuk et al. |
| 6,900,021 B1 | 5/2005 | Harrison et al. |
| 6,927,049 B2 | 8/2005 | Rubinsky et al. |
| 6,932,893 B2 | 8/2005 | Bech et al. |
| 6,936,462 B1 | 8/2005 | Owen et al. |
| 6,969,604 B1 | 11/2005 | Yakovenko |
| 6,979,553 B2 | 12/2005 | Farinas et al. |
| 6,989,089 B2 | 1/2006 | Nisch et al. |
| 7,013,739 B2 | 3/2006 | Schroeder et al. |
| 7,018,819 B2 | 3/2006 | Orwar et al. |
| 7,067,263 B2 | 6/2006 | Parce et al. |
| 7,112,433 B2 | 9/2006 | Tyvoll et al. |
| 7,122,301 B2 | 10/2006 | Shvets et al. |
| 7,176,016 B2 | 2/2007 | Maher et al. |
| 7,214,298 B2 | 5/2007 | Spence et al. |
| 7,221,455 B2 | 5/2007 | Chediak et al. |
| 7,241,565 B2 | 7/2007 | Bullen et al. |
| 7,244,349 B2 | 7/2007 | Vogel et al. |
| 7,288,785 B2 | 10/2007 | Vestergaard et al. |
| 7,312,085 B2 | 12/2007 | Chou et al. |
| 7,358,077 B2 | 4/2008 | Zimmermann et al. |
| 7,361,500 B2 | 4/2008 | Stett et al. |
| 7,390,650 B2 | 6/2008 | Karlsson et al. |
| 7,452,726 B2 | 11/2008 | Chou et al. |
| 7,470,518 B2 | 12/2008 | Chiu et al. |
| 7,563,614 B2 | 7/2009 | Orwar et al. |
| 8,058,056 B2* | 11/2011 | Lee et al. .................... 435/288.5 |
| 2002/0039783 A1 | 4/2002 | McMillan |
| 2002/0045566 A1 | 4/2002 | Gribkoff et al. |
| 2002/0064841 A1 | 5/2002 | Klemic et al. |
| 2002/0125139 A1* | 9/2002 | Chow et al. .................... 204/601 |
| 2002/0164777 A1 | 11/2002 | Kelly et al. |
| 2002/0182627 A1* | 12/2002 | Wang et al. .................... 435/6 |
| 2002/0182642 A1 | 12/2002 | Orwar et al. |
| 2002/0195337 A1 | 12/2002 | Osipchuk et al. |
| 2003/0022268 A1 | 1/2003 | Lepple-Wienhues |
| 2003/0065452 A1 | 4/2003 | Hickman |
| 2003/0121778 A1 | 7/2003 | Dodgson et al. |
| 2003/0129581 A1 | 7/2003 | Owen et al. |
| 2003/0138767 A1 | 7/2003 | Bullen et al. |
| 2003/0139336 A1 | 7/2003 | Norwood et al. |
| 2003/0143720 A1 | 7/2003 | Hickman |
| 2003/0153067 A1 | 8/2003 | Stett et al. |
| 2003/0153076 A1 | 8/2003 | Villeponteau et al. |
| 2003/0159999 A1 | 8/2003 | Oakey |
| 2003/0180965 A1 | 9/2003 | Yobas et al. |
| 2003/0199050 A1 | 10/2003 | Mangano et al. |
| 2003/0219884 A1 | 11/2003 | Lison et al. |
| 2003/0224531 A1* | 12/2003 | Brennen et al. ................ 436/180 |
| 2004/0005696 A1 | 1/2004 | Vesterguard et al. |
| 2004/0005901 A1 | 1/2004 | Ala-Luukko |
| 2004/0028567 A1* | 2/2004 | Parce et al. .................... 422/100 |
| 2004/0106126 A1 | 6/2004 | Fendler |
| 2004/0146849 A1 | 7/2004 | Huang et al. |
| 2004/0202994 A1* | 10/2004 | Timperman .................... 435/4 |
| 2004/0229349 A1 | 11/2004 | Daridon |
| 2005/0009004 A1 | 1/2005 | Xu et al. |
| 2005/0026283 A1 | 2/2005 | Ormar et al. |
| 2005/0058990 A1 | 3/2005 | Guia et al. |
| 2005/0070018 A1 | 3/2005 | Johnson et al. |
| 2005/0118723 A1 | 6/2005 | Padmanabhan et al. |
| 2005/0129581 A1 | 6/2005 | McBride et al. |
| 2005/0170510 A1 | 8/2005 | Huang et al. |
| 2005/0196746 A1 | 9/2005 | Xu et al. |
| 2005/0224351 A1 | 10/2005 | Ungar et al. |
| 2005/0266478 A1 | 12/2005 | Huang et al. |
| 2005/0277125 A1* | 12/2005 | Benn et al. .................... 435/6 |
| 2006/0003310 A1 | 1/2006 | Klauke et al. |
| 2006/0006067 A1 | 1/2006 | Unger |
| 2006/0194255 A1 | 8/2006 | Finkel |
| 2006/0234298 A1 | 10/2006 | Chiu et al. |
| 2007/0155016 A1 | 7/2007 | Lee et al. |
| 2007/0243523 A1 | 10/2007 | Ionescu-Zanetti et al. |
| 2009/0209029 A1 | 8/2009 | Guia et al. |

FOREIGN PATENT DOCUMENTS

| | | |
|---|---|---|
| EP | 0708331 A1 | 4/1996 |
| EP | 1448771 B1 | 8/2004 |
| EP | 1597576 A1 | 11/2005 |
| GB | 2371626 | 7/2002 |
| WO | WO 98/52691 A1 | 11/1998 |
| WO | WO 99/55827 A1 | 11/1999 |
| WO | WO 2005/089253 A2 | 9/2005 |
| WO | WO 2007/008609 A2 | 1/2007 |
| WO | WO 2005/089253 A3 | 3/2007 |
| WO | WO 2007/024701 A2 | 3/2007 |
| WO | WO 2008/072029 A2 | 6/2008 |

OTHER PUBLICATIONS

Akinlaja, et al. The Breakdown of Cell Membranes by Electrical and Mechanical Stress. Biophys J., 1998, 75, 247-254.

Burnett, et al. Fluorescence imaging of electrically stimulated cells. J Biomol Screen, Dec. 2003;8(6):660-7.

Dove, A. Screening for content—the evolution of high throughput. Nature. Biotechnology. 2003; 21:859-864.

Entzeroth, M. Emerging trends in high-throughput screening. Current Opinion in Pharmacology. 2003; 3:522-529.

Fertig, et al. Activity of single ion channel proteins detected with a planar microstructure, Applied Physics Letters. 2002; 81:4865-4867.

Fertig, et al. Stable integration of isolated cell membrane patches in a nanomachined aperture. Appl. Phys. Lett. 2000; 77:1218-1220.

Gill., et al. Flux assays in high throughput screening of ion channels in drug discovery. Assay Drug Dev Technol. Oct. 2003;1(5):709-17.

Haas, et al. Single-cell electroporatien for gene transfer in vivo. Neuron. Mar. 2001;29(3):583-91.

Immke, et al, Ion-Ion interactions at the selectivity filter. Evidence from K (+)-dependent modulation of tetraethylammonium efficacy in Kv2.1 potassium channels. J Gen Physiol. Apr. 2000;115(4):509-18.

International search report dated Dec. 21, 2005 for PCT Application No. US2005/08349.

International search report dated Dec. 7, 2007 for PCT Application No. US2007/65001.

Lin, et al, Structure formation at the interface of liquid/liquid bilayer in electric field. Macromolecules. 2002; 35:3971-3976.

Lundqvist, et al. Altering the biochemical state of individual cultured cells and organelles with ultramicroelectrodes. Proc Natl Acad Sci U S A. Sep. 1, 1998;95(18):10356-60.

Needham, et al. Electro-mechanical permeabilization of lipid vesicles. Role of membrane tension and compressibility. Biophys J. May 1989;55(5):1001-9.

Neubert, H. J. Patch clamping moves to chips. Anal Chem Sep. 1, 2004;76(17):327A-330A.

Neumann, et al. Gene transfer into mouse lyoma cells by electroporation in high electric fields. EMBO J. 1982;1(7):841-5.

Neumann, et al. Mechanism of electroporative dye uptake by mouse B cells. Biophys J. Jan. 1998;74(1):98-108.

Sakmann, et al. Patch clamp techniques for studying ionic channels in excitable membranes. Annu Rev Physiol. 1984;46:455-72.

Stett, et al. CYTOCENTERING: a novel technique enabling automated cell-by-cell patch clamping with the CYTOPATCH chip. Receptors Channels. 2003;9(1):59-66.

Stett, et al. Patch-clamping of primary cardiac cells with micro-openings in polyimide films. Med Biol Eng Comput. Mar. 2003;41(2):233-40.

Thorsen, et al. Microfluidic large-scale integration. Science. Oct. 18, 2002;298(5593):580-4.

Trapani, et al. Control of ion channel expression for patch clamp recordings using an inducible expression system in mammalian cell lines. Bmc Neuroscience. 2003;4:15.

Weaver, et al. Decreased bilayer stability due to transmembrane potentials. Phys Lett. 1981:86A:57-59.

Weaver, et al. Theory of electroporation. In "Electroporation and Electrofusion in Cell Biology" (Neumann,E., Sowers, A., Jordan C, eds.). Plenum Press. New York. 1989; 111-126.

Weaver, J. C. Electroporation: a general phenomenon for manipulating cells and tissues. J Cell Biochem. Apr. 1993;51(4):426-35.

Wood, et al. Patch clamping by numbers. Drug Discov Today. May 15, 2004;9(10):434-41.

Matthews and Judy, "Characterization of a micromachined planar patch clamp for cellular electrophysiology", 1st International IEEE EMBS Neural Engineering Conference, 2003, Capri, Italy (Mar. 20-22).

Orwar et al., "System and method for obtaining and maintaining high-resistance seals in patch clamp recording," U.S. Appl. No. 60/404,886, filed Aug. 21, 2002.

Extended supplementary European search report dated Mar. 24, 2010 for European Patent Application No. 07759449.7.

Li, et al. Transport, Manipulation, and Reaction of Biological Cells on-chip using electrokinetic effects. Anal Chem. 1997; 69:1564-1568.

Stell, et al. The Flow Thru Chip: A 3-D Biochip platform microarray Biochip Technology. Eaton Publishing, Mass. 2000; pp. 87-117.

Amaxa Biosystems. Available at: http://www.amaxa.com/96-wellnucleofection.html. Accessed Jan. 8, 2008.

AMBION. The RNA Company, siPorter TM 96 Electroporation Chamber. Available at: http://www.ambion.com/catalog/CatNum.php?13500. Accessed Jan. 8, 2008.

Asmild, et al. Upscaling and Automation of Electrophysiology: Toward High Throughput Screening in Ion Channel Drug Discovery. Receptors and Channels. 2003; 9:49-58.

Ausubel, et al. (Eds.) Current Protocols in Molecular Biology. vols. I, II, and III, 1997.

Ausubel, et al. (Eds.), Short Protocols in Molecular Biology: A Compendium of Methods from Current Protocols in Molecular Biology. 5th Ed. John Wiley & Sons, Inc. 2002.

Axoporator 800A. Molecular Devices. Available at: http://moleculardevices.com/pages/instruments/en_axoporator800.html. Accessed on Aug. 13, 2008.

Batzer, et al. Enhanced evolutionary PCR using oligonucleotides with inosine at the 3'-terminus. Nucleic Acids Res. 1991; 19(18):5081.

Bennett, et al. Trends in ion channel drug discovery: advances in screening technologies. Trends Biotechnol. 2003; 21(12):563-9.

BIO-RAD.COM. Available at : http://www.bio-rad.com/B2B/BioRad/product/br_category.jsp?BV_SessionID=@@@@1456209995.1143592729@@@@&BV_EngineID=cccdaddhgikgikhcfngcfkmdhkkdf11.0&loggedIn=false&lang=English&divName=Corporate&country=HQ&categoryPath=/Catalogs/Life%20Science%20Research/Gene%20Transfer/Products/Electroporation/Gene%20Pulser%20Xcell%20System&catLevel=6&catOID=-28754&isPA=false&serviceLevel=Lit+Request. Accessed Jan. 7, 2008.

Bonetta. Flow cytometry smaller and better. Nature Methods. 2005; 2(10): 785.

Brown, et al. Improvements to parallel plate flow chambers to reduce reagent and cellular requirements. BMC Immunol. 2001; 2: 9.

BTX Molecular Delivery Systems. Available at: http://www.btxonline.com/products/advancedtransfection/default.asp. Accessed Jan. 7, 2008.

Chang, et al. Guide to Electroporation and Electrofusion. Academic Press. 1992.

Denyer, et al., HTS approaches to voltage-gated ion channel drug discovery. Drug Discovery Today. 1998; 3(7):323-332.

Fertig, et al., Whole Cell Patch Clamp Recording Performed on a Planar Glass Chip. Biophysical Journal. 2002; 82:3056-3062.

Huang, et al. Microfabricated electroporation chip for single cell membrane permeabilization. Sensors and Actuators A. 2001; 89:242-249.

Innis, et al. (Eds.) PCR Protocols: A Guide to Methods and Applications. Elsevier Science & Technology Books. 1990.

Ionescu-Zanetti, et al., Mammalian Electrophysiology on a Mircrofluidic Platform. PNAS. 2005; 102(26):9112-9117.

Khine, et al., A Single Cell Electroporation Chip. Lab Chip. 2005; 5:38-43.

Klemic, et al. Micromolded PDMS planar electrode allows patch clamp electrical recordings from cells. Biosensors and Bioelectronics 2002; 17:597-604.

Lehnert, et al. Realization of hollow SIO2 micronozzles for electrical measurements on living cells. Applied Physics Letters. 2002; 81:5063-5065.

Lu, et al. Microfluidic shear devices for quantitative analysis of cell adhesion. Anal Chem. 2004; 76(18): 5257-64.

Nolkrantz, et al. Electroporation of Single Cells and Tissues with an Electrolyte-filled Capillary. Analytical Chemistry. 2001; 73:4469-4477.

Rae, et al. Single-cell electroporation. Pflugers Arch. 2002; 443(4):664-70.

Schroeder, et al. IonWorks (TM) HT: A new high-throughput electrophysiology measurement platform. Journal of Biomolecular Screening. 2003; 8(1):50-64.

Seo, et al. Integrated Multiple Patch-Clamp Array Chip via Lateral Cell Trapping Junctions. Applied Physics Letters. 2004; 84(11):1973-1975.

Southhan, et al. Ion Channels—New Opportunities for an Established Target Class. Drug Discovery World. 2005; 18-23.

Stett, et al., Patch-clamping of primary cardiac cells with microopenings in polymide films. Medical & Biological Engineering & Computing. 2003; 41:233-240.

Tsong. Electroporation of cell membranes. Biophysical Journal. 1991; 60: 297-306.

Xu, et al. Ion-channel assay technologies: quo vadis? Drug Discovery Today. 2001; 6:1278-1287.

U.S. Appl. No. 60/710,305, entitled "Cell Handling, Electroporation and Electrofusion in Microfluidic System," filed Aug. 21, 2005.

Ionescu-Zanetti, et al., U.S. Appl. No. 60/744,034, entitled "Methods and Apparatus for Intracellular Delivery and Electrophysiology," filed Mar. 31, 2006.

Ionescu-Zanetti, et al., U.S. Appl. No. 60/868,864, entitled "Methods and Apparatus for a Stop-Flow Imaging Cytometer," filed Dec. 6, 2006.

Amendment in Response to Non-Final Office Action mailed Jun. 25, 2009 for U.S. Appl. No. 11/466,104.

Non-Final Office Action mailed Feb. 25, 2010 for U.S. Appl. No. 11/690,831.

Non-Final Office Action mailed Jul. 23, 2010 for U.S. Appl. No. 11/466,104.

Non-Final Office Action mailed Jun. 25, 2009 in U.S. Appl. No. 11/466,104.

Non-Final Requirement for Restriction/Election mailed Nov. 17, 2008 for U.S. Appl. No. 11/466,104.

Office Action mailed Jun. 21, 2010 in connection with U.S. Appl. No. 11/690,831.

Response to Non-Final Requirement for Restriction/Election mailed Nov. 17, 2008 for U.S. Appl. No. 11/466,104.

Response to Non-Final Office Action mailed Jun. 21, 2010 for U.S. Appl. No. 11/690,831.

Response to Non-Final Restriction Requirement received Feb. 25, 2010 for U.S. Appl. No. 11/690,831.

Examination Report dated Jan. 17, 2011 for related EP Application No. 07759449.7.

* cited by examiner

FIG. 3A (side view)
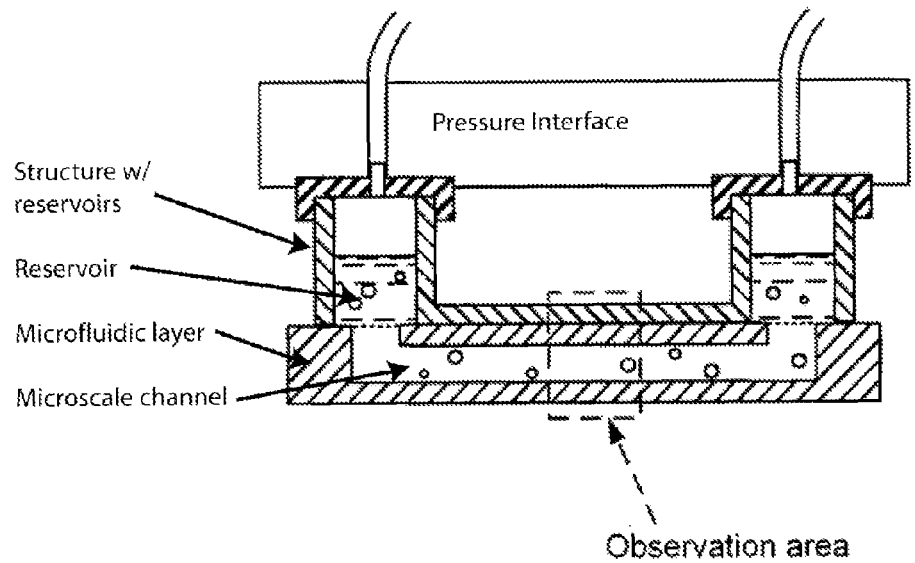
FIG. 3B (top view)
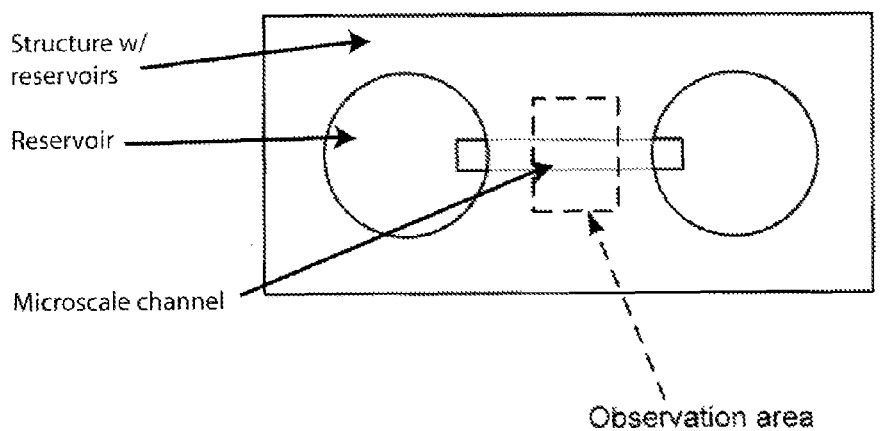

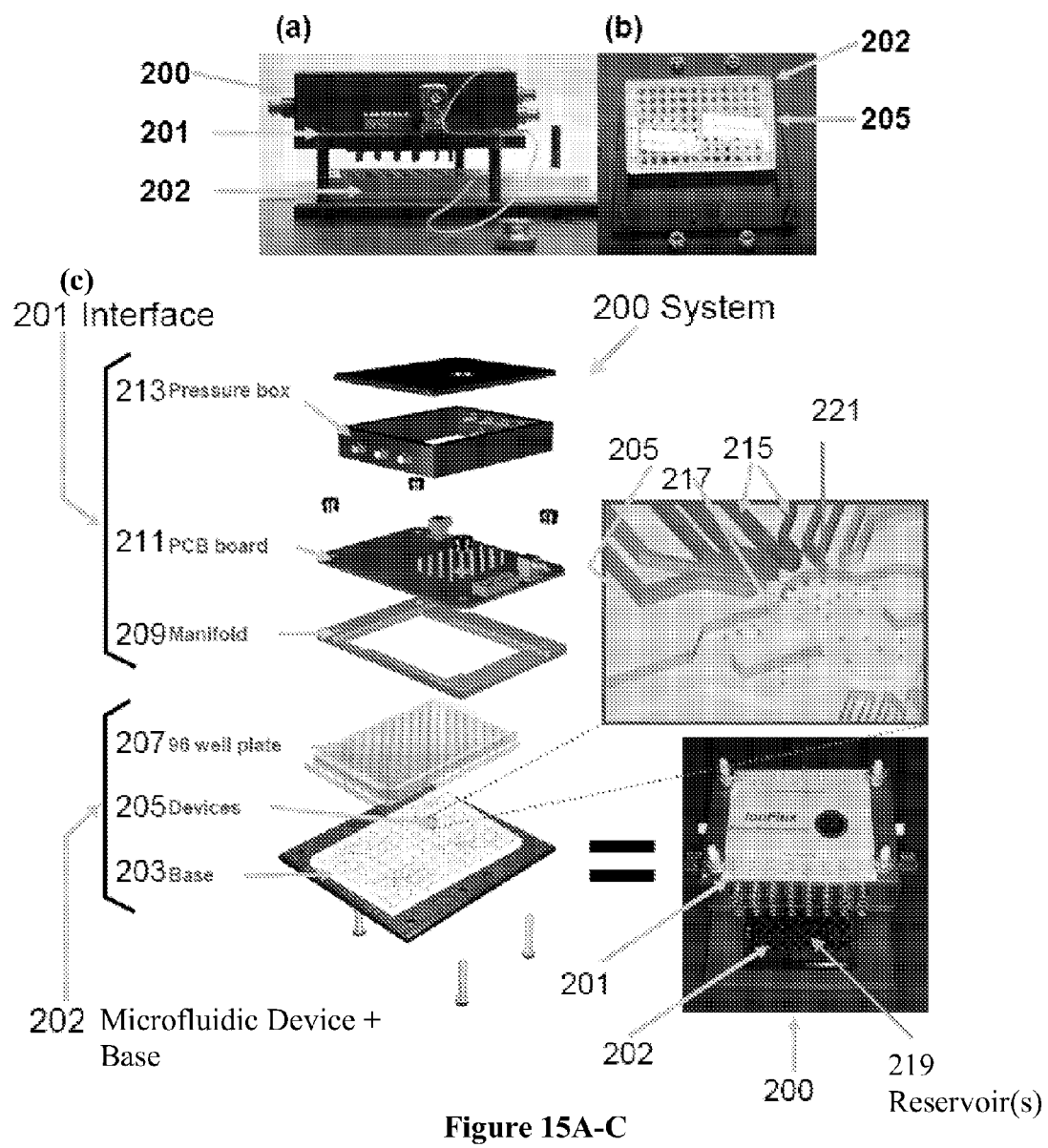
Figure 15A-C

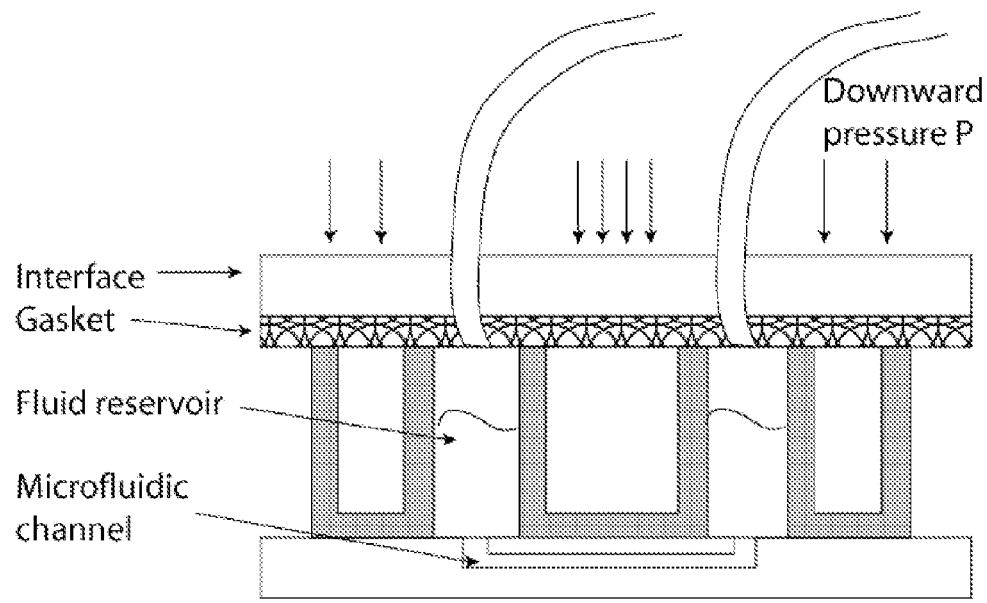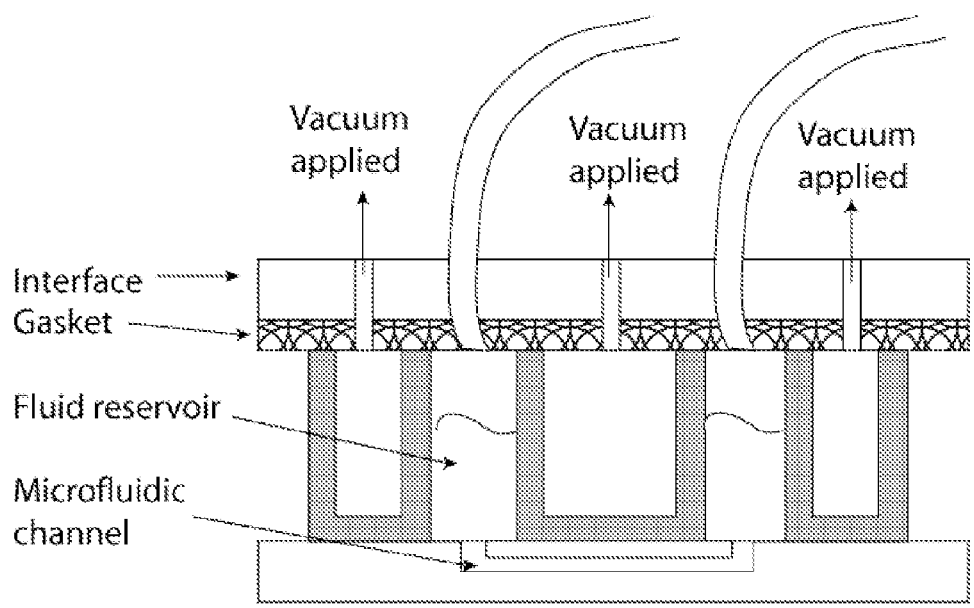
Figure 15D

Figure 45
A
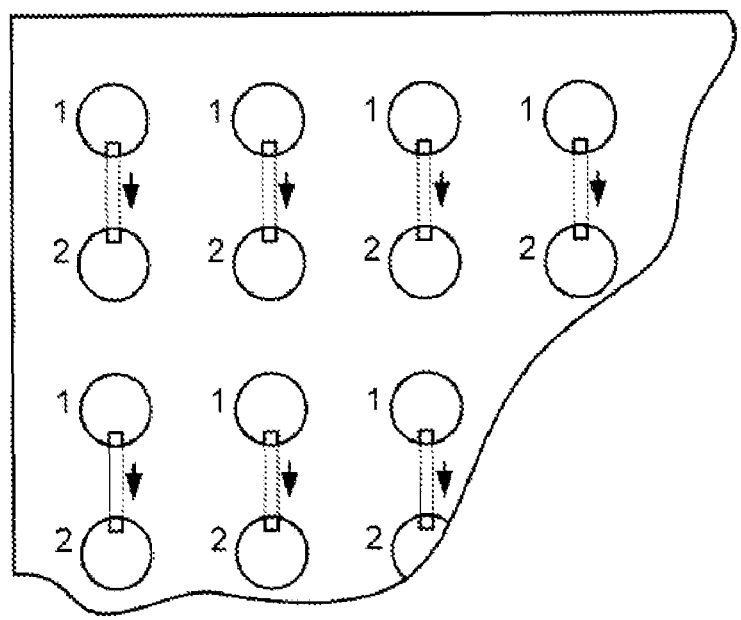
B
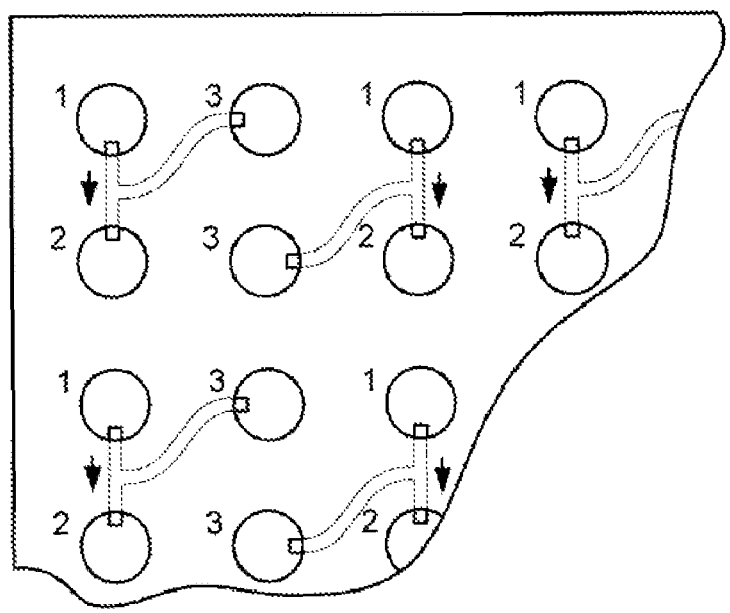

Figure 46
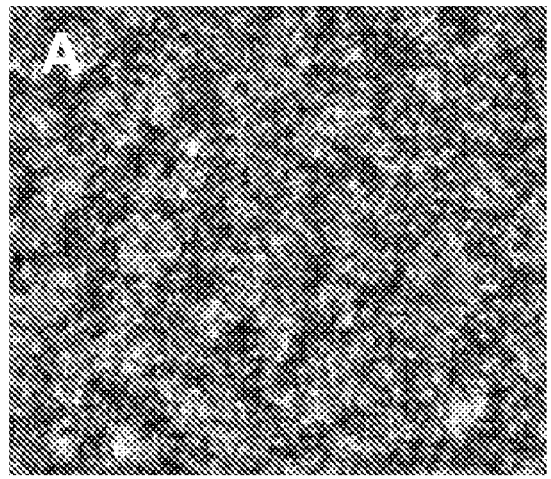
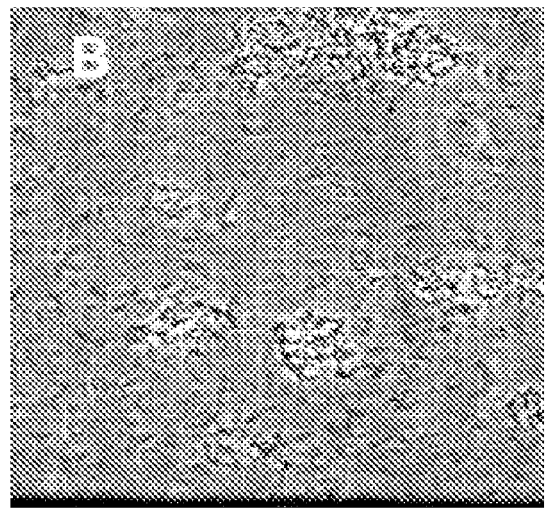
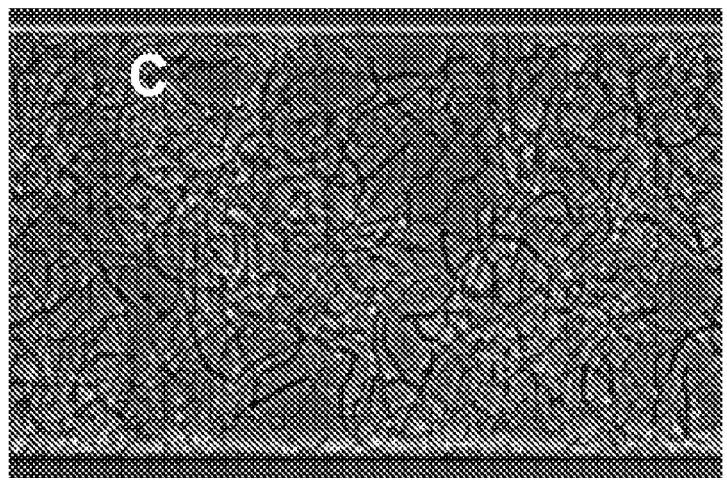

METHODS AND APPARATUS FOR THE MANIPULATION OF PARTICLE SUSPENSIONS AND TESTING THEREOF

CROSS-REFERENCE

This application claims the benefit of U.S. Provisional Application No. 60/744,034, filed Mar. 31, 2006, U.S. Provisional Application No. 60/868,864 filed Dec. 6, 2006, and U.S. Provisional Application No. 60/870,842 filed Dec. 19, 2006; these applications are incorporated herein by reference.

STATEMENT AS TO FEDERALLY SPONSORED RESEARCH

Funds used to support some of the studies disclosed herein were provided by grant number 1 R43 GM075509-01 awarded by the National Institutes of Health from the National Institute for General Medical Sciences. The Government may have certain rights in the invention.

BACKGROUND OF THE INVENTION

The fields of flow cytometry, ion-channel electrophysiology, single cell electroporation, controlled shear force in vivo-simulating cell culture and numerous related biotechnology approaches stand to benefit from advances in the design of microfluidic devices for manipulation of cells and attendant apparatus.

Flow cytometry is a widely used technique for the counting and classification of single cells (Cottingham 2005). Because of its high throughput (1000s of cells/s) and reliability, it has become the most widely used method for cell population identification. It has far reaching applications, from pharma and academic research to drug cell based screening and cell line QC. In the diagnostic market it is used primarily for the quantification of blood cell content, and used to monitor RBC counts as well as counts for all of the major WBC types (blood panel).

While flow cytometry was originally based on electrical resistance changes in a flow capillary, almost all modern flow cytometers are now based on a laser for excitation and PMT for the detection of fluorescent signals from each cell, thus providing data which is multiplexed with straight cell count data. This allows for the identification and counting of a number of different cell types (through the use of fluorescent probes), as well as establishing relations between the fluorescence intensities recorded.

A key drawback of this technique is the loss of sub cellular information. Cell morphological parameters, as well as localization of fluorescent signals w/in the cell and the correlation between various stains are all lost in a process which simply integrates the fluorescence intensity over the whole cell and outputs one number per cell.

Until recently, this type of information has only been accessible through the use of Image Scanning Cytometry, basically a microscope on an XYZ stage that scans a thin cavity filled w/cellular suspension. This is an automation of the manual hemocytometer. This technique is significantly slower as compared to flow cytometry, and requires automatic focus and due to movement of the substrate in the XY plane. An additional drawback of this technique is the inability to sort cells.

Recently introduced imaging flow cytometers aim to combine the speed and ease of use of flow cytometry with the high information content of Image Scanning Cytometry (Bonetta 2005). The instrument images cells as they flow by at high velocity in a single file. The requirement of assembling in-flight images of single cells requires a great deal of custom technical development, which translates in a relatively high price for such devices (approx. $300 k for ImageStream 100) and relegates their use to core labs and pharmaceutical companies.

Ion channels are functional units of all living systems and fulfill a number of roles, from fast signal transmission in the nervous system to regulation of biochemical pathways. In turn, a number of disorders have been linked to ion channel malfunction. Ion channels are implicated in mental disorders such as Alzheimer's and epilepsy, as well as heart disease, diabetes and neuromuscular disease [Shaffer]. Consequently, these transmembrane proteins are attractive drug targets and constitute about 20-30% of new drug development campaigns [Southhan].

The electrophysiology recording technique, termed patch clamp, has emerged as the gold standard in the study of ion channel function. It is based on the ability to perform recordings of transmembrane currents through a specific ion channel type. Traditionally, patch clamp recording is accomplished with a micromanipulator-positioned glass pipette under a microscope [Sackmann]. This technique was perfected in 1981-'83 by Nether and Sackmann through the achievement of high resistance seals between the glass pipette tip and the cell membrane. The basic setup is illustrated in FIG. 5A. Current that passes through the ion channels in either the membrane patch or the whole cell membrane is recorded at different bias voltages.

In June 2005, the FDA mandated that all drugs must be tested against the potassium (K) ion channel hERG, whose unpredicted adverse modulation by several blockbuster drugs has been implicated in long-QT syndrome and subsequent sudden death by heart malfunction [Denyer]. It has been estimated that approximately 25-40% of all lead compounds show hERG activity in vitro [Bennett].

The gold standard assay for hERG safety screening is the patch clamp: the cell is voltage clamped in whole-cell configuration (using a glass pipette) while the test compounds are introduced extracellularly. The response of the cell to the test compounds is evident from the current response of the cell when the compounds have reached the ion channel's binding site which, in the case of hERG, is on the interior portion of the cell (see FIG. 6). FIG. 6 shows an outward rectifying potassium channel. As indicated in the diagram, the candidate hERG blocker (e.g., a compound to be tested) binds at the intracellular side of the molecule. Source: Enal Razvi [Southhan]. The problem with this approach is that the compounds are notoriously slow to diffuse through the membrane to reach this binding site (t>20 minutes). In addition, multiple compound concentrations need to be applied sequentially to the same patched cell in order to provide consistent measurement. Consequently, hERG measurements often fail due to the lack of long term stability for the high resistance seal between the glass pipette and the cell (seals often degrade in t<20 minutes).

Despite constant improvement of the traditional patch clamp technique, it remains laborious, requiring pipettes to be placed in the cell vicinity by a skillful operator using a micromanipulator under a microscope. Consequently, the patch clamp technique has been difficult to use in drug development, where high-throughput automated measurements are required. An automated patch clamp setup for high-throughput measurements using disposable devices would eliminate the prohibitive time investment of the traditional patch clamp, while maintaining its advantages over indirect measurements of ion channel behavior. The first approach to automated patch consisted of an array of robotically operated patch clamp pipettes (Axon, Inc.), to be used with large cells (*Xenopus* oocytes). The most serious drawbacks of this approach its inability to work with mammalian cell lines as well as the complexity of the manipulation system, while savings in terms of reagent use are minimal. A microfabricated patch clamp approach, if perfected, would solve both these problems. Currently available automated electrophysiology devices are employed by large organizations at large capital expense (greater than $400,000 per instrument) as well as a large cost per data point (about $10 per cell trap). They also retain important limitations in the area of optical observation and compound perfusion.

RNA interference is arguably the most powerful second-generation functional genomics technology currently available [Klemic]. Its high robustness, specificity, and efficacy in silencing targeted genes suggests its potential to father the development of a whole new class of drugs for an incredibly broad range of diseases. Before this can happen, however, significant challenges with respect to short interfering RNA (siRNA) delivery and targeting must be overcome.

One way to traverse the cell membrane and access the cell's interior is by temporarily increasing the permeability of the cell membrane. This can be accomplished via electroporation, a technique which uses high electric fields to induce structural rearrangements of the cell membrane. Pores result when the transmembrane potential exceeds the dielectric breakdown voltage of the membrane (0.2-1.5V) [Weaver]. Polar substances otherwise impermeant to the plasma membrane (such as dyes, drugs, DNA, proteins, peptides, and amino acids) can thus be introduced into the cell.

In the early 1980s, Eberhard Neumann et al. demonstrated the feasibility of electroporation for delivering DNA to a population of mammalian cells [Lundqvist]. Since then, this method of bulk electroporation has become a standard technique routinely used to simultaneously transfect millions of cells in culture. Most commercially available electroporation systems still use Neumann's approach without too much variation. Bulk electroporation requires very high voltages (kVolts) and has little control over the permeabilization of individual cells, resulting in suboptimal parameters. Moreover, because different cell types require different electric field parameters to electroporate, the system has to be calibrated to determine appropriate pulse conditions a priori without any real-time control. Reversible electroporation, in which the pores can reseal, is therefore difficult [Chang, D. C.]. As a result, most commercial systems focus on improving buffer solutions to improve cell viability. Examples of commercial electroporation platforms include the Gene Pulser Xcell™ Eukaryotic System (Bio-Rad Laboratories), BTX® HT 96 Well Electroporation System (BTX® Molecular Delivery Systems), Nucleofector™ 96-well Shuffle System (Amaxa Biosystems), and Axoporator 800A (Molecular Devices).

Single cell electroporation obviates many of the challenges associated with bulk electroporation but is less common. Lundqvist et al first demonstrated single cell electroporation using carbon fiber microelectrodes in 1998 [Lundqvist]. To induce electroporation, they placed microelectrodes 2-5 microns away from adherent progenitor cells. Other single cell electroporation techniques developed since include: electrolyte-filled capillaries [Nolkrantz (Electroporation)], micropipettes [Hass, Rae], and chips [Huang]. For successful single cell electroporation, the cell must either be isolated or the electric field well focused to target a particular cell [Nolkrantz (Functional Screening)]. Currently single cell electroporation is performed using laborious manual setups.

Contact adhesion between cells and surfaces, both inside and outside organisms, are central to a large number of biological phenomena. Some examples are blood clotting, tissue repair, immune and inflammatory response, bacterial infections, and cancer progression. A widely used method to quantify cell adhesion has been the application of a range of shear forces in flow chambers. The same methods are used to determine the cellular response to shear stress through mechanotransduction pathways.

The bulk of this type of research is currently performed using macroscopic laminar flow chambers. Current practice suffers from limited throughput, cumbersome apparatus assembly, experiment failure (i.e. by bubble introduction), and a limited range of applicable shear forces.

Thus, there remains a considerable need for alternative designs of microfluidic devices for manipulation of cells to support flow cytometry, cell ion-channel electrophysiology, single cell electroporation, controlled shear force in vivo-simulating cell culture and related technologies. The present invention satisfies these needs and provides related advantages as well.

SUMMARY OF THE INVENTION

Aspects of the invention may include one or more of the following advantageous features: The system described herein can be useful to investigate dynamic processes at the cellular systems level and further to leverage related findings to engineer therapeutically useful cells for molecular medicine. Such cell uses can include but are not limited to applications to combat infectious diseases, neurodegenerative diseases, genetic disorders, and cancer.

In general, in one aspect, the invention features a microfluidic device for analysis of individual particles in a suspension including a substrate with one or more microfluidic channels adapted for individual addressability of particles, said substrate coupled to a plate with an array of apertures. In one embodiment the plate is a multi-well microplate. In another embodiment the multi-well microplate is selected from the group consisting of a 24-well, 96-well, 384-well, and 1536-well microplate.

In one embodiment the substrate is selected from the group consisting of a polymer, glass and quartz. In one embodiment the polymer is polydimethylsiloxane (PDMS). In another embodiment the substrate is integrated into the microplate such the microfluidic channels face upward. In a further embodiment the substrate that microchannels are molded into is continuous without punched holes.

In one embodiment the microfluidic device further includes an intermediate substrate disposed between the substrate and the plate.

In another embodiment the particles are selected from the group consisting of beads, cells, bacterial cells, vesicles, Oocytes, collection of cells and embryos.

In general, in another aspect, the invention features a microfluidic system for the analysis of particle suspensions including a microfluidic layer comprising at least one microscale flow channel adapted to contain particle suspensions, and an observation area for imaging the particle suspensions; a structure comprising one or more reservoirs in fluid communication with the microfluidic layer, wherein the reservoirs of the structure are in fluid communication with the microflow and main flow channels of the microfluidic layer; an interface detachably connectable to the microfluidic layer, wherein the interface controls fluid flow and pressure to one or more reservoir, thereby controlling pressure delivery to each microscale flow channel.

In one embodiment the system further includes a gasket between the interface and the device wherein the gasket is adapted to support a pressure seal between the interface and the device. In a related embodiment the pressure seal between the interface and the device includes a mechanical pressure seal between the gasket and the device. In one embodiment the pressure seal between the interface and the device is a negative pressure seal between the gasket and the device.

In a particular embodiment the interface includes manual regulators to regulate the pressure delivery to the one or more reservoirs. In one embodiment the manual regulators include manual toggle valves. In a related embodiment the interface includes electronically controlled regulators to regulate the pressure delivery to the one or more reservoirs. In another embodiment the electronically controlled regulators include electronically controlled valves.

Implementations of the invention can also include one or more of the following features. In one embodiment the particles are selected from the group consisting of beads, cells, bacterial cells, vesicles, Oocytes, collection of cells and embryos. In another embodiment the main flow channel is substantially 100-2000 um in width and substantially 5-200 um in depth. In a further embodiment a plurality of microscale channels are in fluid communication with one reservoir of the structure. In another embodiment the main flow channel is connected to a plurality of reservoirs of the structure, and wherein microscale channels terminate in the reservoirs.

In general, in another aspect, the invention features a method for analyzing a plurality of individual particles in suspension including repeatedly introducing pluralities of particles into a microfluidic chamber via flow; repeatedly acquiring images of said particles; and analyzing said images to characterize the particle population.

Implementations of the invention can include one or more of the following features. In one embodiment the microfluidic chamber comprises a section of a microfluidic channel. In another embodiment the flow comprises an adjustable flow velocity and wherein the flow velocity is adjustable between a flow velocity greater than 100 um/s and a flow velocity less than 1 um/s. In a further embodiment image acquisition occurs during periods of flow velocity less than 1 um/s. In a related embodiment analyzing images includes creating a set of individual particle images. In one embodiment characterizing the particle population includes determining a particle population characteristic selected from the group consisting of total particle counts, particle density in suspension, and particle size distribution. In another embodiment the particles are selected from the group consisting of beads, cells, bacteria, vesicles, Oocytes, and embryos.

In one embodiment characterizing the particle population includes characterization selected from the group consisting of determining fluorescent intensity, determining fluorescent marker distribution within the body or periphery of the particle, and classification of particles based on fluorescent intensity and/or fluorescent marker distribution and/or fluorescence lifetime. In a related embodiment images are acquired utilizing a method selected from the group consisting of optical microscopy, fluorescence microscopy, phase contrast microscopy, and confocal microscopy. In one embodiment analysis of the images comprises automatic particle recognition and storage of individual particle images.

In general, in another aspect, the invention features a system for performing particle imaging, counting, characterization, and classification including a microfluidic device containing a chamber adapted and arranged for simultaneous imaging of a plurality of particles; a flow actuation system in fluid communication with the microfluidic device that can introduce a population of particles into the chamber; an image acquisition system positionable for imaging the chamber; and an image analysis system in communication with the image acquisition system.

Implementations of the invention can include one or more of the following features. In one embodiment particles are selected from the group consisting of beads, cells, bacterial cells, vesicles, oocytes, collection of cells and embryos. In another embodiment the chamber includes a section of a microfluidic channel. In a further embodiment the microfluidic channel includes part of a microfluidic network. In one embodiment the microfluidic channel includes an inlet and outlet each in fluid communication with one or more reservoir. In another embodiment the reservoirs are disposed in a standard well plate format, selected from the group consisting of 6-well, 24-well, 96-well, 384-well, and 1536-well plates.

In a particular embodiment the flow actuation system is adapted to provide a flow velocity adjustable between a flow velocity greater than 100 um/s and a flow velocity less than 1 um/s. In one embodiment the flow actuation system includes a pressure application apparatus. In another embodiment the microfluidic channel includes an inlet and an outlet and the pressure application apparatus is adapted to apply a differential pressure to the inlet and outlet of the microfluidic channel. In one embodiment the flow actuation system includes an electrokinetic flow apparatus.

In one embodiment the image acquisition system includes a microscope and a CCD camera. In a related embodiment the image acquisition system includes a microscope objective and a CCD camera, mounted in an enclosure. In a particular embodiment the enclosure includes a microscope chassis.

In a further embodiment the image analysis system includes a microprocessor and a software application. In a related embodiment the software application is adapted to identify individual particles among the imaged particles. In another embodiment the software application is adapted to measure the size and morphological parameters of identified particles. In yet another embodiment the software application is adapted to classify imaged particles based on the size and morphological parameters of imaged particles. In one embodiment the software application is adapted to measure a fluorescence intensity and fluorescent distribution inside a perimeter of each identified particle. In another embodiment the software application is adapted to classify imaged particles based on the measurement of fluorescence intensity and fluorescent distribution inside the perimeter of each identified particle.

In general, in another aspect, the invention features a microfluidic system for sorting individual particles based on optical observation including a microfluidic layer with at least two microscale channels intersecting with a main flow channel; a multi-well structure in fluid communication with the microfluidic layer, with the wells of said multi-well structure in fluid communication with the channels of the microfluidic layer; an interface which is removably coupled to the microfluidic device which controls the flow of fluid in the microfluidic channels and can apply a positive or negative pressure to each of the wells of the multi-well plate, thereby applying positive or negative pressure to the microscale channels in the microfluidic layer; and a control system in optical and fluid communication with the microfluidic layer, and adapted for particle identification and selective pressure application depending on observed particle position.

Implementations of the invention can include one or more of the following features. In one embodiment the particle is selected from the group consisting of cells, bacteria, vesicles, oocytes, and embryos and particle identification includes an observation selected from the group consisting of observed particle size, particle morphology and particle surface marker.

In general, in another aspect, the invention features a microfluidic system including a structure including a plurality of open reservoirs; and a substrate including microfluidic channels on one side, said substrate coupled to the structure with the channel side facing the substrate, wherein the microfluidic channels are in alignment with the open reservoirs of the structure such that the reservoirs of the structure are in fluidic communication with the microfluidic channels. In one implementation the substrate includes one or more main flow channel, a plurality of trapping channels and a detection zone for viewing cells microscopically, wherein one or more reservoir is in fluid communication with one or more trapping channel, and wherein each trapping channel is in fluid communication with one or more main flow channel, and wherein the detection zone is adapted for viewing cells using an upright microscope or an inverted microscope.

In general, in another aspect, the invention features a microfluidic system for trapping individual particles in an array for analysis including a microfluidic layer including an array, at least two microscale channels and a main flow channel wherein the microscale channels intersect with the main flow channel and wherein the array is adapted to trap individual particles; a structure including a plurality of reservoirs coupled to the microfluidic layer, wherein the reservoirs of the structure are in fluid communication with the microscale and main flow channels of the microfluidic layer; and an interface detachably connectable to the microfluidic layer, wherein the interface controls fluid flow, and pressure to one or more reservoir, thereby controlling pressure delivery to each microscale channel.

Implementations of the invention can include one or more of the following features. In one embodiment the microscale channels are adapted to trap particles selected from the group consisting of cells, vesicles and oocytes. In another embodiment the microscale channels are substantially 0.5-10 um in width and substantially 0.5-10 um in depth. In yet another embodiment the main flow channel is substantially 100-200 um in width and substantially 20-100 um in depth. In one embodiment a plurality of microscale channels are in fluid communication with one reservoir of the structure. In another embodiment the main flow channel is connected to a plurality of reservoirs of the structure, wherein microscale channels terminate in the reservoirs.

In general, in another aspect, the invention features a method for analyzing a plurality of individual particles including disposing a suspension of particles into one or more reservoir of a microfluidic device including one or more reservoir and a plurality of intersecting channels in fluid communication with the one or more reservoir; immobilizing a plurality of individual particles at one or more junction of the plurality of intersecting channels; perfusing one or more compounds across the particles; and analyzing the plurality of individual particles.

Implementations of the invention can include one or more of the following features. In one embodiment the microfluidic device further includes a substantially planar substrate positioned below a plane of the bottom of the reservoirs, wherein the one or more junction of intersecting channels and the immobilized particles are disposed within the planar substrate.

In one embodiment the particles are selected from the group consisting of cells, vesicles and oocytes. In another embodiment analyzing includes measuring properties from one or more of the immobilized individual particles. In yet another embodiment compounds are perfused inside the intersecting channels. In a further embodiment the intersecting channels are part of a microfluidic network of channels.

In another embodiment analyzing comprises taking measurements selected from the group consisting of whole cell voltage clamping, whole cell current clamping, and patch clamping. In a related embodiment analyzing includes taking measurements selected from the group consisting of optical microscopy, fluorescence microscopy, phase contrast microscopy, and confocal microscopy. In another embodiment the compounds are selected from the group consisting of biomolecules, small molecules, proteins, enzymes, genetic material, biomarkers, and dyes.

In general, in another aspect, the invention features a system for single particle analysis the system comprising a microfluidic device comprising one or more reservoirs and adapted for holding and manipulating particles and compounds; and an interface adapted to provide pressure to the one or more reservoirs, wherein the interface is detachably coupled to the microfluidic device. In one implementation the microfluidic device is integrated into a microplate format selected from the group consisting of a 24-well, 96-well, 384-well, and 1536-well microplate, or a section thereof.

In general, in one aspect, the invention features a system for conducting patch clamp measurements on an array of immobilized particles, wherein the distance between immobilized particles is substantially below 0.1 mm. In one implementation the particles are selected from the group consisting of cells, vesicles and oocytes. In one embodiment the particles are cells. In a related embodiment a plurality of the cells can be simultaneously observed microscopically. In another embodiment the system further includes one or more compound streams in fluid communication with the immobilized cells wherein a plurality of the cells are exposed to the same compound stream.

In general, in another aspect, the invention features a system for conducting patch clamp experiments including a microfluidic device with at least two intersecting channels and a detection zone; an interface detachably coupled to the microfluidic device, wherein the interface is adapted for moving material within the microfluidic device; and an electrode array electrically and fluidically in communication with the microfluidic device.

Implementations of the invention can include one or more of the following features. In one implementation the microfluidic device is integrated into a structure including a plurality of reservoirs. In one embodiment the structure includes a microplate, the microfluidic device is integrated into the microplate and the microplate is selected from the group consisting of a 24-well, 96-well, 384-well, and a 1536-well microplate. In another embodiment the interface is coupled to a section of the microfluidic device.

In one embodiment the detection zone includes a region of the microfluidic device adapted for immobilizing a plurality of cells. In another embodiment the detection zone includes a region of the microfluidic device that is optically accessible. In a further embodiment the detection zone includes a region of the microfluidic device that is optically accessible microscopically during patch clamp measurements.

In a particular embodiment the electrode array includes electrodes which extend into the reservoirs of the microfluidic device when the microfluidic device and interface are coupled. In a related embodiment the electrodes provide both electrical connection and connection to a pressure source. In one embodiment the electrodes are substantially cylindrical. In a related embodiment the substantially cylindrical electrodes include an end, wherein a section cut out of the end can extend into the reservoirs of the microfluidic device. In one embodiment the electrode array is adapted for electrophysiological analysis of plurality of cells. In a particular embodiment the electrophysiological analysis includes recording selected from the group consisting of whole-cell recording and patch clamp recording.

In one embodiment the interface is adapted to act as a shield for ambient electromagnetic waves. In another embodiment the interface is connectable to a patch clamp amplifier. In yet another embodiment the interface provides an aperture for optical access.

In general, in another aspect, the invention features a system for intracellular delivery including a microfluidic device with a plurality of intersecting channels and a detection zone; an interface detachably coupled to the microfluidic device, wherein the interface is adapted for moving material within the device, and an electrode array; a patch clamp amplifier in electrical communication with the electrode array; a logic device in communication with the interface and patch clamp amplifier; and a software control system in communication with the logic device and adapted to control the system for intracellular delivery.

Implementations of the invention can include one or more of the following features. In one embodiment the microfluidic device is integrated into a structure including a plurality of reservoirs. In another embodiment the microfluidic chip is integrated into a microplate and the microplate is selected from the group consisting of a 24-well, 96-well, 384-well, and a 1536-well microplate.

In one embodiment the detection zone includes a region of the microfluidic device adapted to immobilize a plurality of cells. In another embodiment the detection zone includes a region of the microfluidic device that is optically accessible. In yet another embodiment the detection zone includes a region of the microfluidic chip that is optically accessible microscopically.

In a further embodiment the electrode array includes electrodes which extend into the reservoirs of the microfluidic device when the microfluidic device and interface are coupled. In one embodiment the electrode arrays include substantially cylindrical electrodes. In a related embodiment the substantially cylindrical electrodes include an end, wherein a section cut out of the end can extend into the reservoirs of the microfluidic device when coupled to the interface. In another embodiment the electrode array is adapted to electroporate an array of individual cells. In yet another embodiment the electrode array includes a plurality of electrodes in electrical communication with an array of trapped cells on the microfluidic devices and one or more reference electrodes.

In one embodiment the patch clamp amplifier is adapted to apply a voltage across the electrode array. In another embodiment the software control system is adapted to measure currents through cell membranes, and can adjust an applied voltage as a function of the measured current. In a particular embodiment the software control system includes a feedback loop which is adapted to stop an increase in voltage application when electroporation is detected. In another embodiment the resealing of membranes is monitored over time by applying a test pulse.

In another embodiment the system further includes compounds which can be exchanged inside the intersecting channels. In one embodiment compounds can be exchanged inside both intersecting channels in a time span less than 100 ms.

In yet another embodiment the interface is adapted to act as a shield from ambient electromagnetic waves. In a related embodiment the interface is adapted to allow light to pass through to the microfluidic device. In one embodiment the interface is connectable to a patch clamp amplifier. In a particular embodiment the interface provides an aperture for optical access.

In general, in another aspect, the invention features a system for performing electroporation and electrophysiology measurements of cells on the same platform comprising a microfluidic device adapted to perform electroporation and electrophysiology measurements; a patch clamp amplifier in electrical communication with the microfluidic device; and a current measurement system in electrical communication with the microfluidic device. In one implementation both electroporation and electrophysiology measurements are achieved using the same patch clamp amplifier.

In general, in yet another aspect, the invention features a method of performing electroporation and electrophysiology measurements of cells on the same platform including providing a combined electroporation and electrophysiology measurement platform including a microfluidic device, a patch clamp amplifier and a current measurement system; electroporating cells disposed within the microfluidic device; interrogating the cells disposed within the microfluidic device, wherein interrogating the cells includes performing patch clamp measurements on the cells using the patch clamp amplifier and the current measurement system. In one implementation cells are first electroporated, then plated on the microfluidic device, and then interrogated by performing patch clamp measurements. In another implementation the microfluidic device further includes a structure having a plurality of reservoirs, and wherein after electroporation each cell is directed to a reservoir.

In general, in another aspect, the invention features a single cell electrophysiology and electroporation array system for intracellular compound delivery and analysis including a substrate; a main flow channel in said substrate adapted to hold cells in a fluidic medium; at least one lateral opening in a side of said main flow channel; at least one trapping channel operatively connected to said lateral opening; at least two electrical connections, one connected to said main flow channel and one connected to said trapping channel, such that an electric field can be focused where a cell contacts said lateral opening, and such that one or more characteristics of said cell can be detected; and wherein a cell in the main flow channel can be selectively immobilized at said lateral opening by negative pressure in the trapping channel. In one implementation the detected characteristic of a cell is an ion-flux activity. In a particular embodiment the ion-flux activity is hERG activity. In one embodiment the compound is a biomolecule. In a related embodiment the biomolecule is a nucleic acid. In a particular embodiment the nucleic acid is siRNA.

In general, in another aspect, the invention features a method for measuring the characteristics of particles in the presence of shear forces including dispensing a particle suspension into the wells of a microfluidic device; introducing said suspension into one or more microfluidic channels of the device; providing flow within one or more of the microfluidic channels; and measuring a characteristic of the particle suspension.

Implementations of the invention can include one or more of the following features. In one embodiment measuring a characteristic is made at a time selected from the group consisting of at least one of before, during or after the providing of flow. In another embodiment particles are selected from the group consisting of beads, cells, bacterial cells, vesicles, oocytes, collections of cells and embryos.

In one embodiment the microfluidic device includes a perforated plate containing wells irreversibly bonded to a microfluidic layer containing microscale channels. In a related embodiment the microfluidic channels include inlets and outlets and wherein the wells of the perforated plate are in fluid communication with the inlets and outlets. In another embodiment flow is provided by applying positive or negative pressure to an air-fluid interface in the wells of the microdevice. In yet another embodiment flow is provided by applying an electrokinetic force.

In another embodiment the microfluidic channels include a height dimension between 0.1-500 um and a width dimension between 1-2000 um. In one embodiment measurement of the particle characteristic includes acquiring images of the particle suspension before, during and after providing flow. In a related embodiment the images are acquired while the particles reside in a section of a microfluidic channel.

In a particular embodiment the measured characteristic of the particle suspension is selected from the group consisting of: measuring the adherence of particles to substrates during flow, measuring the adherence of flowing particles to static substrate-bound particles during flow, measuring the detachment of particles due to flow after an initial static attachment period, measuring the migration of particles during flow, and measuring the morphology of particles.

In general, in another aspect, the invention features a method for performing a shear force assay on cells including introducing a cell suspension in a microfluidic enclosure; allowing cells to attach to an internal surface of the enclosure; applying a shear force to cells by providing flow through the enclosure; and measuring one or more cellular response to the shear force. In one implementation the cell suspension includes at least one of the group consisting of mammalian cells, bacterial cells, oocytes, collection of cells and embryos. In another embodiment the cellular response is measured by acquiring images of the cells at a time selected from at least one of before, during, or after the providing flow. In yet another embodiment the cellular response is a measurable change selected from the group consisting of cell morphology, cell fluorescence and fluorescent distribution, and cell motility.

In general, in another aspect, the invention features a device for performing shear force experiments at multiple shear rates including a microfluidic layer wherein the microfluidic layer is irreversibly bonded to a plate including reservoirs; a plurality of microfluidic channels disposed within the microfluidic layer and comprising at least two different fluidic resistances; and an observation area including an optically viewable portion of the device in which the plurality of microfluidic channels exhibit different shear forces simultaneously.

In general, in another aspect, the invention features a method for performing multiple shear force experiments including introducing a particle suspension comprising particles into a number of branches of a branched microfluidic channel; applying a shear force to said particles by providing flow in the channel branches; and measuring one or more characteristic of said particles in response to the applied shear forces. In one implementation the particles are selected from the group consisting of beads, cells, bacterial cells, vesicles, oocytes, collection of cells and embryos. In one embodiment measurement of the particle characteristics is based on acquiring images of the particle suspension before, during and after providing flow. In related embodiment images are acquired while particles reside in a section of a microfluidic channel. In a particular embodiment the measured characteristic of the particle suspension is a measurable change selected from the group consisting of: measuring the adherence of particles to substrates during flow, measuring the adherence of flowing particles to static substrate-bound particles during flow, measuring the detachment of particles due to flow after an initial static attachment period, measuring the migration of particles during flow, and measuring the morphology of particles.

In general, in another aspect, the invention features a device for measuring the effects of shear forces on a plurality of different specimens including a plurality of microfluidic channels in fluidic communication with a one or more wells in a perforated plate, wherein the microfluidic channel is configured to provide substantially the same shear force in a section of each microfluidic channel.

In general, in yet another aspect, the invention features a method for measuring the effects of shear forces on a number of different specimens including dispensing a plurality of specimens into one or more wells of a microfluidic device; introducing the plurality of specimens into one or more microfluidic channels of the microfluidic device; applying substantially the same shear force to the specimens simultaneously by providing flow through the microfluidic channels; and measuring one or more characteristic of the specimens.

Implementations of the invention can include one or more of the following features. In one embodiment measuring a characteristic is made at a time selected from at least one of before, during or after the application of flow. In another embodiment the microfluidic device includes a perforated plate containing wells irreversibly bonded to a microfluidic layer including microscale channels. In another embodiment the specimens are particles selected from the group consisting of beads, cells, bacterial cells, vesicles, oocytes, collection of cells and embryos. In one embodiment the microfluidic channels include inlets and outlets and wherein the wells of the perforated plate are in fluid communication with the inlets and outlets.

In one embodiment flow is driven by applying a pressure or vacuum to the air-fluid interface in the wells of the microdevice. In a particular embodiment flow is driven by an electrokinetic force.

In another embodiment the microfluidic channels include a height dimension between 0.1-500 um and a width dimension between 1-2000 um. In yet another embodiment measurement of the particle characteristic includes acquiring images of the particle suspension before, during and after providing flow. In one embodiment the images are acquired while the particles reside in a section of a microfluidic channel. In yet another embodiment the measured characteristic of the particle suspension is selected from the group consisting of: measuring the adherence of particles to substrates during flow, measuring the adherence of flowing particles to static substrate-bound particles during flow, measuring the detachment of particles due to flow after an initial static attachment period, measuring the migration of particles during flow, and measuring the morphology of particles.

In general, in another aspect, the invention features a method for measuring the effects of compounds on particles under shear stress, comprising dispensing a suspension of particles comprising particles into one or more wells of a microfluidic device comprising a plurality of wells; dispensing one or more compounds into one or more wells of the microfluidic device; introducing the particles into microfluidic channels of the microfluidic device; applying shear forces to the particles by providing flow through the microfluidic channels; exposing the particles to compounds at a time selected from at least one of before, during or after the application of shear stress; and measuring a characteristic of the particles at a time selected from at least one of the group consisting of before, during or after the application of shear stress and compounds.

Implementations of the invention can include one or more of the following features. In one embodiment the microfluidic device includes of a perforated plate containing wells irreversibly bonded to a microfluidic layer containing microscale channels. In another embodiment the particles are selected from the group consisting of beads, cells, bacterial cells, vesicles, oocytes, collection of cells and embryos. In yet another embodiment the microfluidic channels include inlets and outlets and wherein the wells of the perforated plate are in fluid communication with the inlets and outlets.

In one embodiment flow is provided by applying positive or negative pressure to an air-fluid interface in the wells of the microdevice. In a related embodiment flow is provided by applying an electrokinetic force.

In yet another embodiment the microfluidic channels include a height dimension between 0.1-500 um and a width dimension between 1-2000 um.

In another embodiment measurement of the particle characteristic comprises acquiring images of the particle suspension before, during and after applying flow and at a time selected form at least one of the group consisting of: before, during or after exposure to compounds. In one embodiment the images are acquired while particles reside in a section of a microfluidic channel. In a particular embodiment the measured characteristic of the particle suspension is selected from the group consisting of: measuring the adherence of particles to substrates during flow, measuring the adherence of flowing particles to static substrate-bound particles during flow, measuring the detachment of particles due to flow after an initial static attachment period, measuring the migration of particles during flow, and measuring the morphology of particles.

In general, in another aspect, the invention features a system for performing shear force experiments on particles, including a microfluidic device including one or more microfluidic channel irreversibly attached to a plate comprising reservoirs; a flow actuation system in fluid communication with the microfluidic device and configured to introduce a population of particles into at least one of the microfluidic channels and apply shear stress to the particles; and a measurement system in optical communication with the microfluidic device for determining one or more characteristics of the population of particles.

Implementations of the invention can include one or more of the following features. In one embodiment particles are selected from the group consisting of beads, cells, bacterial cells, vesicles, oocytes, collection of cells and embryos. In another embodiment the one or more microfluidic channel is part of a microfluidic network. In a related embodiment the one or more microfluidic channels include an inlet and outlet, wherein the inlet and outlet are in fluid communication with the reservoirs. In one embodiment flow is provided by applying a differential pressure to the inlet and outlet of the microfluidic channel. In one other embodiment the reservoirs are disposed in the plate in a standard well plate format, selected from the group consisting of 6-well, 24-well, 96-well, 384-well, and 1536-well plates.

In one embodiment the flow actuation system includes a pressure application apparatus. In a related embodiment the flow actuation system includes an electrokinetic flow apparatus.

In another embodiment the measurement system includes an imaging acquisition system including a microscope and a CCD camera. In a particular embodiment the measurement system includes a microscope objective and a CCD camera, mounted in an enclosure. In one embodiment the enclosure is a microscope chassis.

In one embodiment the measurement system includes a microprocessor and a software application. In a particular embodiment the measurement system determines a characteristic of the population of particles including acquiring images of the population of particles before, during and after applying flow. In one embodiment the measured characteristic of the population of particles is selected from to the group consisting of: measuring the adherence of particles to substrates during flow, measuring the adherence of flowing particles to static substrate-bound particles during flow, measuring the detachment of particles due to flow after an initial static attachment period, measuring the migration of articles during flow, and measuring the morphology of particles.

As used herein and in the appended claims, the singular forms "a," "an," and "the" include plural reference unless the context clearly indicates otherwise.

Unless defined otherwise, all technical and scientific terms used herein have the same meaning as commonly understood to one of ordinary skill in the art to which the inventions described herein belong. Although any methods, devices, and materials similar or equivalent to those described herein can be used in the practice or testing of the inventions described herein, the preferred methods, devices and materials are now described.

Definitions

The term "biologically active molecule", "biologically active moiety" or "biologically active agent" when used herein means any substance which can affect any physical or biochemical properties of a biological organism, including but not limited to viruses, bacteria, fungi, plants, animals, and humans. In particular, as used herein, biologically active molecules include but are not limited to any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, dyes, lipids, nucleosides, oligonucleotides, cells, viruses, liposomes, microparticles and micelles. Classes of biologically active agents that are suitable for use with the methods and compositions described herein include, but are not limited to, antibiotics, fungicides, anti-viral agents, anti-inflammatory agents, anti-tumor agents, cardiovascular agents, anti-anxiety agents, hormones, growth factors, steroidal agents, and the like.

The term "nucleic acid" refers to deoxyribonucleotides, deoxyribonucleosides, ribonucleosides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

The term "microorganism" when used herein refers to bacteria, actinomycetales, cyanobacteria (unicellular algae), fungi, protozoa, animal cells or plant cells or virus.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues are a non-natural amino acid. As used herein, the terms encompass amino acid chains of any length, including full length proteins (i.e., antigens), wherein the amino acid residues are linked by covalent peptide bonds. In addition, proteins that contain multiple polypeptide chains that associate through covalent and/or non-covalent interactions are also encompassed by "protein," as used herein.

The term "individual" when used herein is not limited to a human being, but may also include other organisms including but not limited to mammals, plants, bacteria or cells derived from any of the above.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE FIGURES

A better understanding of the features and advantages of the present methods and compositions may be obtained by reference to the following detailed description that sets forth illustrative embodiments, in which the principles of our methods, compositions, devices and apparatuses are utilized, and the accompanying drawings of which:

FIG. 3A presents a side view diagram of one embodiment of the microfluidic device and pressure interface of the system of the invention.

FIG. 3B presents a top view diagram of one embodiment of the microfluidic device of the system of the invention.

FIGS. 15A-D illustrate aspects of an example system including a microfluidic device and interface according to specific embodiments of the invention.

FIGS. 45A-B illustrate alternative microfluidic device and plate designs of the invention.

FIGS. 46A-C are illustrative photomicrographs showing alternative biofilms in conjunction with certain embodiments of the microfluidic device of the invention.

DETAILED DESCRIPTION OF THE INVENTION

The apparatus and methods described herein relate generally to the manipulation of particle suspensions (e.g., cell suspensions) and are useful for applications including but not limited to flow cytometry, ion-channel electrophysiology, single cell electroporation, controlled shear force in vivo-simulating cell culture and numerous related biotechnology approaches.

Recently introduced imaging flow cytometers aim to combine the speed and ease of use of flow cytometry with the high information content of Image Scanning Cytometry (Bonetta 2005). The instrument images cells as they flow by at high velocity in a single file. The requirement of assembling in-flight images of single cells requires a great deal of custom technical development, which translates in a relatively high price for such devices (approx. $300 k for ImageStream 100) and relegates their use to core labs and pharmaceutical companies.

Disclosed herein is an alternate technique that is based on accurate flow control in a microfluidic channel. In one embodiment of the device, a particle suspension is introduced into a viewing window and imaged under various imaging modes. Flow is restarted and a new batch of cells is introduced for the next imaging sequence. In this way, libraries of single cell information may be assembled and analyzed.

Another embodiment of the device can be applied to ion channel recording. Ion channels are functional units of all living systems and fulfill a number of roles, from fast signal transmission in the nervous system to regulation of biochemical pathways. In turn, a number of disorders have been linked to ion channel malfunction. Ion channels are implicated in mental disorders such as Alzheimer's and epilepsy, as well as heart disease, diabetes and neuromuscular disease [Shaffer]. Consequently, these transmembrane proteins are attractive drug targets and constitute about 20-30% of new drug development campaigns [Southhan].

The electrophysiology recording technique, termed patch clamp, has emerged as the gold standard in the study of ion channel function. It is based on the ability to perform recordings of transmembrane currents through a specific ion channel type. Traditionally, patch clamp recording is accomplished with a micromanipulator-positioned glass pipette under a microscope. This technique was perfected in 1981-'83 by Nether and Sackmann through the achievement of high resistance seals between the glass pipette tip and the cell membrane. The basic setup is illustrated in FIG. 5A. Current that passes through the ion channels in either the membrane patch or the whole cell membrane is recorded at different bias voltages.

Figure 7:
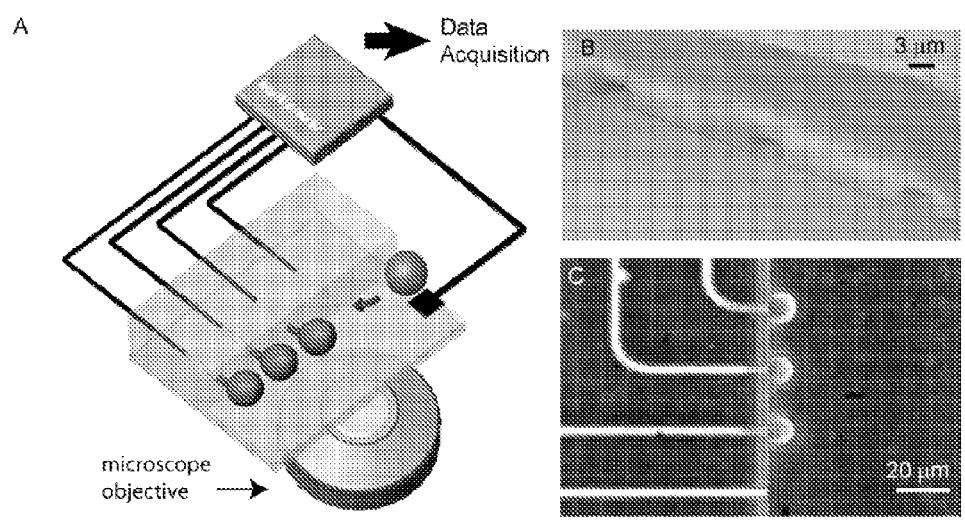
FIGS. 7A-C illustrate aspects of an example microfluidic device including optical monitoring according to specific embodiments of the invention.
Figure 8:
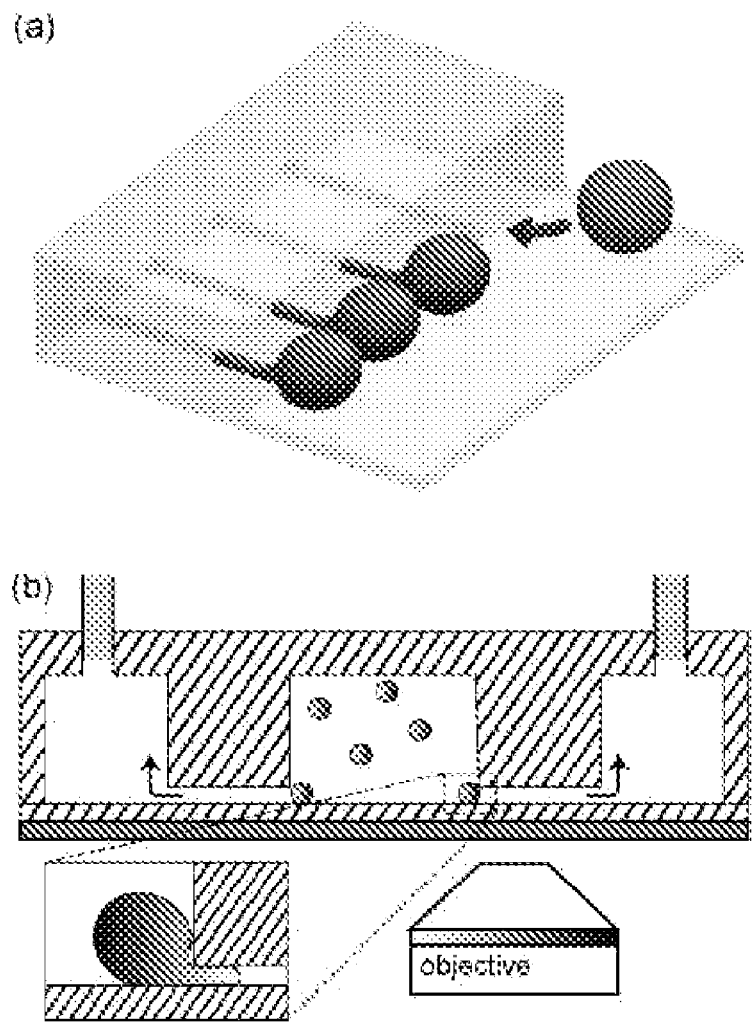
FIGS. 8A-B illustrate aspects of another exemplary integrated cellular manipulation array on microfluidic platform, including optical monitoring according to specific embodiments of the invention.

Illustrated in FIG. 7, is one aspect of a patch clamp array integrated with microfluidics that provides for simultaneous optical and electrophysiological measurements. The microfluidic designs have been previously described in U.S. Provisional Application No. 60/710,305 filed on Aug. 21, 2005. A number of the images shown here are reproduced from the application referenced above for clarity: As shown in FIG. 7 panel A, cell trapping can be achieved by applying negative pressure to recording capillaries or channels which open into a main chamber or channel containing cells in suspension. Attached or trapped cells deform, protruding into the capillaries (see panel A of FIGS. 7 and 8). The device can bonded (or otherwise attached or connected) to a glass coverslip for optical monitoring. In FIG. 7 panel B, a scanning electron micrograph shows three recording capillary orifices as seen from the main chamber. FIG. 7 panel C shows a Darkfield optical microscope image of cells trapped at three capillary orifices. FIG. 8 panel B shows a cross-sectional view of the device illustrating cell trapping and optical monitoring. As illustrated in FIG. 8, in one aspect of the device described herein cell trapping occurs laterally. The present invention relates the integration of said microfluidic device with fluid filled reservoirs for reagent loading. Also, it describes methods for interfacing integrated devices with outside pressure sources and electrical connections.

In one embodiment, a microfluidic system for trapping individual particles in a closely-packed array for observation and monitoring is provided. As used herein an array refers generally to an orderly arrangement, for example, an orderly arrangement of immobilized particles (e.g., immobilized cells). It is envisioned that two-dimensional arrays are included when referring to arrays herein. The system can include a microfluidic substrate layer with at least two microscale channels or capillaries intersecting with a main flow channel, a multi-well structure (e.g., a 96-well microplate). The multi-well structure can be bonded to the microfluidic layer, with the reservoirs or wells of the multi-well structure in fluid communication with the channels of the microfluidic layer. Also included can be an interface which is removably coupled to the microfluidic device, which controls the flow of fluid in the microfluidic channels and can apply a positive or negative pressure to each of the wells of the multi-well plate, thereby applying positive or negative pressure to the microscale channels in the microfluidic layer.

In one embodiment, the microscale channels are adapted to trap particles including but not limited to cells, vesicles, oocytes, and the like, that are flowing through the main flow channel. In one embodiment, the microscale channels can be about 0.5-10 um in width and about 0.5-10 um in depth. Additionally, the main flow channel can be about 100-200 um in width and about 20-100 um in depth. In one embodiment, each microscale channel is in fluid communication with one well of the multi-well plate. In another embodiment, the main flow channel is connected to two or more wells of the multi-well plate, with channels terminating in the wells.

Figure 5:
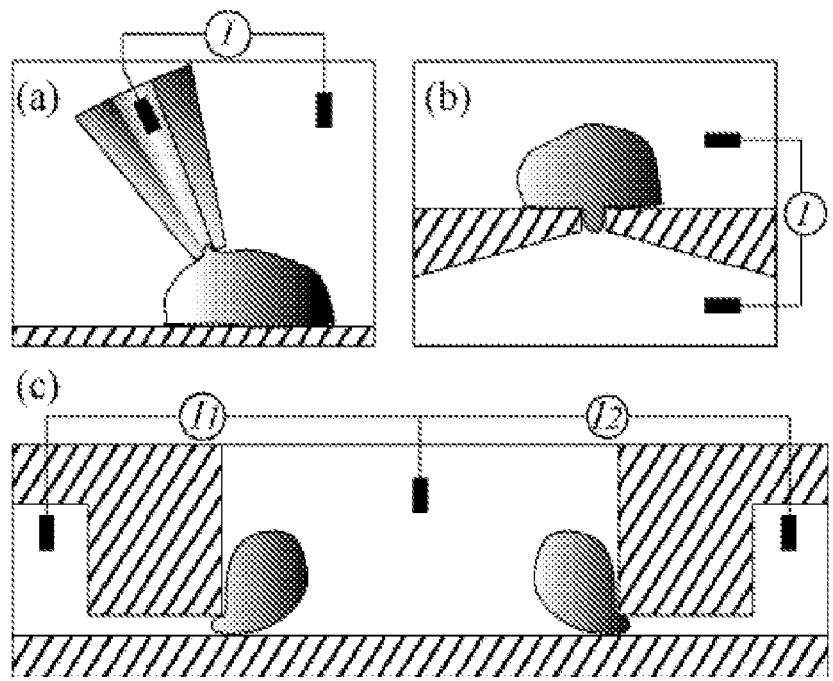
FIG. 5A is a schematic of a prior art glass micropipette patch clamp device.
FIG. 5B is a schematic of a prior art on-chip planar patch clamp device.
FIG. 5C is a schematic of prior art patch clamp device including patch channels on the sides of a central channel.

Generally, modern designs replace the pulled glass pipette (shown in FIG. 5 panel A) with an orifice in a planar substrate (shown in FIG. 5 panel B). Several substrate materials have been explored for this purpose including: silicon elastomer [Klemic], quartz [Fertig (Whole Cell Patch)] or glass [Fertig (Activity of Single)] substrates. Most chip-based devices developed to date use the planar geometry shown in FIG. 5 panel B where a single patch pore is etched in a horizontal membrane or substrate dividing the top cell compartment from the recording electrode compartment. Whole cell recordings have been demonstrated with mammalian cells using glass substrates [Fertig (Whole Cell Patch)] and with *Xenopus* oocytes using elastomer substrates [Klemic]. Cell-attached patch recordings have also been demonstrated for glass substrates [Fertig (Activity of Single)]. Substrates such as silicon that require micromachining can be substituted for polydimethylsiloxane (PDMS) which can be micromolded. Replacing silicon micromachining with PDMS micromolding has two important technological advantages: First, the fabrication is sufficiently simple (requiring only molding and bonding) and economical to enable a cost per data point on par with fluorescent methods (i.e., $0.2 per data point). Second, unlike silicon based devices, the PDMS device is translucent, permitting placement on the stage of an inverted microscope and visualization of a large number of trapped cells during recording. The ability of PDMS to obtain giga-ohm seals has been confirmed by Klemic et al. [Klemic] by performing whole cell recordings (*Xenopus* oocytes and mammalian cells) using pores in a micromolded planar substrate and plasma surface treatment. Plasma treatment was used to make the PDMS surface hydrophilic but the effects are temporary, requiring the device be used within hours to days of fabrication.

Despite important improvements, existing approaches can only be used in secondary screening applications (<3000 data points per day) and retain a high price per data point (4-5× that of fluorescent reporters) [Southhan]. In one embodiment, the device described herein uses microfluidic reagent delivery to enable primary screening at price parity with fluorescent methods, while providing simultaneous optical access to the cells.

Figure 6:
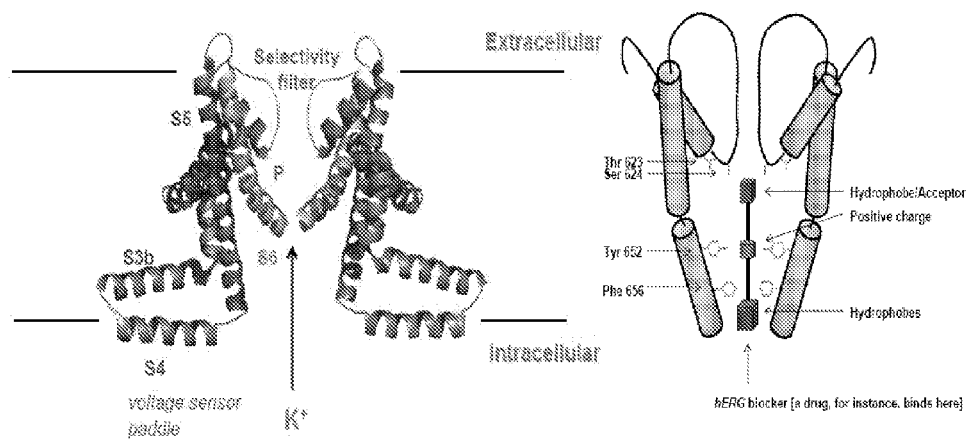
FIG. 6 shows schematic illustrations of the hERG K+ ion channel without and with a bound blocker.

Applications of the invention described include but are not limited to toxicology, drug screening, drug discovery, cell line characterization, cell selection, and others. In June 2005, the FDA mandated that all drugs must be tested against the outward rectifying potassium (K) ion channel hERG, (see FIG. 6), whose unpredicted adverse modulation by several blockbuster drugs has been implicated in long-QT syndrome and subsequent sudden death by heart malfunction [Denyer]. It has been estimated that approximately 25-40% of all lead compounds show hERG activity in vitro [Bennett].

The gold standard assay for hERG safety screening is the patch clamp: the cell is voltage clamped in whole-cell configuration (using a glass pipette) while the test compounds are introduced extracellularly. The response of the cell to the test compounds is evident from the current response of the cell when the compounds have reached the ion channel's binding site which, in the case of hERG, is on the intracellular portion of the molecule (see FIG. 6). Source: Enal Razvi [Southhan]. The problem with this approach is that the compounds are notoriously slow to diffuse through the membrane to reach this binding site (t>20 minutes). In addition, multiple compound concentrations need to be applied sequentially to the same patched cell in order to provide consistent measurement. Consequently, hERG measurements often fail due to the lack of long term stability for the high resistance seal between the glass pipette and the cell (seals often degrade in t<20 minutes).

As described above, a majority of currently available automated patch clamp devices utilize a pore in a planar substrate to immobilize single cells and establish a seal (FIG. 5b). Consequently, recording electrodes must be placed in both the top and bottom compartments, obscuring optical access to the cells being recorded, and making the application and removal of multiple compounds difficult.

One of the inventions disclosed herein is an alternative to the techniques described above, based on the use of a junction between two microfluidic channels to immobilize single cells, as opposed to a pore in a planar substrate (FIG. 5c).

Another important application of the invention relates to the discovery of targeted gene silencing by RNA interference presents a tremendous new opportunity for the field of drug discovery. Before this can happen, however, significant challenges with respect to intracellular targeting and delivery of short interfering RNA (siRNA) must be overcome.

One way to traverse the cell membrane and access the cell's interior is by temporarily increasing the permeability of the cell membrane. This can be accomplished via electroporation, a technique which uses high electric fields to induce structural rearrangements of the cell membrane. Pores result when the transmembrane potential exceeds the dielectric breakdown voltage of the membrane (0.2-1.5V) [Weaver]. Polar substances otherwise impermeant to the plasma membrane (such as dyes, drugs, DNA, proteins, peptides, and amino acids) can thus be introduced into the cell.

In the early 1980s, Eberhard Neumann et al. demonstrated the feasibility of electroporation for delivering DNA to a population of mammalian cells [Lundqvist]. Since then, this method of bulk electroporation has become a standard technique routinely used to simultaneously transfect millions of cells in culture. Most commercially available electroporation systems still use Neumann's approach without too much variation. Bulk electroporation requires very high voltages (kVolts) and has little control over the permeabilization of individual cells, resulting in suboptimal parameters. Moreover, because different cell types require different electric field parameters to electroporate, the system has to be calibrated to determine appropriate pulse conditions a priori without any real-time control. Reversible electroporation, in which the pores can reseal, is therefore difficult [Chang, D.

C.]. As a result, most commercial systems focus on improving buffer solutions to improve cell viability. Examples of commercial electroporation platforms include the Gene Pulser Xcell™ Eukaryotic System (Bio-Rad Laboratories), BTX® HT 96 Well Electroporation System (BTX® Molecular Delivery Systems), Nucleofector™ 96-well Shuttle System (Amaxa Biosystems), and Axoporator 800A (Molecular Devices).

Single cell electroporation obviates many of the challenges associated with bulk electroporation but is less common. Lundqvist et al first demonstrated single cell electroporation using carbon fiber microelectrodes in 1998 [Lundqvist]. To induce electroporation, they placed microelectrodes 2-5 microns away from adherent progenitor cells. Other single cell electroporation techniques developed since include: electrolyte-filled capillaries [Nolkrantz (Electroporation)], micropipettes [Hass, Rae], and chips [Huang]. For successful single cell electroporation, the cell must either be isolated or the electric field well focused to target a particular cell [Nolkrantz (Functional Screening)]

One aspect of the invention disclosed herein uses a junction between two microfluidic channels to trap single cells or collections of cells for controlled electroporation. This method has significant advantages with respect to bulk electroporation as described above, as well as with respect to single cell electroporation setups where the cell is immobilized above an aperture in a planar substrate.

Contact adhesion between cells and between cells and surfaces is central to a large number of biological phenomena. For example, cellular adhesion is involved in blood clotting, tissue repair, immune and inflammatory responses, bacterial infections, and cancer progression. A widely used method to quantify cell adhesion is the application of a range of shear forces in flow chambers. The same method is used to determine the cellular response to shear stress through mechanotransduction pathways. Application of controlled shear force to cells in culture in useful since it provides a simulation of an in vivo condition, namely shear force as a result of, for example fluid flow in relation to the culture.

Biofilms is another area where cellular adhesion places a key role. The bulk of biofilm research is performed using macroscopic laminar flow chambers that suffer from limited throughput, cumbersome apparatus assembly, experiment failure (i.e. by bubble introduction), and a limited range of applicable shear forces. Additionally, there is a dearth of integrated, user-friendly biofilm research platforms. As a result, users are forced to assemble their own systems, which often suffer from long setup times, high media consumption, poor or no shear rate control, and cumbersome sterilization procedures.

Described herein is a novel microfluidic experimental system (BioFlux) that avoids the problems identified above by utilizing programmable, computer controlled all flow rates in conjunction with microfluidic design to generate a wide range of unique flow conditions that offer larger dynamic range for laminar flows, better flow field uniformity, different flow regimes (turbulence, flow junctions, etc), reduce reagent consumption and simplified sterilization procedures. While other microfluidic device configurations have been proposed for performing shear force experiments [Lu, Koo et al. 2004), the disclosed devices differ in that no tubing is directly attached to the microfluidic device; instead dispensing reservoirs are incorporated into the device. The integration of microfluidics with loading reservoirs on 24 or 96-well plates provides important workflow and throughput advantages. Additionally, for multi-shear experiments, the disclosed designs offer the advantage of a consistent same-width observation area for all shear rates assayed.

In general, one aspect of the disclosed invention consists of a microfluidic layer irreversibly bonded to a plate containing perforations which may be used as fluidic reservoirs for reagents. For some applications, imaging is an important component of data collection, and high resolution images of cells in a microfluidic channel that belongs to the microfluidic layer are shown in FIG. 1A and FIG. 1B. Individual images of cells in the channel at higher magnifications and for a number of fluorescent wavelengths are shown in FIG. 1C.

Figure 2:
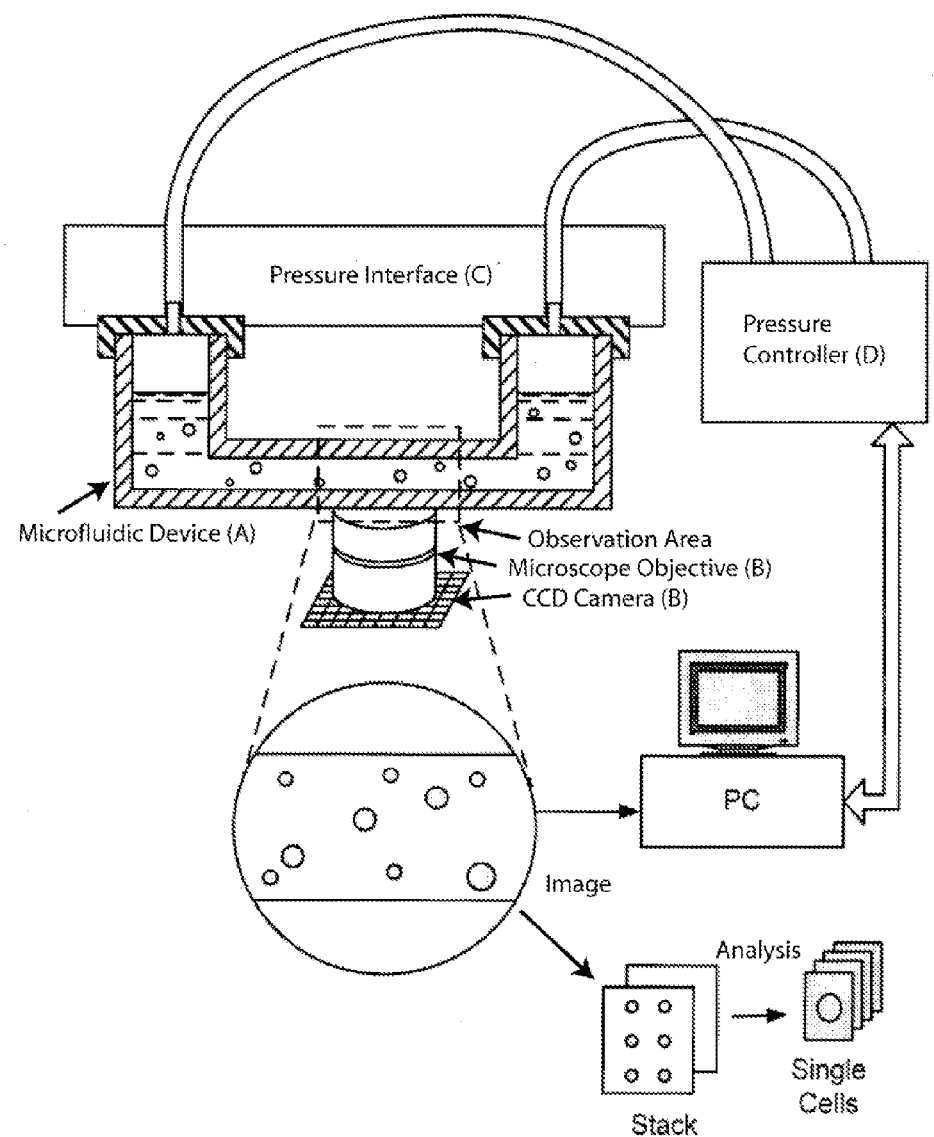
FIG. 2 presents an exemplary system diagram for one embodiment of the Stop-Flow Cytometer. The illustrated embodiment includes: (A) a disposable microfluidic device including input and output well(s) and a microfluidic channel connecting the two; (B) an imaging system including an objective and a CCD camera; (C) a pressure interface to the microfluidic device that connects to (D) a computer controlled pressure source; and a PC.

Also, a number of the applications proposed may have in common the method of integrating a microfluidic layer with fluid reservoirs, as well as the method of driven flow through said microfluidic channels by mating to a pressure deliver device (FIG. 2). Another embodiment of the devices and interface to pressure sources is shown in FIG. 3.

Imaging Flow Cytometer

The operation of the imaging flow cytometer is based on leveraging the advantages of microfluidics and precise flow control for generating particle counts, statistics on cell fluorescent properties, and a correlated database of cell images for all of the counted cells.

Particles may be, for example, cells, beads, bacterial cells, vesicles, Oocytes, collections of cells such as cell clumps or embryonic bodies, or embryos.

Typical operation can proceed according the following exemplary steps. A particle suspension is loaded in the disposable microfluidic device 'input' well. The microfluidic device includes both reservoirs for cell input and output, and may also include additional reservoirs for the addition of compounds to the particle suspensions while in the device. The general layout of the device is described in a previously filed patent application Ser. No. 60/744,034, filed Mar. 31, 2006, which is incorporated herein by reference in its entirety), and it consists of a microfluidic layer coupled to a plate with apertures, that may include wells for retaining fluid. The device may be manufactured, for example, from PDMS, a thermoplastic material, glass, or a combination of the above.

In general in one aspect a microfluidic system is provided for the analysis of particle suspensions. The system includes a microfluidic layer with at least one microscale flow channel comprising a microflow channel and a main flow channel; a structure including one or more reservoirs coupled to the microfluidic layer, wherein the reservoirs of the structure are in fluid communication with the microflow and main flow channels of the microfluidic layer; an interface detachably connectable to the microfluidic layer, wherein the interface controls fluid flow and pressure to one or more reservoirs, thereby controlling pressure delivery to each microscale flow channel; and an observation area for acquiring images of the particle suspension. In one embodiment, the main flow channel is substantially 100-2000 um in width and substantially 5-200 um in depth. In another embodiment, the microscale channels are in fluid communication with one reservoir of the structure. In a further embodiment, the microscale channels are in fluid communication with a plurality of reservoirs of the structure, and the microscale channels can optionally terminate in the reservoirs (FIG. 2).

In general in another aspect a method for analyzing a plurality of individual particles in suspension is provided. The method includes the steps of repeatedly introducing pluralities of particles into a microfluidic chamber via flow; repeatedly acquiring images of the particles; and analyzing the acquired images to characterize the particle population. In one embodiment the microfluidic chamber is a section of a microfluidic channel.

In one embodiment the flow includes a flow velocity and the flow velocity alternates between a fast flow velocity (v>100 um/s) and a reduced flow velocity (v<1 um/s). In a related embodiment, image acquisition occurs during periods of a reduced flow velocity.

Figure 1:
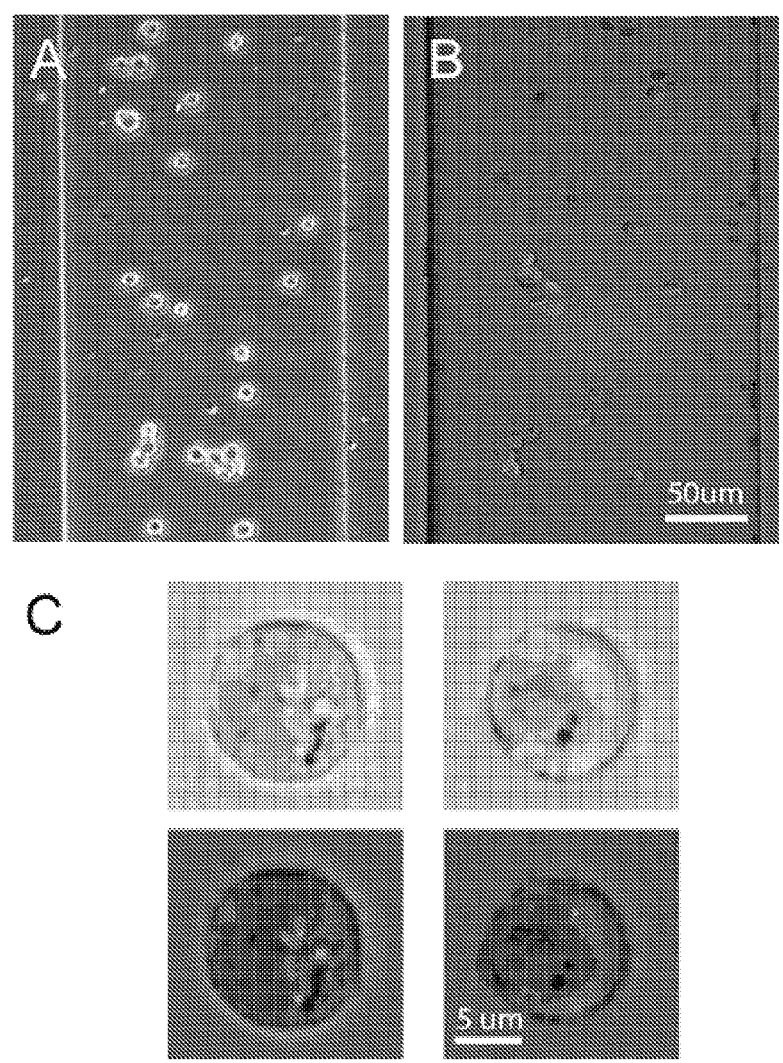
FIG. 1 presents sample images acquired from one embodiment of the device during stopped flow. A number of fluorescently labeled cells are shown placed in the viewing window and imaged in phase mode (A), and fluorescence (B). Data containing single cell images is shown assembled in (C).

In another embodiment analyzing the acquired images includes creating a set of individual particle images. In a related embodiment characterizing the particle population includes characterization of determining total particle counts, particle density in suspension, and/or particle size distribution. In a further embodiment characterizing the particle population includes characterization by, for example, determining fluorescent intensity, fluorescent marker distribution within the body or periphery of the particle, and/or classification of particles based on fluorescent intensity and/or fluorescent marker distribution and/or fluorescence lifetime. It is envisioned that images can be acquired utilizing, for example, optical microscopy, fluorescence microscopy, phase contrast microscopy, and/or confocal microscopy. Exemplary microscopic images are shown in FIG. 1.

In a particular embodiment analysis of images includes automatic particle recognition and storage of individual particle images.

In general, in one aspect, the invention provides a system for performing particle imaging, counting, characterization, and classification is provided. The system includes a microfluidic device containing a chamber that can accommodate and allow for simultaneous imaging of a plurality of particles; a flow actuation system that can introduce a population of particles into the chamber; an image acquisition system; and an image analysis system. In one embodiment, the microfluidic chamber is a section of a microfluidic channel that can be part of a microfluidic network. In a further embodiment the inlet and outlet of the microfluidic channel(s) are mated to wells. It is envisioned that the wells can be disposed in a standard well plate format, including, for example, 6-well, 24-well, 96-well, 384-well, and/or 1536-well plates.

It is envisioned in the present embodiment that the flow actuation system can provide adjustable switching between a fast flow velocity (v>100 um/s) and reduced flow velocity (v<1 um/s). In a particular embodiment the flow actuation system includes a pressure application apparatus. In another embodiment the flow actuation system includes an electrokinetic flow apparatus. In yet another embodiment flow is driven by applying a differential pressure to the input and output of the microfluidic chamber.

It is envisioned that in the present system the image acquisition system can include a standard microscope equipped with a CCD camera. In one embodiment the image acquisition system includes a microscope objective and a CCD camera, mounted in an enclosure. In a particular embodiment the enclosure is a microscope chassis. In another embodiment the image analysis system includes a microprocessor and a software application. It is envisioned that the software application can provide for the recognition of individual particles within the acquired images. It is further envisioned that the software application can measures the size and morphological parameters of recognized particles and then classify particles based on size and morphological parameters. In one embodiment the software application measures the fluorescence intensity and fluorescent distribution inside the perimeter of each recognized particle. It is envisioned that the software application can classify particles based on fluorescence intensity and fluorescent distribution inside the perimeter of each recognized particle.

In general, in another aspect the invention provides a microfluidic system for sorting individual particles based on optical observation. The system includes a microfluidic layer with at least two microscale channels intersecting with a main flow channel; a multi-well structure with said structure bonded to the microfluidic layer, with the wells of said multi-well structure in fluid communication with the channels of the microfluidic layer; an interface which is removably coupled to the microfluidic device which controls the flow of fluid in the microfluidic channels and can apply a positive or negative pressure to each of the wells of the multi-well plate, thereby applying positive or negative pressure to the microscale channels in the microfluidic layer; and a control system for particle recognition and selective pressure application depending on particle position.

In general, in yet another aspect the invention provides a microfluidic system including a structure having a plurality of bottomless reservoirs; and a substrate comprising microfluidic channels on one side, said substrate coupled to the structure with the channel side facing the substrate, wherein the microfluidic channels are in alignment with the bottomless reservoirs of the structure such that the reservoirs of the structure are in fluidic communication with the microfluidic channels.

In general in another aspect the invention provides a microfluidic device including a structure wherein the structure includes a plurality of reservoirs; and a substrate coupled with the structure and comprising one or more main flow channel, a plurality of trapping channels and a detection zone for viewing cells microscopically, wherein one or more reservoir is in fluid communication with one or more trapping channel, and wherein each trapping channel is in fluid communication with one or more main flow channel, and wherein the detection zone is adapted for viewing cells using an upright microscope or an inverted microscope.

As illustrated in FIGS. 2 and 3, an observation area may be used to obtain imaging data that is part of one of the microfluidic channels. A set of cells can be first flowed into the observation area of the cartridge. Images can be acquired during reduced or essentially stopped flow or fully stopped flow in the observation area. A key feature of the system is the ability to monitor and stop flow completely (or essentially completely by reducing flow), to where cells are moving by <500 nm during the looms long exposure time required for image acquisition.

Images of the cells can be acquired in bright field (BF), and a variety of fluorescence wavelengths. Multiple wavelengths are envisioned, including the use of a plurality of fluorescent wavelengths (e.g. 2 or more and 3 or more wavelengths). Images may be acquired using a standard upright or inverted microscope, as well as using a custom imaging apparatus containing a microscope objective and a CCD camera.

Fluorescence image exposure times can be set by the user, but will nominally be around 100 ms (although it is envisioned that exposure time can range any of a number of times between 1 ms and 10 seconds) for each filter set (alternatively e.g., around 30 ms for BF images). The image exposure times will set the throughput of the proposed system. For example, a full set of images may be acquired in approx 30+100×3=330 ms. FIG. 1 shows a set of images obtained in BF, e.g., phase mode, and fluorescence using a microfluidic chamber. A resulting set of single cell images is shown in FIG. 1C. After the first set of images is obtained, flow is initiated again for a short time (t=20 ms) and stopped again for the next image acquisition operation. The period of each operation cycle is therefore 330+20=350 ms. It is envisioned that any of a number of other time periods for the flow can be useful including, for example, between 1 ms to 10 seconds. Because the imaging region remains the same, after focus is achieved for the first image, no focusing adjustments have to be made for subsequent images. Initial focusing can be passive (by careful mechanical design of the consumable/interface) or active through autofocus routines.

From BF images, cell classification can be performed based on size and morphological parameters (shape, variability). The fluorescent images are analyzed in terms of overall intensity (data similar to flow cytometry) as well as intracellular distribution and correlation between different tagged cell contents. Co-localization studies are an important enabled application that differentiates this product form flow cytometry.

If pairs of cells or cell clumps are present in the field of view, they can be analyzed as well, resulting in data on cell-cell association, and intracellular distribution of biomolecules resulting from interactions between the cells. This is a unique capability of the system, as other flow cytometers necessitate single cell suspensions for proper operation. Imaging cytometers may be able to looks at pairs of cells, but not larger aggregates.

Part of image analysis is the recognition of individual particles in suspension, and classification of such particles. Published work on static cell recognition (Ionescu-Zanetti, Wang et al. 2005; Long, Cleveland et al. 2006 both of which are incorporated in their entirety herein by reference) shows that a field of view (512×512 pixels) containing 20-50 cells can be analyzed in about 1 s using a dedicated program. The implementation of the cell ID/analysis program (on a 1 Ghz Pent II) was about ⅓ that of the acquisition frame rate. It is envisioned that program improvements will enable the cell ID operations to be performed in real time. If analyzed off-line, an experiment requiring identification of a 50,000 cell population would only take 3.3 min to analyze, compared to the image acquisition time of 1.17 min. Therefore, the operator will be able to obtain the results immediately following the experiment.

Key specifications of an exemplary embodiment of the system can include:
  Throughput 250 cells/s
  Image resolution 0.5 um/pixel
  Pixels/cell (20 um diameter) 1600
  Starting sample volume 200 uL
  Imaging Cytometer: Applications and Benefits An imaging cytometer provides key advantages over traditional flow cytometry. Morphology information from phase images can be used to classify cells based on appearance (i.e. size, sphericity, and refractive index). This information alone may be used to differentiate subpopulations w/in a heterogeneous cell mixture (for example freshly dissociated primary cells).

The measurement of fluorescent distribution within the cell perimeter contains additional data on organelle content, nuclear transport and membrane association of protein, to name a few cellular phenomena.

In addition, there are a number of important advantages over the current imaging cytometer systems that result from the flexible stop-flow operation of the present invention including but not limited to:

1. Tunable exposure times. Low intensity florescent signals may require longer integration times for high quality imaging. In the system disclosed herein, the integration time is user-determined. While it does slow down system throughput, this feature is enabling for a class of experiments. In contrast, constant flow implementations require that the exposure times remain constant from experiment to experiment and for all filter sets used.

2. Precise focus. While in current systems the cells are positioned by sheath flow and can move as much as a few um in the Z direction, in the present system cells are sequestered in the optical plane by the size of the imaging chamber, and retain precise focus at the same Z height for all of the cells imaged.

3. No cell rotation. Cells under flow conditions may rotate while passing the detector. Stopped (or reduced) flow means that little or no movement happens during exposure, increasing image quality.

4. Absolute particle counting ability. Current imaging flow cytometers use sheath fluid to hydrodynamically focus the cells of interest into a single file order. Because the volume of the space occupied by the cells and sheath fluid is not precisely known, absolute cell concentrations cannot be determined. Such instruments have to be calibrated using bead solutions in order to ensure accurate density measurements.

5. Illumination flexibility. Current imaging flow cytometers rely on high powered laser illumination to elicit fluorescence emission from fluorophores. Lower powered lasers and arc lamp based illumination are incapable of providing sufficient intensity during the extremely short time that the cell is illuminated (10 ms). Since the current invention does not require that the cells be moving during exposure, much lower powered illumination sources may be used providing much more flexibility of operation.

Imaging Cytometer: Supporting Data

Experiments using fabricated embodiments of the invention have resulted in the production and validation of microfluidic devices and flow control apparatus enabling stop-flow cytometry. Specifically, the design and fabrication of microfluidic channels capable of transport of a particle suspension (cells) and optical observation of cells inside said microfluidic channel have been achieved. Introduction of particles in the viewing window and flow control was obtained using delivery of a regulated pressure to the channel input under solenoid valve control. The release of pressure from the system in the 'stopped flow' state was designed to quickly (t<30 ms) bring fluid/particle velocity to 0 for imaging. The images (FIG. 1) were obtained on a standard inverted microscope in BF, phase, and fluorescence imaging modes.

Interface and Pneumatic Control of a Microfluidic Stop-Flow Imaging Cytometer

FIG. 2 illustrates an exemplary system diagram for the Stop-Flow Cytometer. One embodiment of the proposed product can include the following components: (A) a disposable microfluidic device including input and output well(s) and a microfluidic channel connecting the two, (B) an imaging system including an objective and a CCD camera, (C) a pressure interface to the microfluidic device that connects to (D) a computer controlled pressure source. A PC or other logic device can be used to coordinate cell suspension flow with the imaging system such that cells are imaged while stationary. The acquired image stack (both BF and fluorescent data) is then processed and assembled into single cell images, while single cell characteristics (e.g. morphology, brightness, intracellular distribution) are written to data files.

FIG. 2 illustrates the parts of the system for counting particles as described herein. In the side view (A), a device including a microfluidic layer and a structure containing reservoirs is shown. The structure can be irreversibly bonded to the fluidic layer. The pressure interface can be reversibly mated to the top of the reservoir structure to form a pressure seal. Tubing can be used to apply pressure to the reservoirs. A top-down view of the device only (no interface) is shown in (B). The corresponding reservoirs in the upper structure, the microfluidic channels and viewing area for image acquisition are all identified.

In one embodiment, a result obtained using the methods described herein is used to determine, for example, cell morphology, cell count, organelle content, nuclear transport and membrane association of protein, and/or diagnose a disease state of an individual, for example, a patient. In a particular embodiment, determining cell morphology, cell count, organelle content, and/or nuclear transport and membrane association of protein includes reviewing or analyzing data relating to the imaged properties of an individual's cell or cells. In one embodiment, the method of diagnosing a disease comprises reviewing or analyzing data relating to the presence and/or the concentration level of a target in a sample. In any case, a conclusion can be provided to a patient, a health care provider or a health care manager, the conclusion being based on the review or analysis of data regarding, for example, cell morphology, cell count, organelle content, nuclear transport and membrane association of protein, and/or a disease diagnosis. It is envisioned that in another embodiment the providing a conclusion to a patient, a health care provider or a health care manager includes transmission of the data over a network.

Figure 4:
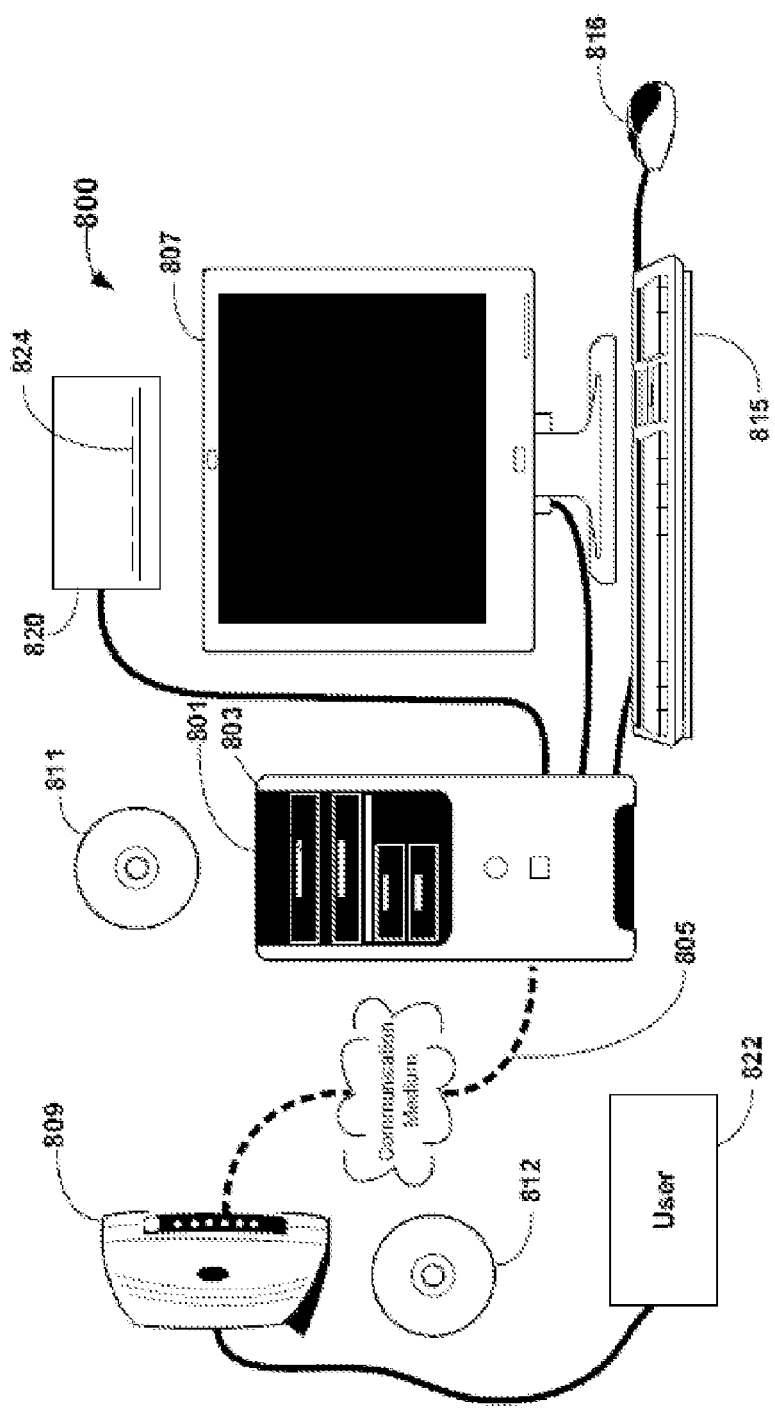
FIG. 4 is block diagram showing a representative example logic device in communication with the system according to specific embodiments of the invention.

FIG. 4 is a block diagram showing a representative example logic device through which reviewing or analyzing data relating to the present invention can be achieved. Such data can be in relation to a disease, disorder or condition in an individual. FIG. 4 shows a computer system (or digital device) 800 connected to an apparatus 820 for use with the stop-flow cytometry system 824 to, for example, produce a result. The computer system 800 may be understood as a logical apparatus that can read instructions from media 811 and/or network port 805, which can optionally be connected to server 809 having fixed media 812. The system shown in FIG. 4 includes CPU 801, disk drives 803, optional input devices such as keyboard 815 and/or mouse 816 and optional monitor 807. Data communication can be achieved through the indicated communication medium to a server 809 at a local or a remote location. The communication medium can include any means of transmitting and/or receiving data. For example, the communication medium can be a network connection, a wireless connection or an internet connection. Such a connection provide for communication over the World Wide Web. It is envisioned that data relating to the present invention can be transmitted over such networks or connections for reception and/or review by a party 822. The receiving party or user 822 can be a patient, a health care provider or a health care manager.

In one embodiment, a computer-readable medium includes a medium suitable for transmission of a result of an analysis of an environmental or biological sample. The medium can include a result regarding a disease condition or state of a subject, wherein such a result is derived using the methods described herein.

Microfluidic Device and Attendant Apparatus for Automated Electrophysiology Measurements In one embodiment, a microfluidic array is provided for automated patch clamp recordings using the design concept presented in FIGS. 7 and 8. The design of the array can include fabrication using PDMS micromolding, a high-throughput, inexpensive procedure. This is ideal for rapid prototyping of designs, while providing for the built-in integration of the patch pores with a network of fluidic connections. Both extracellular and intracellular solutions can be exchanged on short time scales, as described herein. Fast exchange of extracellular media (e.g., time on $(t_{on})$<ms) can be achieved. In one embodiment patch arrays are fabricated such that they contain pore orifices or trapping sites that are about 20 μm apart (FIG. 8 panel A). In one embodiment the pore orifices of the arrays are less than 100 μm apart. In another embodiment, the pore orifices of the arrays are less than 25 μm apart. In a further embodiment, the pore orifices of the arrays are less than 5 μm apart. For this array, channel binding ligands can be administered in small volumes (e.g., Vchamber=0.4 pL), while the effects on channel activity can be recorded in parallel at a number of patch sites (e.g., n=12). Similar devices have been described in U.S. Provisional Application No. 60/710,305, filed on Aug. 21, 2005, which is incorporated herein by reference. The instant disclosure describes additional embodiments that are based on the trapping of single cells, and include the integration of fluid reservoirs that are interfaced with pressure source(s) and electrodes assemblie(s).

The horizontal geometry of the recording capillaries reduces capacitive coupling between the cell reservoir and the patch channel, a determining factor for low noise channel recording. This is because there are no large area thin planar structures dividing the intracellular chamber from the extracellular chamber. In the case of pipettes, the pipette wall is such a surface and the major cause of capacitive coupling. This is reduced by the application of viscous fluid coatings to the pipette, but is an additional procedural step. In the case of planar patch designs, the coupling happens across the planar substrate dividing the top (extracellular) from the bottom (intracellular) chambers. In one embodiment the array device capacitive coupling can be <10 fF. In one embodiment the array device capacitive coupling can be <1 pF. The resistance of the patch channel (access resistance) can also be optimized by altering the capillary geometry.

In general, in one aspect, the microfluidic arrays described herein are useful in the application of reagents under controlled time scales and volumes. Most patch clamp studies of ion channels depend on the delivery of ligands to determine their gating effects. Ligands can also be used to gain insight into the gating mechanism of various channels, and the change in the effects of ligands after genetic modification of the channel can result in the identification of the function of removed genes. In this context, the device allows for the rapid ligand application in small volumes (e.g., V<1 nl). In one embodiment the ligand application volume is less than 1 μl. In another embodiment the ligand application volume is less than 1 nl. In one embodiment the ligand application volume is less than 10 fl. The use of small volumes makes possible the application of monotonically increasing ligand concentrations in order to determine the point at which the concentration is high enough to effect gating. This in turn relates to channel-ligand bonding and gating efficacy. Traditional patch experiments require the exchange of solution in a culture dish. Using on-chip mixing enables arbitrary concentrations of the ligands and rapidly obtained titration curves for their binding to transmembrane proteins of interest. Importantly, both intracellular and extracellular perfusion can be easily implemented, enabling the study of compounds that bind to the intracellular side of the ion channel.

Besides ligand delivery, another important feature of integrated fluidics is the ability to exchange ligands and electrolyte solutions quickly and easily with minimum disturbance of the patch site. In one embodiment such techniques can be used to switch from electrolytes selecting for one channel type to electrolytes selecting for another channel type quickly, while patch seals are maintained.

In another aspect, the microfluidic arrays presented herein provide for optical multiplexing and high content screening. Images of patched cells can be acquired for planar patch geometries if the substrate is thin enough and there is optical access to the recording site. However, because of the necessity to place electrodes assemblies both below and above the recording pore, none of the high throughput systems currently available provide optical access to the cells being recorded from. Consequently, determining the state of the cell suspension (cell health, clumping, and the presence of debris at the recording site) is currently impossible. Even if optical access was provided for future instruments, recording sites are placed d>1 mm apart, making it impossible to record optical data for all patched cells simultaneously. In one embodiment an array geometry is provided such that the devices are bonded to glass cover slips and both the cell and the membrane protrusion into the channel are in the same optical plane (see FIG. 7 panel A) wherein a microscope objective is shown. This provides excellent compatibility with a majority of microscope objectives, including low working distance (d<0.5 mm), oil immersion objectives, and confocal microscopy. In the example illustrated in FIG. 7, the device design for a high density patch clamp array includes: cell trapping in adjacent recording capillaries (see panel A) is achieved by applying negative pressure to outside tubing connections while cells are visualized on the stage of an inverted microscope. Because cells are in close proximity in an array format, at least 16 cells can be observed simultaneously in the same field of view. Microscopy enables measurements of both membrane deformation and fluorescent marker data within the cell in conjunction with current recordings. The accurate measurement of cell shape, together with real time seal resistance measurements will be necessary for a thorough understanding of the biophysical mechanisms underlying patch seal formation. Additionally, since the stretching of the cell membrane can be recorded simultaneously, the response of pressure sensitive ion channels to strain can be determined accurately. By comparison, both micro pipette and planar patch setups suffer from the fact that the cell protrusion into the patch orifice is typically in the plane normal to the optical (xy) plane, which make the determination of the shape of cellular protrusions into the patch channel difficult.

In one aspect, multiplexed acquisition of fluorescent and electrophysiology data, as provided for herein, opens up a host of high content experiments not currently possible for planar device geometries. An example is the correlation of dye intensity with electrical recording. Other experiments include Ca flux experiments, the use of pH sensitive dyes, fluorescent ion channel structure reporters or genetic expression markers.

In one embodiment, optical access to the trapping sites is beneficial in selecting the cells to be trapped. Under light microscopy, the healthiest cells can be individually selected to optimize experimental conditions. Under fluorescence microscopy, cells that have been fluorescently tagged can be individually selected from a suspension that may contain one or more cell types or conditions. Primary cell cultures often contain multiple cell types (e.g. neuronal cell cultures containing both astrocytes and neurons) and it is not always practical or feasible to pre-sort the cells prior to patching or electroporating. With microscopy and appropriate labeling of cells, if required, the desired cell type within a primary culture can be selected. Optical access to the trapping sites allows the trapping process to be easily automated using image analysis (object recognition) software and computer controlled pressure sources.

In a further aspect, the microfluidic arrays presented herein are suitable for high throughput electrophysiology. In one embodiment an automated patch clamp array can be used to record transmembrane currents form a large population of cells in response to a large number of compounds applied in fast succession. Increasing the numbers of both compounds applied to the same cell and cells patched simultaneously will result in an instrument capable of operation in the 1K-2K data point per day range for a fluidics-only system. Close proximity of patch sites and enclosure in a microfluidic channel result in dramatic reductions in reagent consumption and provide homogeneous concentrations across a population of patched cells. The interrogation of a large number of cells is useful for the systematic study of a large number of channel mutants.

In one embodiment, the microfluidic arrays described herein can be used along with robotic manipulation to increase throughput to the 20K-30K range, enabling electrophysiology as a primary screening tool for large compound libraries. A robotic fluid delivery and manipulation system can be employed for sample and reagent handling. Additionally, delivering a sample to the system can include pipetting of a fluid, for example by hand.

Microfluidic Patch Clamp System—Design and Device Fabrication

In general, in one aspect a method of fabrication of a disposable microfluidic component by standard soft lithography techniques using, for example, an SU8 mold is provided. The mold can be prepared using photolithography of SU8. First, a thin layer of SU8 (e.g., 2 µm) can be spun on to define the recording capillaries. Next, 40 µm high patterns can be added for wide connection regions using SU-8 negative photo resist. The mold can be used to form the PDMS device which subsequently can be bonded and connected to tubing through, for example, 0.5 mm punch holes [Seo]. The process has been previously described in detail in U.S. Provisional Application No. 60/710,305, filed on Aug. 21, 2005.

Another embodiment includes an increase in the trapping site density by about an order of magnitude, which correspondingly reduces the reagent volume requirements by an order of magnitude. The amount of reagent required for experiments on the 12 trapped cells is below 1 nl in the active device area. Because a number of data points are needed in order to provide robust statistics for ion channel characteristics, the extracellular application of the same reagent to all sites is a useful feature for pharmacology assays.

The density of such arrays is not limited by micromolding capability (features below 1 µm have been replicated by PDMS micromolding), but rather by cell size (e.g., HeLa diameters are 12-17 µm). Therefore, the 20 µm distance between trapping sites results in the highest patch clamp site density possible for patch clamp arrays. Because a number of cells can be observed simultaneously in the same microscope field of view, high density arrays are especially useful for correlating fluorescent cell measurements with patch recording from a large number of cells. The small reagent volume needed to apply a ligand to all 12 cells assures homogeneity in the ligand concentration for the whole cell population.

Figure 18:
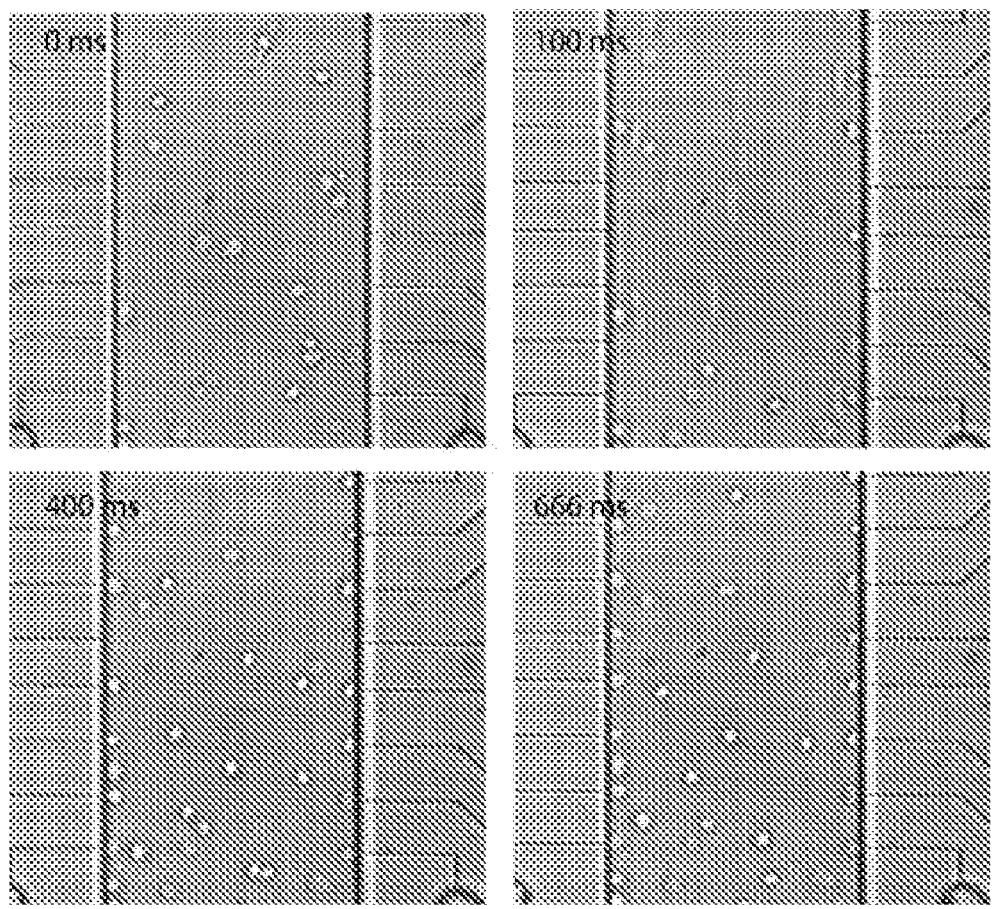
FIG. 18 shows sequential photomicrographs of cell trapping according to specific embodiments of the invention.

In one embodiment, a method of cell trapping is provided as follows. A variety of cell lines have been used to demonstrate trapping and for seal resistance experiments as described herein including the human tumor cell lines HeLa and SY5Y, the transformed human embryonic kidney cell line, HEK, and the Chinese hamster ovary cell line, CHO. Optionally, before introducing a cell suspension into the main chamber, the whole fluidic network is filled with an electrolyte solution. After dissociation by trypsin treatment, cells can be suspended in electrolyte solution and injected into the main channel. Gentle positive pressure (e.g., 1 psi) can then be applied to the patch channel while cells are loaded into the main fluidic channel in order to prevent contamination at the patch site. A cell can either be trapped randomly or selectively by controlling the flow through the main fluidic channel. A cell found within about 100-200 µm of the patch channel opening can be trapped within a 1 s time interval by applying negative pressure (e.g., 2-3 psi) to the recording capillary. FIG. 18 demonstrates simultaneous trapping of 15 HeLa cells by applying negative pressure (e.g., 2 psi) to the recording capillaries. In the example shown, trapping channels are separated by about 50 µm. Depending on the size of the cells to be trapped, the channels can be spaced closer or further apart, as desired. In one example, the channels are spaced less than 20 µm apart. After cell trapping, the negative pressure can be reduced and the cell is free to form a seal with the rim of the patch channel.

In another embodiment a method of assaying seal resistance and stability is provided as follows. Before cell trapping, the electrical connection between the reference Ag/AgCl electrode in the main channels and the patch electrode in the lateral patch channel can be confirmed by applying, for example, a 10 mV square pulse and recording the current response. A typical access resistance for the lateral recording capillary can be in the range of about 10-14 M$\Omega$. This may be at or above the access resistance of traditional micropipettes (e.g., 5 M$\Omega$), but can be lowered by reducing the length of the recording capillary. Sealing resistances can be recorded by applying a square voltage pulse of amplitude about 10 mV (e.g., 50 ms duration). The current response can be recorded using a standard patch-clamp amplifier (manufacturers: Axon Instruments, Foster City, Calif.; Dagan Corporation, Minneapolis, Minn.; Warner Instruments, Hamden, Conn.; HEKA Instruments Inc., Southboro, Mass.) and low-pass filtered at about 1 kHz. The current response presented contains no capacitance compensation. In one example the resistance of the open patch channel was measured to be about 14.4±3 M$\Omega$. For the specific channel geometry tested (4 µm×3.1 µm×200 µm), the conductivity of the electrolyte used ($\sigma$=1 S/m) yields a calculated resistance of 17 M$\Omega$, in reasonable agreement with the measurement. Patch clamp amplifier as used herein refers to any circuit capable of applying a voltage and measuring a current across a resistor that voltage is being delivered to. Such circuits may be purchased commercially (as mentioned above) or, alternatively, newly developed circuitry with similar function. In the context of patch clamp recording, the resistor may consist of a cell. In whole cell recording, the resistor may consist of a cell membrane.

When a square voltage pulse is applied to the system, capacitive coupling can lead to a current spike at the onset of the voltage application. Integrating spike currents gives an approximation to the charge stored in the capacitor by: q=∫I dt. Capacitance can then be calculated by using C=q/V. Low capacitance is important for the accurate recording to ion channel currents. Therefore, in one embodiment the device geometry is designed to minimizes capacitive coupling between the main chamber and the recording capillary. Device design, together with the low dielectric constant of PDMS, can result in very low capacitive coupling between the cell reservoir and the patch channel.

In one test study, capacitance measurements yielded values of 10±1 pF for connections between the device and the patch clamp amplifier input, but showed no further capacitance increase when the device itself was attached. It can be concluded that the device capacitance is within the measurement error, or $C_{dev} \leq 1$ pF. Calculations, using the device geometry and $\epsilon PDMS$=2.46 [Lin], yielded a predicted device capacitance $C_{dev}$=0.5 fF. By comparison, capacitances for micromachined patch clamp devices are 1 pF for glass substrates [Fertig], while micropipette capacitances are in the range of 2 pF to 20 pF, depending on the coating applied to the pipette exterior.

Cell trapping by suction was described previously. The current response from the cell exposed to a 10 mV/50 ms current pulse was used to calculate sealing resistance. Therefore, the sealing resistances values reported are always a measurement of sealing resistance in parallel with the membrane resistance of the cell. In the cell attached configuration, the cell's membrane resistance is high ($R_{cell} \approx 10$ G$\Omega$), and the smaller seal resistance dominates the measurement because $R_{seal} \approx 1$ G$\Omega$. However, in the whole cell configuration, the membrane patch inside the recording capillary is no longer intact so that the cell's membrane resistance decreases to $R_{cell} \approx 200$ M$\Omega$, and is dependent on ion channel conductivity. Sometimes during cell trapping the cell membrane patch breaks, leading directly to a whole cell configuration. All seal resistance measurements are taken for individual cells, independent of weather patch break has occurred or not. Therefore, while measurements above 200 M$\Omega$ are necessarily in cell-attached mode, lower seal measurements may be in either cell attached or whole cell mode.

In one embodiment, the microfluidics based micro-array includes a lateral patch geometry [Seo]. Preliminary results with the initial design generated cell attached seals of 140±40 M$\Omega$ [Seo], which are too low for whole cell seals and accurate whole cell recording. The maximal seal resistance obtained was 200 M$\Omega$. The seals reported are typically for the first cell trapped on the recording capillary. By applying positive pressure to the patch clamp channel, the trapped cell can be expelled from the channel. After the cell was expelled, the current response returned to that of the open channel. Subsequent cell trapping in the same patch pore typically resulted in lower seal resistances, presumably due to contamination at the opening of the recording capillary.

Figure 9:
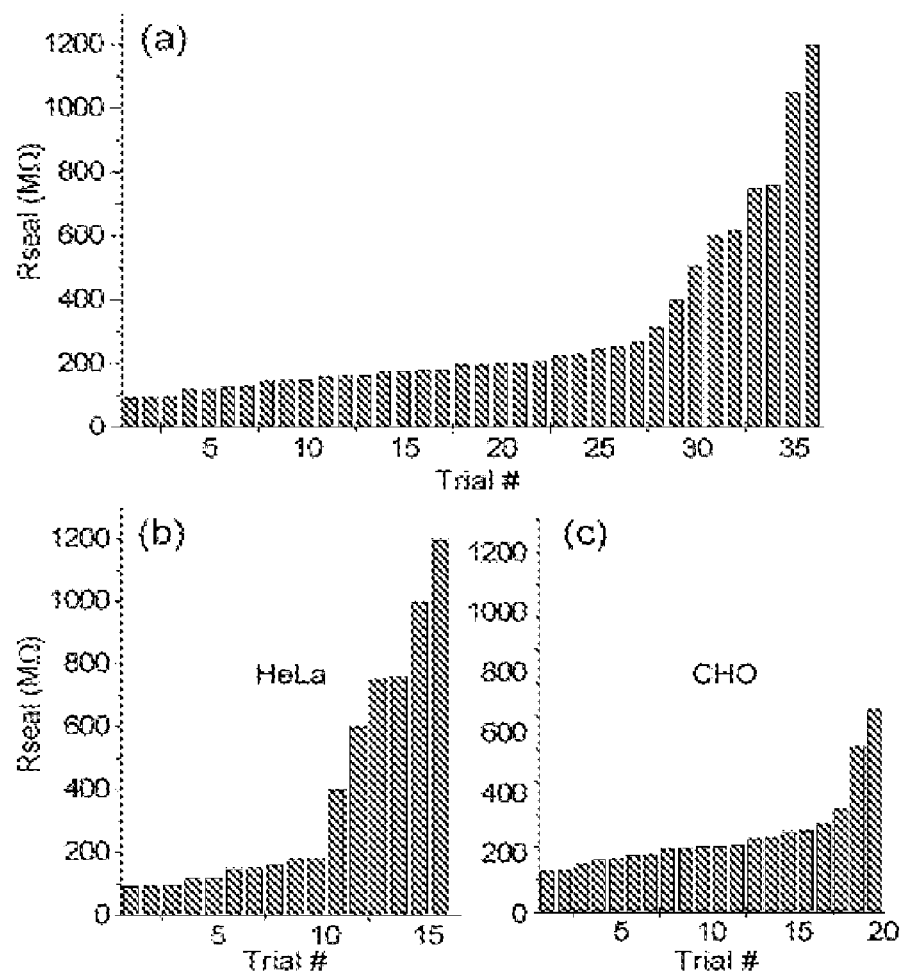
FIGS. 9A-C are graphs illustrating example seal resistance measurements obtained from different cell types.

In another embodiment, a modified technique is used to bond the molded devices to the flat PDMS substrate. While oxygen plasma bonding can be used initially, using a partial cure bonding doubles the seal resistance to a level sufficient for whole cell recording. The change can be attributed to superior sealing of the recording capillary edges and a more rounded geometry at the bottom corners of the patch orifice. A sample set of sealing resistance measurements for partial cure bonded devices are presented in FIG. 9. There is a difference between seals obtained with HeLa cells (FIG. 9 panel B) and CHO (FIG. 9 panel C). While the average sealing resistance was similar, only HeLa cells exhibited some sealing resistance values in the G$\Omega$ range. Overall, recorded sealing resistances were 150 M$\Omega$ to 1 G$\Omega$, with 20% of the seals greater than 250 M$\Omega$ (FIG. 9 panel A).

Another important seal quality is stability over time. Pipette based patch clamp recording systems are susceptible to loss of seal integrity due to mechanical vibration of the pipette tip. Careful anchoring of the pipette manipulators, which position the pipette against the cell membrane, and expensive vibration isolation tables are among the precautions necessary for successful patch clamp recording. Even with these preparations, whole cell seals do not last more than an hour under ideal circumstances, and more commonly last ten to fifteen minutes. In the PDMS device described herein, each cell can become integrated into a recording capillary without the aid of external positioning devices. As a result, the effects of ambient vibration on seal integrity are minimized.

Figure 10:
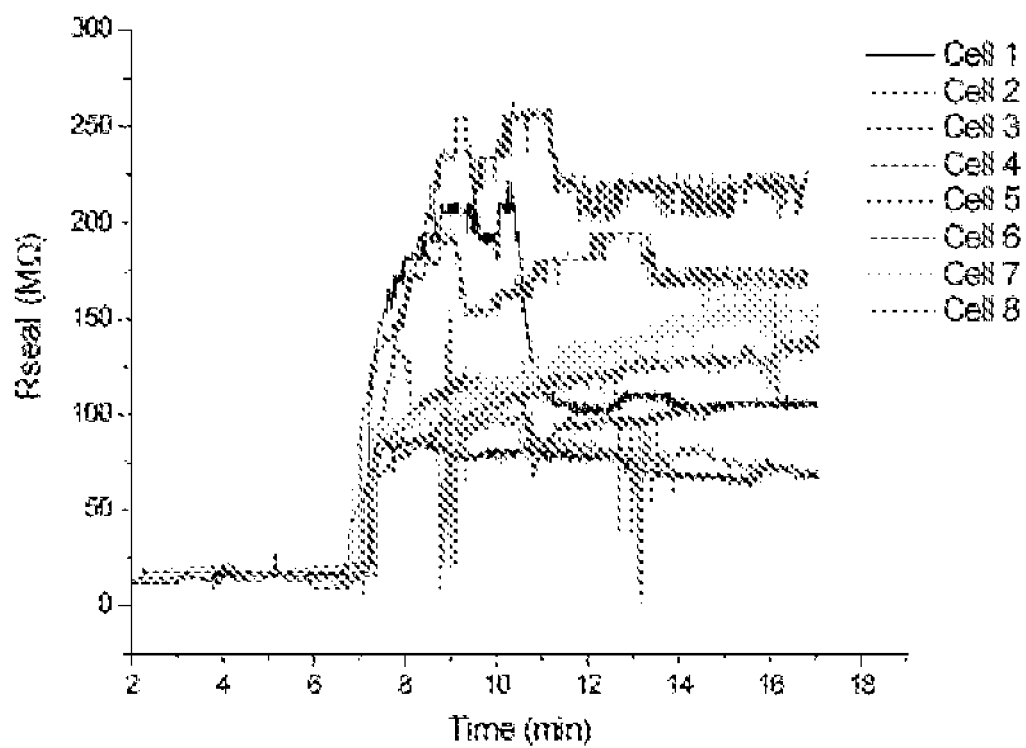
FIG. 10 is a graph illustrating example seal resistance measurements.

As with all the data presented, no vibration isolation equipment was used with the PDMS device. Whole cell configuration was confirmed by measuring cell capacitance. Seals for the three CHO cells tested for longevity lasted 18-45 min. A number of shorter experiments show the timescale of sealing. (FIG. 10) In general, seals typically lasted 20-40 min, after which seal resistance drops to values below 50 MΩ.

Figure 11:
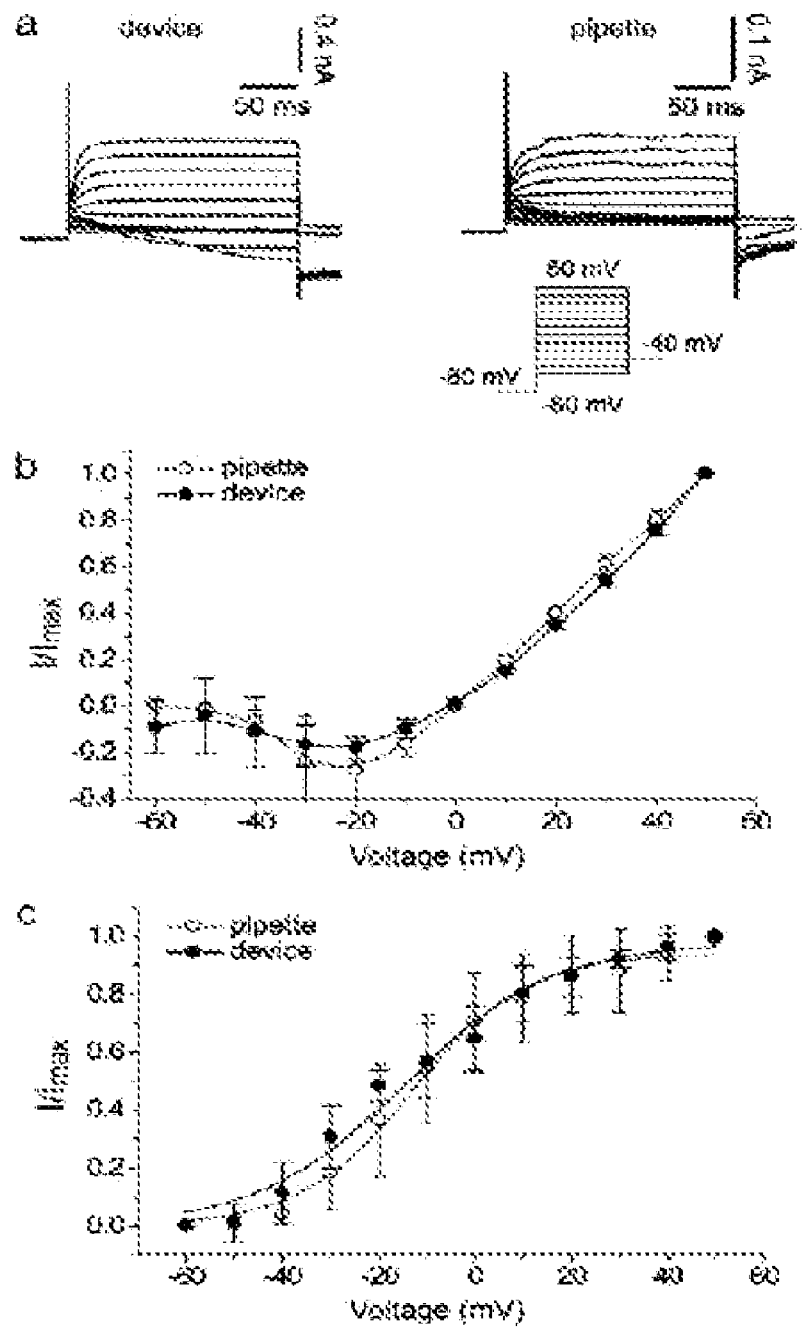
FIGS. 11A-C are graphs illustrating whole cell activation using one embodiment of the invention compared to traditional pipette-based patch clamp technique.

In one example the microfluidics based micro-array produced results comparable to pipette-based electrophysiology (FIG. 11). In preliminary work it has been demonstrated that the patch array described herein is capable of recording activation of the voltage gated potassium channel Kv2.1, which was stably expressed in mammalian CHO cells. Activation data corresponded well with that measured by traditional pipette based technique. Cell trapping can be confirmed by light microscopy. In one embodiment the cells are placed in suspension in the central chamber and are sequentially brought to the patch pores by applying negative pressure of about 28 kPa to the patch capillaries.

In another embodiment, whole cell patch experiments can be performed by first filling the whole device with electrolyte solution and recording open channel resistance which can be about 10-14 MΩ. Negative pressure can be used to position the cell at the capillary orifice, after which negative pressure is removed to allow for seal formation. Application of a quick pressure pulse then leads to membrane break and electrode access to the cytoplasm. Whole cell seals can be confirmed by cell capacitance, which, for example, is about 7-10 pF for CHO cells in suspension. Whole cell seals are judged to be satisfactory if greater than about 100 MΩ. Occasionally the cell membrane breaks during cell trapping at the patch channel opening, leading to a whole cell configuration directly.

In one embodiment, activation currents can be recorded in whole cell voltage clamp mode from, for example, CHO cells stably expressing the potassium channel Kv2.1. Where seals are not in the gigaohm range, it may be necessary to perform leak subtraction. Selection bias can be removed by processing all data through the same leak subtraction routines. Since the ion channel Kv2.1 is closed at negative bias voltages, leak resistance can be measured by recording the current response at a negative hold voltage of, for example, about −80 mV. Steady-state activation currents can be recorded, for example, about 20 ms after the start of the voltage pulse.

Validation of device performance can include a direct comparison between recordings of Kv2.1 using the device and pipette-based patch recordings. As shown in FIG. 11, in one experiment activation current-voltage curves and tail current were recorded using both techniques. Cells were obtained from the same CHO cell line and recording was performed using identical protocols and solutions. The current-voltage curves (FIG. 11 panel B) were obtained from data 200 ms into the depolarizing pulse, and tail currents were obtained 0.6 ms after repolarization to −40 mV. All data were leak subtracted as described [Ionescu-Zanetti]. The traditional patch data were also automatically leak subtracted, although the effect on the results was minimal. The only protocol difference was that the PDMS device used recently trypsinized cells in suspension while traditional patch clamp approaches cultured cells adherent to a coverslip. For the PDMS device, in cell-attached mode the seal resistance was 150 MΩ to 1.2 GΩ, with 20% of the seals greater than 250 MΩ. In whole cell mode the cells had a recorded seal resistance of 100-250 MΩ at −80 mV. FIG. 11 shows a comparison of Kv2.1 whole cell activation with both the PDMS device and traditional pipette-based patch clamp technique. The holding potential was set to −80 mV. The cell membrane potential was depolarized from −60 mV to +50 mV in 10 mV increments for 260 ms, followed by a repolarization to −40 mV for tail current recording. In panel A of FIG. 11, representative recordings from the PDMS device (left) and a patch pipette (right) are shown. All currents were leak subtracted. In panel B of FIG. 11, steady state activation current is shown as recorded with the PDMS device (filled circles, n=4) and the patch pipette (open circles, n=4). Panel C of FIG. 11 shows a comparison of normalized tail currents at Vm=−40 mV. Recordings from the PDMS device were made without use of a vibration isolation table.

Channel activity recorded with the PDMS device shows channel closure at voltages below −20 mV, as well as activation and linear increase at positive voltage (FIG. 11 panel B). Analysis of the tail currents also reveals good agreement between recordings from the PDMS device and traditional patch clamp techniques (FIG. 11 panel C). A Boltzmann fit to the tail current data yields a 50% activation voltage V50%=−12.9±1.2 mV and slope factor k=11.9±1.0 mV for the pipette data. These data correspond well to V50%=−13.4±2.3 mV and k=14.8±1.9 mV for the PDMS device. This data indicates that the devices described herein can perform well for recording whole cell currents in a regime where the peak currents recorded are in the range of 200 pA (for a bias of 50 mV). For significantly lower currents (I<50 pA), the sealing resistance will play a larger role, and further improvements in sealing may become necessary for accurate recording.

An important test of channel activity is the ability to block its response with known antagonists. Such experiments will be a component for large scale screening of pharmacological compounds. Kv2.1 channels are known to be blocked by TEA [Immke], and this reagent was introduced into the main chamber between two sets of activation recordings. Perfusing the main chamber with TEA is equivalent to changing the perfusate in a patch clamp tissue bath, and would be the mode of extracellular reagent delivery to patched cells. Current response from the same cell both before and after introduction of the K blocker TEA the showed the successful suppression of K+ currents [Ionescu-Zanetti]. It is envisioned that changes in current due to the fast application of reagents to the patch cell, can be observed as described herein.

Figure 12:
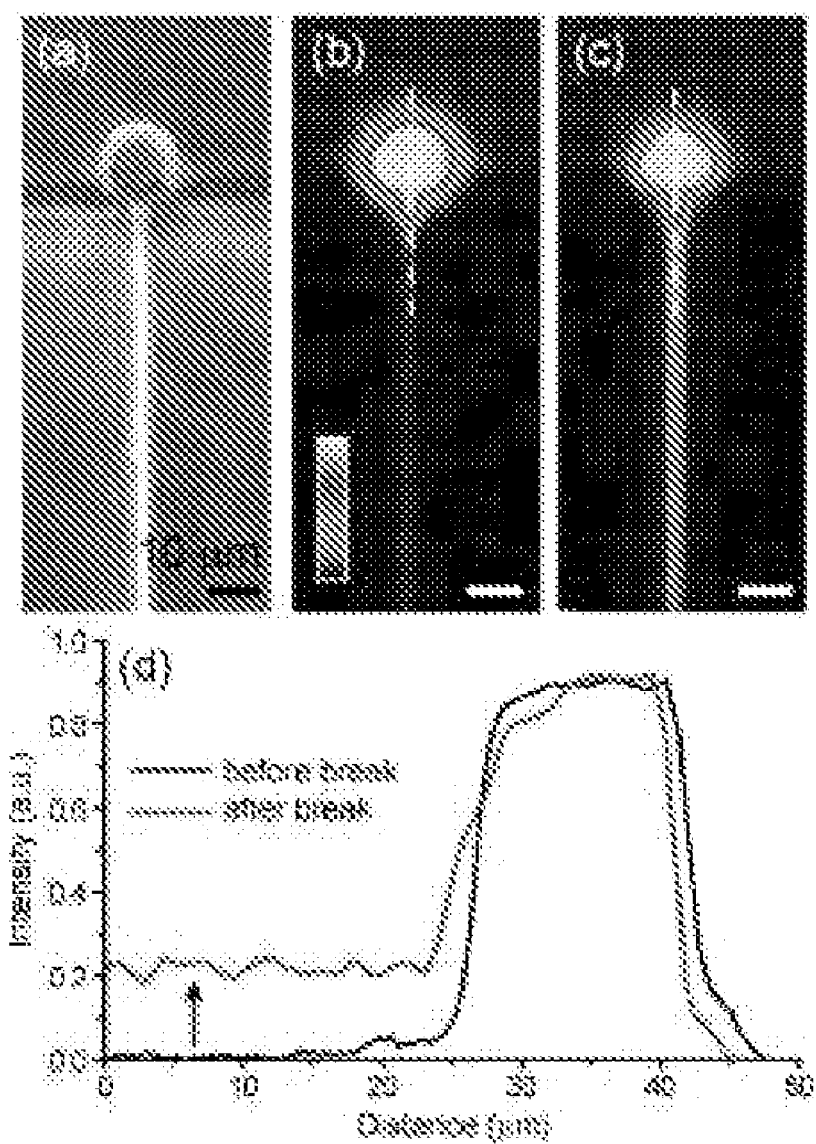
FIGS. 12A-D are photomicrographs and a graph showing dye intensities associated with trapped cells using one embodiment of the invention.

In one embodiment, microscopy is applied to the patched cells using established microscopy methods for obtaining complementary information to current recordings across the patched pore. Enabled by the fact that the device may use a glass cover slip bottom, it is possible to measure both changes in cell morphology and membrane integrity. In these examples, cells were prepared for imaging as follows: HeLa cells are cultured in a dish and trypsinized into a cell suspension, after which the cytoplasm is labeled with the dye Calcein. The suspension is introduced into the device and individual cells are drawn into patch channels by the application of negative pressure. By way of example, bright field (phrase contrast in panel A) and fluorescence images (panels B and C) of a HeLa cell trapped at the patch orifice are shown in FIG. 12. Upon trapping, the cell membrane advances for about 5 μm inside the capillary (FIG. 12B). An additional negative pressure pulse is then used to rupture the membrane patch inside the capillary, leading to a whole cell configuration (FIG. 12C). By plotting the fluorescent intensity as a function of distance along the capillary axis (dotted lines, FIG. 12B-C), both the distance that the cell protrudes inside the capillary and the amount of cytoplasmic dye leak into the capillary can be quantified. The increase in dye intensity inside the capillary is indicated by the arrow in FIG. 12D.

Fabrication methods for particular embodiments of microfluidic devices integrated with a standardized wellplate format are as follows:

In one embodiment, a manufacturing process is provided to integrate electrophysiology-ready devices with standard 96-well plates (or other plates as described herein) that are compatible with robotic plate handling and fluid delivery. Device assembly time should be below 30 min and have a high yield of above 90% (channels connected and pressure sealed). Access resistance for all channels should be below 5 MΩ. In a particular embodiment mask designs are adapted such that channel inputs/outputs (e.g., inlets/outlets) are aligned with the positions of the well plates. Punch holes provide connectivity between the well volume and the microfluidic device. To optimize manufacturability, an automated hole punching system can be employed.

Multi-well plates can be made from, for example a polymer, a plastic (e.g., polypropylene or polystyrene), glass, ceramic or metal.

In another embodiment, the efficiency of sealing between PDMS devices and the polystyrene can be assessed by verifying sealing under pressure and electrical connectivity. Fluid can be driven by applying pressure to the well plate volume via an external interface. Bond integrity can be tested by applying increasing pressure until bonds fail. The bonding process can be optimized to a level where all wells can withstand a pressure of, for example +/−10 PSI, necessary for cell trapping and compound introduction into the test area.

In one embodiment the access resistance of channels connecting each well to the measurement region is <5 MΩ, which is ideal for accurate ion channel recording.

In another embodiment the microfluidic devices are capable of obtaining whole cell configuration and perform ion channel recording. The results should correlate with pipette based recordings to within one standard deviation. In this embodiment a mechanical device can provide connectivity to the well plate integrated device. Pressure connectivity can be achieved using a press-fit gasket system, while electrical connectivity can be achieved using electrodes immersed into the recording capillary input wells. Pressures up to 10 PSI can be applied, while AgCl electrodes used can be conditioned in order to minimize offset potentials during electrophysiological recording. Offset potentials below 100 mV will be considered adequate. It is envisioned that access resistance to the cell can be reduced to a level below 15 MΩ. Ion channel recordings can be obtained and compared to pipette based recording of the same cell line. A measure of success will be correlation to standard recording to within 1 standard deviation for whole cell currents above 50 pA. This will demonstrate the basic ability of the devices to perform whole cell recording in cell lines transfected with an ion channel of interest, thus useful, for example, for drug discovery applications.

Automated Measurements in a Medium to High Throughput Format

In one embodiment, an interface is provided that is capable of applying pressure and measuring currents through recording capillaries under computer control. The system can automatically trap cells at, for example, n=15 sites in less than 1 minute (FIG. 18). In a particular embodiment cell trapping at the patch orifice can be achieved through the application of negative pressure to the input of the recording capillary. The automated system employs a pressure regulator and a bank of solenoid valves under computer control in order to apply a desired trapping pressure. Cells can be observed optically under an inverted microscope. After introducing the cell suspension into the main chamber and pressure application, trapping efficiency can be characterized by measuring the average time from negative pressure application to a cell trapping event and the probability of breaking the membrane patch on trapping. Trapping time and rupture probability can be measured as a function of trapping pressure. These measures can also depend on cell density in suspension, so the cell density can be kept constant by using a hemocytometer before each experiment. Next, the two parameters will be measured for an ideal trapping pressure, now as a function of cell density of the cell suspension.

Preliminary data indicate that individual cells can be moved to a trapping site by the application of negative pressure in the range of about 1-5 psi to the recording capillary. It is envisioned that the trapping time required can be minimized, while making sure that the cell patch inside the recording capillary does not rupture upon trapping. Minimal trapping times are desirable for high speed cell trapping, as well as to minimize the contamination of the inner surface of the capillary by debris from the suspension media. It is also envisioned that higher pressures can result in faster trapping times, but also increase the probability of a membrane break on trapping. In one embodiment, trapping times below 1 minute for n=15 trapping sites, while minimizing the membrane break probability to below 20% are achieved. Membrane integrity can be monitored using the cytoplasmic dye calcein as described herein. A fluorescence equipped microscope can therefore be used for measuring both time to trap and cell integrity.

Figure 13:
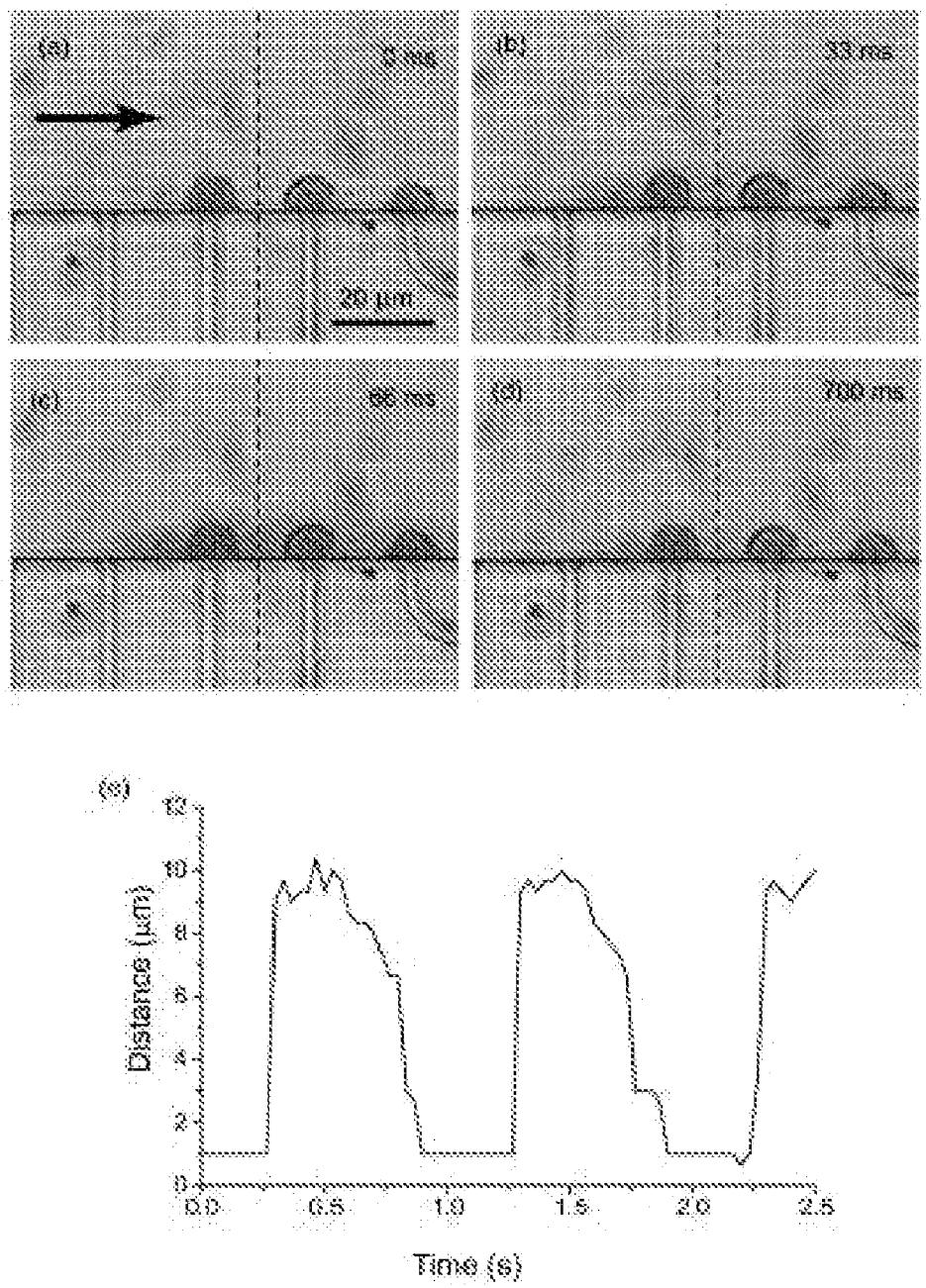
FIGS. 13A-E are sequential photomicrographs and a graph showing pulsed perfusion of cells using one embodiment of the invention.

In another embodiment microfluidic designs provide for very fast exchange (e.g., t<5 ms) of multiple compounds in the extracellular space and verification of delivery using, for example, a fluorescent readout (FIG. 13). A pharmacological data point is defined as measuring the response of one patched cell to one applied compound. Therefore, besides cell trapping speed, the ability to apply compounds quickly to the extracellular space is a critical determinant of throughput. In a particular embodiment, compound injection channels capable of delivering a molecule of interest to 6 or more trapped cells simultaneously are provided. In another embodiment, the channels are capable of delivering to 60 or more trapped cells simultaneously. In another embodiment, the channels are capable of delivering to 600 or more trapped cells simultaneously. A continuous flow in the main channel enables compound removal as it is washed away by extracellular buffer solution. As shown in FIG. 13, preliminary experiments show that a compound can be applied within a time below 30 ms and removed within 150 ms. Pulsed Perfusion of Single Cells is shown in FIG. 13. Panels A-D of FIG. 13 show a chronological sequence of application and removal of red dye around trapped single cells for 1 Hz pulsed flow. A constant flow (left to right) was imposed in the main chamber, while another small channel upstream was used as an injection port. FIG. 13 panel E shows a graph of the distance between the dye front and the main chamber edge as a function of time. Reagent application was below 30 ms (frame rate).

In one embodiment, fluorescently labeled compounds are applied sequentially to a set of trapped cells. In another embodiment compounds are introduced to the trapped cells with an on time below 5 ms. Throughput can be set by the time required to trap cells (e.g., 3 min), achieve sealing and whole cell configuration (e.g., 3 min) and the time to apply eight compounds. When 6 trapped cells are tested, there will be 36 data points (6 compounds×6 cells) for an experimental time of, for example, 10 minutes. As such throughput for a 10 hour work day should be 2160 data points. In one embodiment the throughput for cell trapping/compound application is above 1000 data pts/day. Where increased numbers of compounds and cells are tested, corresponding increases in data points can be realized. In another embodiment the throughput for cell trapping/compound application is above 3000 data pts/day. In a further embodiment the throughput for cell trapping/compound application is above 30,000 data pts/day.

Optimized Parameters for High Yield Patch Seals

In one embodiment, the dynamics of seal formation are determined, and a simple model for the biophysics of seal formation is developed. Considerations include: characterizing cell protrusion length inside the recording capillary in response to applied negative pressure and simultaneously measuring changes in sealing resistance and correlate sealing with both time and the amount of protrusion into the capillary. This data can be used to optimize trapping pressure application.

In one embodiment, cell shape changes resulting from the application of negative pressure to the patch channel can be recorded by using bright field or fluorescent imaging (see FIG. 12). After compiling data on cell deformation in response to a range of applied trapping pressures (e.g., 0-5 psi), seal resistances can also be recorded in conjunction with deformation measurements. The data can be obtained by time lapse image acquisition of the cells on the patch array; imaging can be initiated simultaneously with the recording of seal resistance over time (see for example FIG. 12).

In a particular embodiment, if it is found that the seal resistance is proportional to the distance that the cell protrudes into the recording capillary, it can be concluded that the seal formation occurs all along the capillary wall. However, if the protrusion length does not scale with seal resistance, this result would indicate that seal formation is dominated by adhesion at the pore opening and not inside the channel.

In another embodiment, an idealized model of capillary shape, as well as cell protrusion shape can be used in order to make predictions as to the sealing resistance dependence on cell shape. For example, if it is assumed a cylindrical capillary and a cylindrical cell protrusion into the capillary over a length of 10 µm, it is possible to calculate the average distance between the cell membrane edge and the capillary wall. If it is assumed that a sealing resistance of 200 MΩ is due to the resistance along the length of the protrusion, a distance of approximately 5 nm between the cell membrane and capillary walls can be concluded. Extensions of such calculations can be used to understand the process of seal formation and aid in intelligent design of future devices.

In one embodiment, the geometry of the patch orifice and recording capillary is optimized in order to maximize the probability of giga-seal formation. The shape can be characterized by roundness (radius of curvature), and size (height and width). Seal resistances can be measured and correlated with the parameters enumerated above.

In a particular embodiment, fabrication is achieved by a two mask process; one mask for the definition of small patch channels (Si etch or low height SU8 pattern) and another for the definition of large fluidic channels needed for cell suspension delivery and to connect the patch pore to the macro scale interface (SU8 pattern). These features are defined as raised on the wafer and transfer to trenches when PDMS is molded by using the Si wafer as a mold. The resulting geometry can be quantified by scanning electron microscopy (SEM). Patch channel dimensions have been successfully fabricated by the present protocol down to dimensions of 2×2 µm. By comparison, the channels used in proof of concept work have dimensions of 3×4 µm. Channel geometry can be altered by either changing the geometry of the wafer mold, or altering the protocol for bonding the device to the bottom substrate. Resulting geometries can be evaluated by performing systematic seal resistance measurements.

In one embodiment, the size of the recording capillary is about 3.1×4 µm. In a particular embodiment the leak currents can be proportional to the circumference of the recording capillary, meaning that, for example, for a 2×2 µm capillary an increase in sealing resistance is attainable. In a related embodiment capillaries of reduced length and/or an adjacent trapping channels can be used in order to facilitate trapping for small channels.

The efficient bonding of the molded device to the bottom substrate is another fabrication step whose optimization is likely to lead to improvements in seal resistance. In one embodiment oxygen plasma bonding is used to partial cure bonding. Such and approach results in a dramatic increase in seal resistance, by about a factor of two. In another embodiment the curedness of the bottom substrate, as well as curing method before bonding can be varied in order to optimize the device geometry, as well as the resultant seal resistance.

In another embodiment, sealing resistance can be controlled by varying the elastic properties and/or surface hydrophobicity of the recording capillary material. In one embodiment average whole cell seals of 500 MΩ can be achieved. The Young's modulus of PMDS is known to be dependent on the mixing ratio of base to curing agent. Accordingly, desired property changes can be measured by a standard macroscopic apparatus for measuring deformation as a function of applied force for a PMDS strip of known dimensions. The typical ratio is 1:10 (curing agent: base) to achieve PDMS with a maximal number of side chain cross linking points per monomer molecule. It is envisioned that this ratio can be varied from 1:5 to 1:100 followed by measurements of the effect on Young's modulus. As such, in one embodiment devices of varying Young's modulus can be tested for electrical sealing with a sufficient number of cells (e.g., 10-20 cells per concentration point) in order to determine the ideal conditions for sealing.

Material properties are well known to be critical for the establishment of an electrical seal between the cell membrane and the patch clamp recording capillary. In one embodiment the material properties can be varied in a methodical fashion in order to optimize seal formation. For example, in one embodiment the amount of cross linking between monomer chains in the PDMS matrix can be varied by changing the amount of available curing agent. For current devices, for example, the curing agent can be mixed such that all the available cross linking sites are bonded to each other. Lowering the percentage of cross linking sites will lower the Young's modulus of the device material. This relationship can be tested by macro scale experiments.

It is further envisioned that the surface of the recording capillary can conform better to the shape of the trapped cell, increasing the sealing resistance. This can be tested by measuring sealing resistance for different mixing ratios. In addition to changing Young's modulus, other possible mechanism for the dependence of the electrical seal on cross linking efficiency include the alteration of PDMS surface properties or surface roughness.

Recording of Dose-Response Relationships Using Known Ion Channel Modulators: Extracellular and Intracellular Perfusion In one embodiment, fast extracellular solution exchange can be used during ion channel recording at a set voltage to obtain the same dose-response relationship in less than one minute. For pharmacology studies, dose response curves are essential in order to determine the concentration dependence of current suppression. In one embodiment varying concentrations of the channel blocker TEA can be introduced into the main chamber by introducing different concentration sequentially in the central channel. Current voltage relationships can be measured for each concentration point. In preliminary experiments the ability of the patch array to achieve extracellular solution exchange, and measure the blocking of the voltage gated channels (Kv2.1) by a high concentration (10 mM) of the potassium channel blocker TEA has been shown [Ionescu-Zanetti]. The aim of the experiment was to measure dose-response relationships for the same ion channel-antagonist system. In one embodiment an accurate determination of the antagonist concentration needed for a partial block of the channel population is provided. In this way the device can be used to characterize pharmacological agents, where the concentration dependence of blocking efficiency is essential.

In another embodiment, a hERG expressing cell line can be used to obtain IC50 values for a known blocking compound (e.g., Dofetilide) and can be assessed following a protocol equivalent to the one described above for TEA blocking of Kv2.1.

In order to speed-up data acquisition, as well as recording of fast activating ligand gated channels, in one embodiment, fast fluidic exchange is provided. In this embodiment, the cell membrane can be kept at a constant positive bias (e.g., V=60 mV), a regime in which high levels of ion channel currents can be recorded. Using the fast extracellular solution exchange scheme described above, different concentrations of the test compound can be introduced in fast succession. The cell line/ion channel/blocker system used can be identical with the two experimental systems described herein. The changes in current in response to introduction of various blocker concentrations can be recorded as a function of time. By comparing the percent block at a set voltage clamp value, it is possible to construct a set of IC50 experiments over 6 orders of magnitude in concentration. The results can be used to confirm the minimum time required for efficient extracellular media exchange while performing simultaneous patch clamp recording. Additionally, the results can be compared to the relatively slower exchange experiments described, and validation can be determined by good agreement between the two methods.

Figure 14:
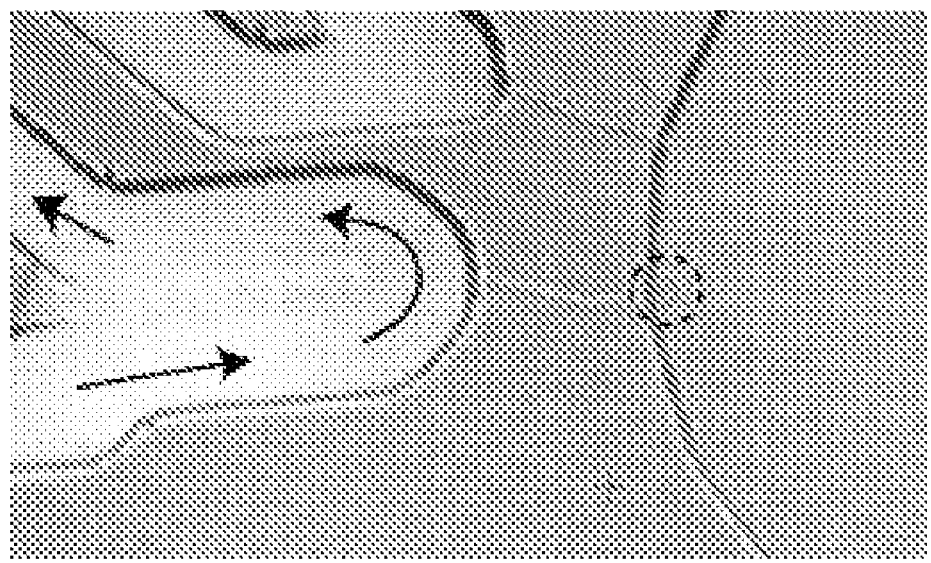
FIG. 14 is a photomicrograph showing a backside perfusion design of one embodiment of the invention.

Fast Intracellular Solution Exchange in Conjunction with Ion Channel Recording in the Whole Cell Configuration In one embodiment, the dose-response relationship for intracellular hERG channel blockers can be obtained. The ability to perform fast intracellular solution exchange is unique to a microfluidic integrated patch tool. As shown in FIG. 14, in a particular embodiment, chip designs including a backside perfusion channel amenable to cell trapping are provided. FIG. 14 illustrates backside perfusion wherein two patch channels are fabricated with a backside perfusion design. Using the channel design shown, intracellular solution can be exchange quickly by applying differential pressure to the access channels (see FIG. 14 arrows). One embodiment uses a CHO cell line expressing the hERG ion channel, which is essential in cardiac safety testing of drug compounds. Since most hERG blocker compounds have intracellular binding sites, the time to deliver drugs to the cytoplasm can be reduced significantly by this design from about 15-20 min currently to below 1 min for intracellular delivery. In one embodiment the delivery time is below 15 min. In another embodiment the delivery time is below 5 min. In a further embodiment the delivery time is below 30 seconds. In another embodiment the delivery time is below 5 seconds. Delivery times can first be first characterized by using fluorescent compounds and measuring brightness increase in the cytoplasm. After a baseline measurement of hERG current, increasing concentrations of the blocker compound can be introduced using the backside perfusion channel. Currents can be recorded from the same patched cell in response to increasing blocker concentrations (4 concentration points).

Interface for Electrical and Pneumatic Control of a Microfluidic Device

As illustrated in FIG. 15, in one embodiment, an easy to use, inexpensive microfluidic interface system 200 is provided. System 200 can include an interface 201 and a microfluidic device 202. System 200 enables automatic cell trapping and electrical measurements with minimal setup and minimal manual control makes data acquisition not only easier, but more reliable. Results are therefore more reproducible because parameters such as trapping pressure are well controlled. As shown in FIG. 15C, in one embodiment the microfluidic device 202 can include base 203, substrate 205 (e.g., microfluidic chips), and a plate 207 (e.g., a 96-well microplate). Substrate 205 can include one or more reservoir 219 and perfusion channels 215, which are shown in this example as backside perfusion channels (see FIG. 15C inset). Microfluidic channels in the substrate 205 can be used to trap cells 217 (see FIG. 15C inset). FIG. 15B is a bottom view of microfluidic device 202, showing in this example the substrate 205 bonded to the plate 207 and illustrating a clear optical viewing path through the substrate.

In one embodiment, the substrate can be bonded to a microplate with the channels facing up (thereby eliminating the need for punching through holes and for bonding an additional layer onto the channels). In one embodiment, an intermediate substrate is bonded in between the microplate and the microfluidic device (substrate). The intermediate substrate can be a layer that is, for example, a sheet of polymer such as silicone, 0.010-0.200 inches thick. In one embodiment, the intermediate layer has adhesive applied to the side that contacts the microplate. In another embodiment, the microfluidic layer is plasma bonded to the microplate.

As further shown in FIG. 15C, interface 201 can include a manifold 209, PCB board 211 and pressure interface box 213. In one embodiment, the pressure connects on the manifold are connected to the side ports via tubing.

In another embodiment, the box itself is machined to include air passages to connect the pressure ports on the bottom of the manifold (209) to the sides of the same part. The channels may first be machined as trenches in a first part (250), and then bonded to a second part (250) with holes disposed into a planar substrate in order to close off the trenches and form a fully assembled manifold (FIG. 15B)

Any one of such manifold designs may be used to form a pressure seal with the upper plate of the microfluidic devices integrated with reservoirs. In one set of embodiments, the pressure seal is formed via a deformable gasket material that is either attached to the interface or simply placed between the interface and the upper plate structure (FIG. 15B).

One manner of forming such a seal is to apply downward mechanical pressure on top of the interface with respect to the plate such that a deformation of the gasket is achieved. Another manner of forming a pressure seal is to apply a negative pressure in the space between contact points that define the edges of the fluid reservoirs. Such negative pressure will cause deformation of the gasket and sealing against the plate (FIG. 153).

In one embodiment plate 207 is a plate including from about 1 to 100 wells. In another embodiment plate 207 is a plate including from about 100 to 2000 wells. In one embodiment plate 207 is a plate including over 2000 wells. In further embodiments, plate 207 is a plate including substantially six (6), twelve (12), forty-eight (48), ninety-six (96), 384 or 1536 wells. FIG. 15A is a side view of system 200 and shows how the interface 201 can be aligned and easily connected with the microfluidic device 202.

In one embodiment, the interface is adapted to allow light to pass through from the top to the microfluidic device (configuration not shown).

In another embodiment, the interface provides only pressure connections, but no electrical connections.

Figure 41:
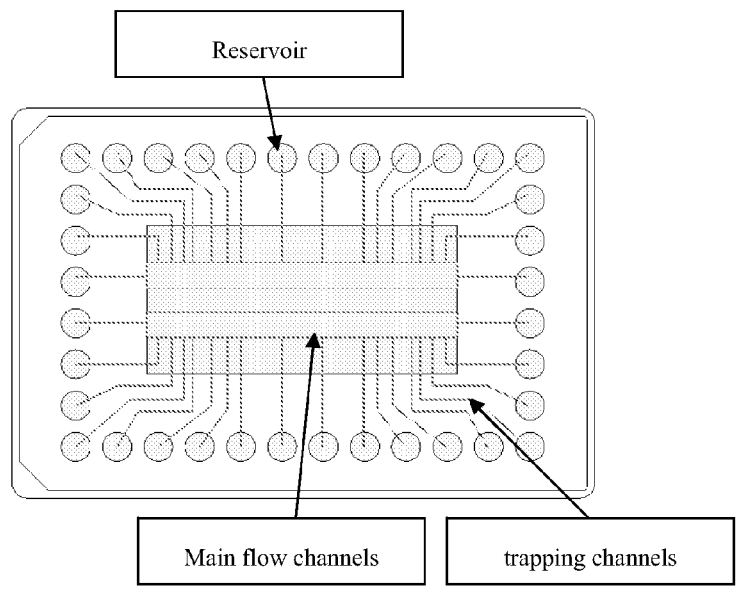
FIG. 41 shows an alternative microfluidic device according to specific embodiments of the invention.

As shown in FIG. 41, in one embodiment a central region of the plate can be a substantially bottomless microplate having an open region. The open region of the plate can be in the center of the plate or positioned anywhere desired on the plate. The open region can be regular or irregularly shaped. In the example shown in FIG. 41, the opening is rectangular-shaped and centered in the plate. Fabrication of the plate, for example, by injection molding, can include any desired size, number and arrangement of traditional microplate openings, for example in an arrangement surrounding the open region (see FIG. 41). In the embodiment shown in FIG. 41, an optically clear microfluidic device is bonded beneath the plastic upper structure of a plate having a central open region and traditional microplate openings that can act as reservoirs or wells. The wells can be fluidically coupled to main flow channels on the microfluidic device as indicated. In this arrangement, particles (e.g., cells) within the main flow channels can be viewed using an either an inverted microscope or an upright microscope. The microfluidic device can be bonded to the microplate in a "channel up" or "channel down" configuration. If the channels are bonded in an up configuration, a glass cover slide can be mounted in between the microplate and the microfluidic layer, with holes created in the glass to correspond to the well positions. If the channels are mounted in a "channel down" configuration, holes can be punched in the microfluidic layer to correspond to the well positions, and a solid piece of glass can be mounted to the channel side to close off the channels.

In the resulting system, a central opening can be large enough to allow a microscope objective to be placed adjacent to the region of interest (i.e. viewing window where the cells are trapped), and the objective can optionally be placed in an upright or an inverted position. The microfluidic device can be made thin enough such that the same plate can be viewed from top or bottom, or the microfluidic device can be made for a pre-disposed viewing orientation (i.e. an upright microfluidic device or an inverted microfluidic device) but the interface could remain the same.

The interface for this microfluidic device and plate combination could be similar in nature to interface described herein, although a central aperture in the interface could be created that is large enough to allow the microscope objective to enter from the top. Cutouts could be applied to the printed circuit board of the interface as well as any other components that may be obstructing optical viewing.

In one embodiment, the system setup effectively controls air bubbles, and consequently, prevents electrical disconnects and damage to cells in the channel due to the passage of air bubbles. The proprietary hollow Ag/AgCl electrodes that connect the microfluidic chip devices both electrically (connected to a printed circuit board) and fluidically sit in the 96 wells (not shown). So long as there is conductive solution in the wells, there is electrical connection. Because the electrodes are hollow, they also serve as the conduits for pressure application to the chip devices. The advantage of hollow sectioned electrodes is that they can provide pressure connectivity without aspiration of the fluid into the interface. In one embodiment, the electrodes are generally cylindrical and can be mounted in an array on a printed circuit board which provides electrical connections to a patch clamp amplifier. Tubing can be fitted over the top of the generally cylindrical electrodes, with the other end of said tubing connected to a means for pressure control. In another embodiment, the portion of the generally cylindrical electrode that sits in the fluidic well can be sectioned so as not to create a suction of fluid when negative pressure is applied to the well through the generally cylindrical electrode.

The pressure control box 213 as shown in FIG. 15 may be fabricated from anodized aluminum, which will serve as a faraday cage, eliminating the need for a large microscope-encasing faraday cage typical of electrophysiology setups. In addition, the pressure control box 213 can include solenoid valves (not shown). In this way, through control of the valves, pressure can be set to the channels either individually or simultaneously.

In one embodiment, a hole on the top of the pressure box can admit a light-path for optical access. This arrangement provides for optical monitoring without the need for a scanning stage.

Figure 16:
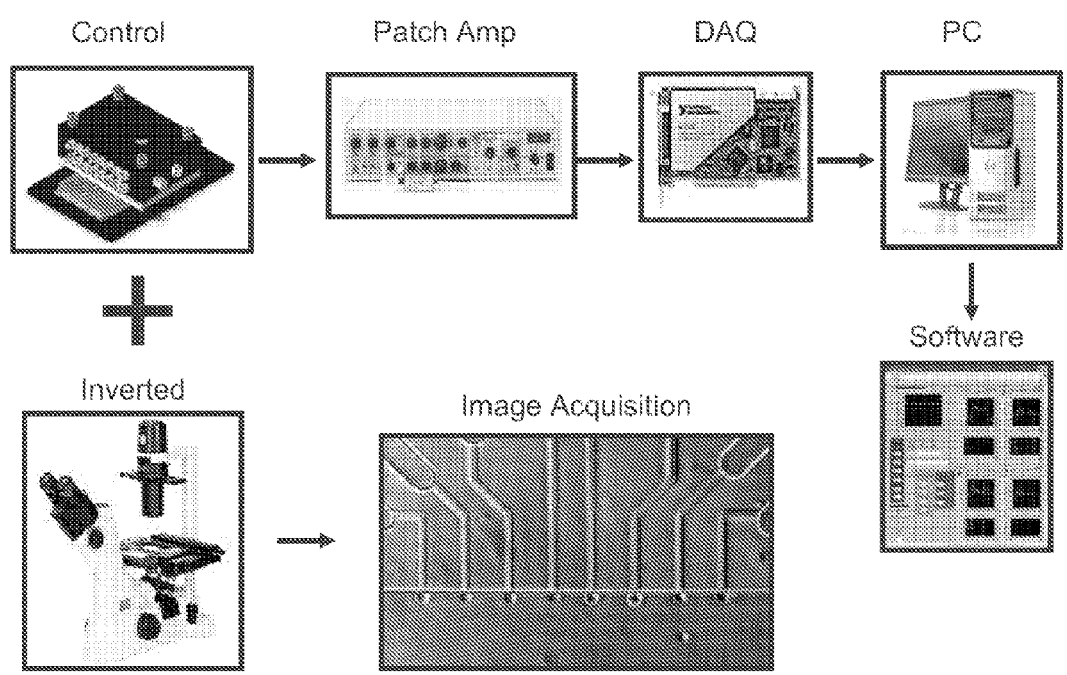
FIG. 16 is a schematic of the system according to specific embodiments of the invention in connection with other equipment.

As shown in FIG. 16, interface system 301 design is compatible with traditional equipment. For example, interface system 301 be used with a microscope (e.g., an inverted microscope) 303 to produce image acquisition 313. As further shown in FIG. 16, where the interface system includes a universal connector, it can be linked to any amplifier's headstage, here shown as patch amp 305. Patch amp 305 can further be connected to DAQ 307 and a logic device such as a personal computer (PC) 309. The preceding electronics can be controlled with a graphical user-interface software 311 (e.g., LabVIEW, National Instruments Corp., Austin, Tex.).

In one embodiment, switching from one channel to the next (e.g., between 15 or more channels) can be done manually (thereby eliminating any switching noise associated with an on-board MUX) with a rotary dial on the side of the box.

Optionally, in one embodiment a pressure-control box is provided for attachment to the interface box system via the luers (not shown). As such, a series of one or more channels can be configured to trap all the cells simultaneously or individually at trapping sites. In one embodiment trapping is achieved using a range of positive and negative applications from −300 inches/Hg to 300 inches/Hg. In another embodiment trapping is achieved using a range of positive and negative applications from −30 inches/Hg to 30 inches/Hg. Optimal cell trapping pressure provides that the cells trap rapidly and yet are not damaged by any excessive pressure.

Optical Viewing

It is envisioned as described herein that optical viewing of particles within channels of the microfluidic chip devices can be achieved through any of a number of microscopic viewing or other detection systems. Such systems can be manual and/or automated and can be upright or inverted. Suitable forms of microscopy include but are not limited to bright field microscopy, dark field microscopy, phase-contrast microscopy, fluorescence microscopy, confocal laser scanning microscopy, deconvolution microscopy, electron microscopy, and ultrasonic force microscopy. Where automated detection or viewing is employed, the images or signal can be conveyed to a logic device for processing and analysis of data.

Electroporation

In general, in another aspect, devices and methods for electroporation of arrays of particles with substances are provided. The particles can include but are not limited to vesicles (e.g., lipid vesicles) or cells. The particles can be microorganisms as defined herein. In one embodiment, cells include human cells. In another embodiment, the particles are Oocytes. In a particular embodiment, cells are stem cells (e.g., human stem cells and/or human embryonic stem cells). The substances can be any of a number of physical materials including but not limited to solutions, compounds and molecules including biologically active molecules as defined herein. In one embodiment, the substance is a nucleic acid as defined herein. In a particular embodiment, wherein the substance is a nucleic acid, the nucleic acid includes a gene sequence. In another embodiment, wherein the substance is a nucleic acid, the nucleic acid is a short interfering RNA (siRNA) molecule. In another embodiment the substance is a polypeptide as defined herein.

Where the substance to be introduced by electroporation is a nucleic acid, it can be single-stranded, double-stranded, or higher order, and can be linear or circular. Exemplary single-stranded target nucleic acids include mRNA, rRNA, tRNA, hnRNA, ssRNA or ssDNA viral genomes, although these nucleic acids may contain internally complementary sequences and significant secondary structure. Exemplary double-stranded target nucleic acids include genomic DNA, mitochondrial DNA, chloroplast DNA, dsRNA or dsDNA viral genomes, plasmids, phage, and viroids. The nucleic acid can be prepared synthetically or purified from a biological source. The nucleic acid may be purified to remove or diminish one or more undesired components of the sample or to concentrate the nucleic acids. Conversely, where the nucleic acid is too concentrated for the particular assay, the nucleic acid may be diluted.

Figure 17:
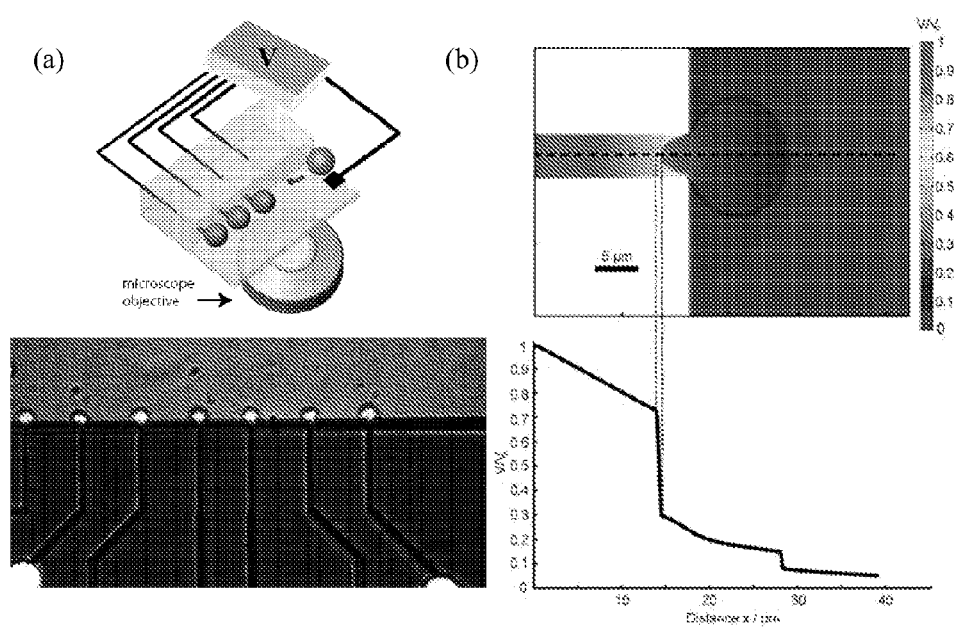
FIG. 17A is a schematic and photomicrograph of the system according to specific embodiments of the invention.
FIG. 17B is a graph showing Femlab simulation result quantifying potential drop across a membrane.

To realize the goal of using the device described herein for rapid screening (e.g., in siRNA delivery and screening), the electroporation process flow and procedure can optimized. As described herein, a single-cell electroporation device for reversible electroporation and the insertion of materials into cells is provided [Khine (Electroporation Chip)]. As shown in FIG. 17A, both schematically and in a photomicrograph, the device layout provides for sequestering of individual cells in lateral PDMS channels before electroporation. As such, the electric field can be focused such that the greatest potential drop occurs across the first membrane of the cell, as quantified through a 2D Femlab simulation (FIG. 17 panel B; the bottom graph illustrates potential drop along midline). In this way, localized electroporation can be achieved at relatively low applied voltages. Because resistance is inversely proportional to surface area, the small portion of the cell inside the immobilizing channel has a much higher resistance (80×) than the portion outside the channel. The greatest potential drop therefore occurs across the portion of the cell membrane inside the channel and localized electroporation occurs here. Low applied voltages are sufficient to achieve electroporation with a high electric field across that first membrane (750 V cm−1). This is within the range (300-1000 V cm−1) that Tsong reported for the dielectric strength of a lipid bilayer membrane [Tsong]. Electroporation can be monitored by observing an increase in current that corresponds to the opening of pores that enable ions to pass. The design makes use of a trapping channel whose height is approximately a third of the cell's diameter (e.g., 3 µm). A cell is hydrodynamically trapped by applying negative pressure (e.g., about −2 psi) to the trapping channel via an attached syringe as a cell passes by. Depending on the pressure application, cells can be trapped in, for example, <1 second–30 seconds (see FIG. 18).

In one embodiment, the cross-sectional dimensions of the trapping channels can be about 3 µm×3 µm. In another embodiment, the cross-sectional dimensions can be less than 10 µm×10 µm. In another embodiment the cross-sectional dimensions can be less than 3 µm×3 µm. In a particular embodiment, the cross-sectional dimensions can be less than 1 µm×1 µm. The entire device can be fabricated using micro-molding of the elastomer polydimethylsiloxane (PDMS). In one embodiment, a silicon mold is prepared using established surface micromachining techniques, with negative photo-resist SU-8 to define the features. In a particular embodiment a base and a curing agent of PDMS can be mixed (e.g., at a ratio of 1:10) and the liquid mixture can be poured onto the silicon mold and cured at, for example, 125° C. for 10 minutes. The device can then be bonded, to the base of a 96 well plate (see e.g., FIG. 19). In one embodiment, a control interface is provided that mates to the 96 well plate, offering both electrical connection and pressure control. In one embodiment, hollow Ag/AgCl electrodes that traverse a printed circuit board (PCB) can be inserted into the wells and provide both electrical connection as well as pressure. The PCB board can be pressure clamped to the 96 well plate such that pressure can be applied through the hollow electrodes (see e.g., FIG. 15A). These electrodes, which serve both to apply the voltage and record the current, are suitable recording electrodes because of their minimal electrical double layer (EDL) (not shown). Sectioning the electrodes can allow for pressure control through the electrodes (e.g., Ag/AgCl electrodes). Optionally, electrodes capable of serving as both the driving (e.g., applying the voltage) as well as the sensing (e.g., measuring the current) electrodes. As such separate electrodes would not be required for these functions. Such an electrode setup is also useful where both voltage clamping and current clamping are both desired in a single configuration. Other electrode configurations can also be envisioned, such as thin wire electrodes (e.g. Ag/AgCl) which dip into the wells or channels.

As discussed herein, the interface box, in addition to pressure connectors, can include universal connectors to output to two standard patch clamp amplifiers. In one embodiment the box can be configured such that up to 8 channels can be recorded from using each patch clamp amplifier by simply turning the manual dial. The amplifier can be controlled by, for example, a custom-made LabVIEW (National Instruments) application through a data acquisition card (e.g., PCI-6024E, National Instruments). The chip can be monitored with either inverted or upright microscopes (e.g., Eclipse TS100, Nikon, Melville, N.Y.) with a fluorescent module and is video captured with a camera (e.g., DXC-190, Sony) and a video capture card (e.g., microVideo DC50, Pinnacle) on the same computer.

Figure 20:
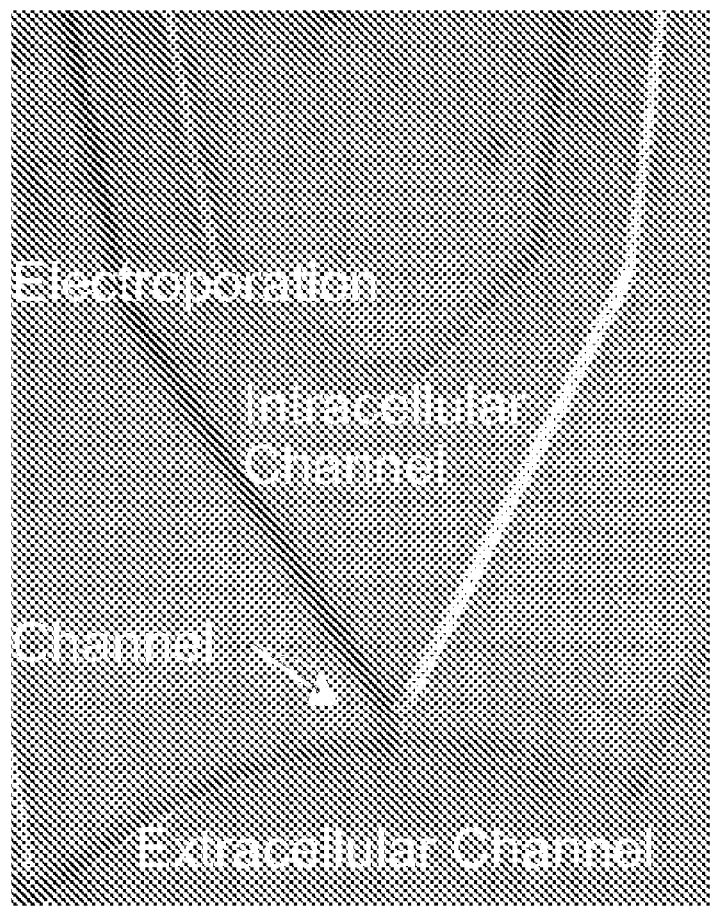
FIG. 20 illustrate aspects of an example microfluidic device for backside perfusion according to specific embodiments of the invention.

In another embodiment, the device includes a capillary channel feeding into the cell trapping channel for intracellular delivery (see FIG. 20). In this embodiment, the design includes a Y-shaped intracellular backside perfusion channel that feeds into the cell trapping channel that is 3×3 µm in dimension. The length of the cell trapping channel is 50 µm. The cell is pulled in and electroporated with one side of the Y-channel having a negative pressure applied through the interface, while the other side of the Y-channel remains closed. To deliver the compounds, the other side of the Y-channel has a positive pressure applied to it through the interface. Efficient delivery of compounds using the backside perfusion channel has been demonstrated with propidium iodide as well as dextran attached fluorescein [Khine (Electroporation Array)].

Figure 19:
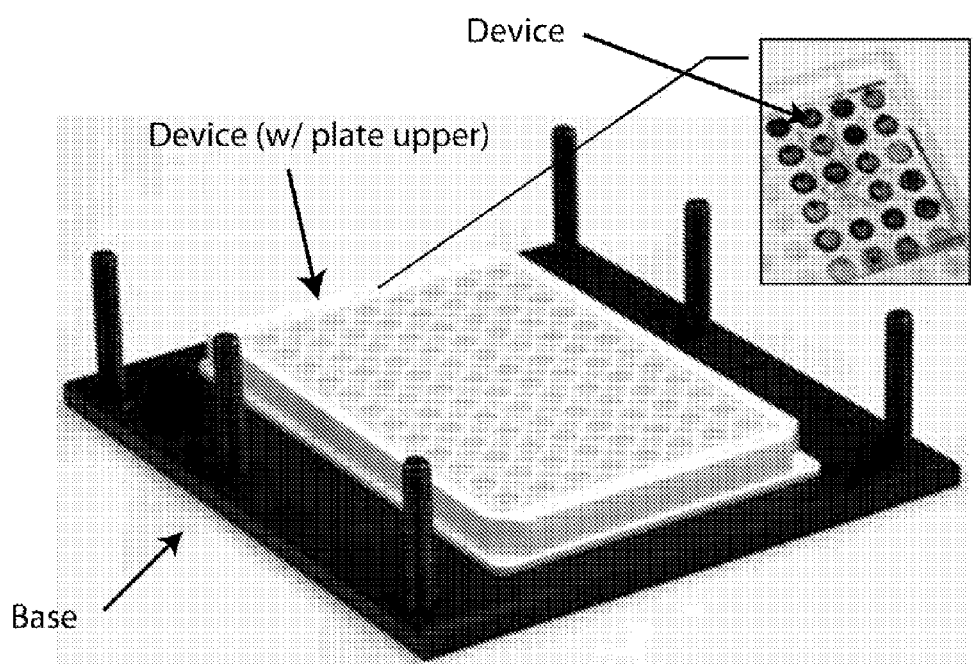
FIG. 19 shows the microfluidic device of one embodiment of the invention coupled to a microplate.

In a further embodiment, a control algorithm is included in which a computer program can automatically control electroporation, detect when electroporation has occurred, release the electric field upon electroporation, and monitor the cell's resealing. As illustrated in FIG. 19, the same cell reseals more completely and faster with the control loop that cuts off the voltage application after electroporation has been achieved.

Integration of Microfluidic Devices with Reservoir Structures, Including Standard Well Plates In one embodiment, PDMS microfluidic chip devices are irreversibly bonded to standard bottom-less 96 well plates using a bonding process. Several bonding techniques known in the art can be used, for example, plasma bonding, thermal bonding, and adhesive bonding.

Figure 22:
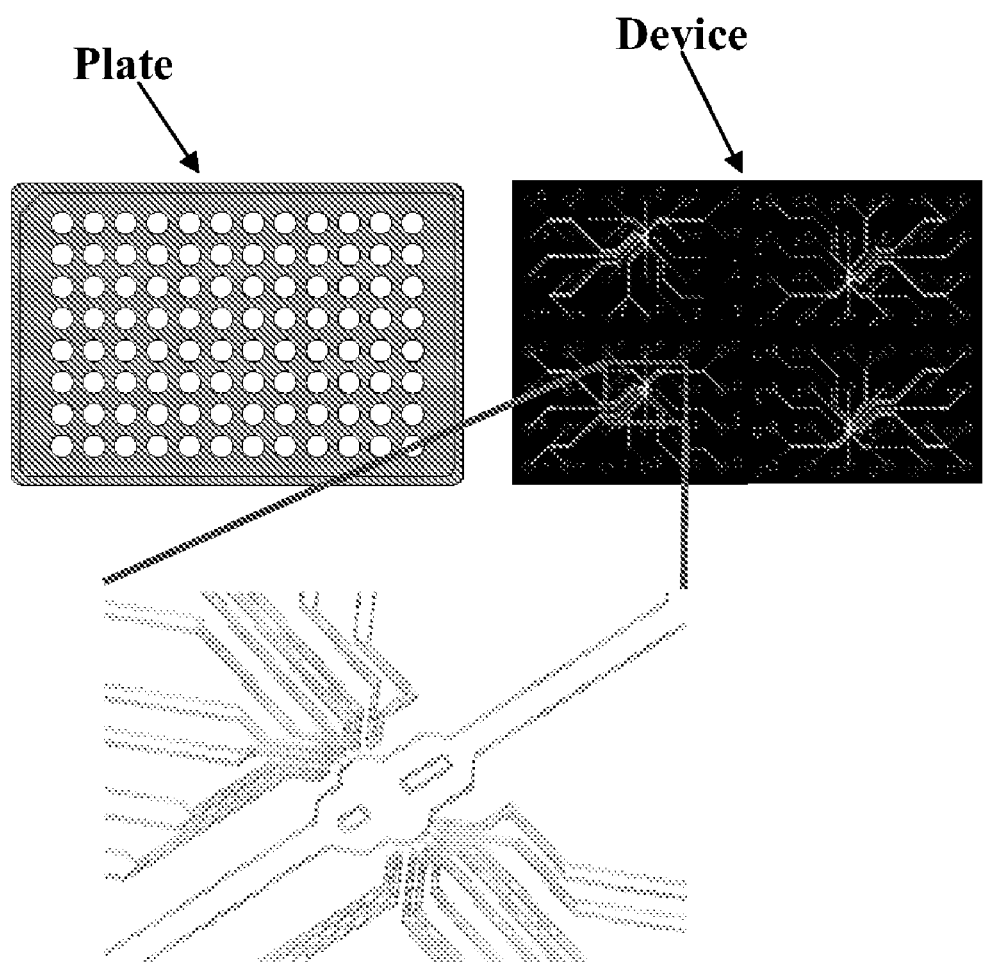
FIG. 22 is a schematic of microfluidic devices coupled to a microplate according to specific embodiments of the invention.

As shown in FIG. 22, in a particular embodiment, four (4) devices are bonded to a standard bottom-less 96 well plate as four (4) 4 well×6 well quadrants 409 (FIG. 22, inset). For each quadrant, there is a single viewing window where all the cells can be viewed, trapped and electroporated in individual channels. Each channel can terminate in a well or reservoir. The quadrant design with small trapping channels and backside perfusion channels is illustrated in schematic form in FIG. 22, inset. In other embodiments, different groupings of wells on a 96-well plate (or other well plate formats) may be used as independent devices. Groupings can be as small as two wells. In another embodiment, there is one central viewing window for the entire microplate, in which substantially all of the channels are directed towards this region.

Fabrication

The process of fabricating microfluidic chip devices are typically very manual, requiring holes to be punched manually and precisely to access the microfluidic channels. The fabrication method described herein eliminates the need to manually punch PDMS devices. The benefits of the approach include: improving manufacturing ease, improving yield (critical alignment no longer an issue), and significantly increasing production speeds. In one embodiment, one or more microfluidic channels are molded into one side of a substrate (e.g. PDMS). This side of the substrate is bonded directly to a multi-well plate (e.g. 96-well microplate) where the termination of the microchannels align to the well positions on the multi-well plate. This embodiment eliminates the need to punch holes through the microchannel substrate to allow fluid connection between the wells and the microchannels. In another embodiment, the microchannels are molded into a substrate (e.g. PDMS) by using a cavity mold with pre-defined holes created in the molding process that correspond to the holes of the multi-well plate. In this embodiment, the microchannel side of the substrate is bonded away from the multi-well plate, but the necessary through holes to create fluidic connections are already established. An additional layer (e.g. PDMS, glass) can be bonded to the microchannel side to seal off the channels.

Loading and Priming the Microfluidic Devices

Loading microfluidic-based chip devices typically involved pushing the fluid through with significant positive pressure to 'prime' the device. Applying such pressures can cause delamination of the device. Instead, load and priming is achieved using a simple loading approach visa vie vacuum filling.

Rapid cell trapping is illustrated in FIG. 18. The frame by frame micrographs shown in FIG. 18 demonstrates cell trapping using in less than five seconds using one embodiment of the microfluidic chip described herein.

Two Microfluidic Chip Device Designs for Electroporation

Figure 23:
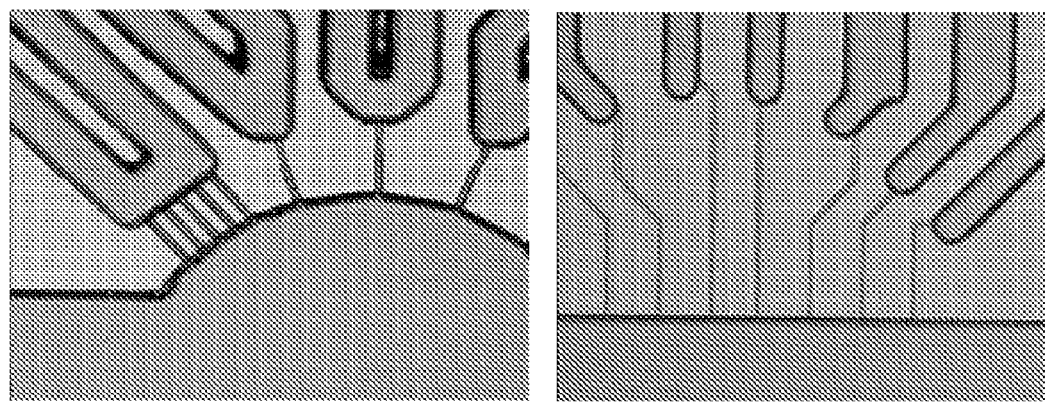
FIG. 23 illustrate aspects of an example microfluidic device for backside perfusion (left) and an example microfluidic device with perfusion channels in a main channel (right) according to specific embodiments of the invention.

As shown in FIG. 23 (left), in one electroporation design embodiment, compounds can be delivered via a backside perfusion channel. In the other design, as shown in FIG. 23 (right), compounds can be perfused from a perfusion channel located in the main channel. Cell-impermeable calcein was used in electroporation experiments using the two designs to verify that the small portion of the cell membrane pulled into the trapping sites was locally electroporated.

Single Cell Electroporation Chip Design

Microfabricated devices can be ideally suited to both isolate single cells and focus the electric field. In 2001, Huang et al. introduced the first microfabricated single cell electroporation chip [Huang]. While the approach described by Huang et al. may achieve single cell electroporation, it suffers from low throughput (only one poration site) and the large expense of producing a microfabricated device that required multiple photolithography masks and wafer to wafer bonding/alignment steps. In 2002, Nolkrantz et al. demonstrated functional screening of intracellular proteins by using high voltage electroporation to introduce fluorogenic enzyme substrates and receptor ligands into single cells [Nolkrantz (Functional Screening)]. An effective way to monitor protein interaction inside living cells is to use fluorescent molecules, which absorb light at a particular wavelength and emit it at a longer wavelength. Fluorescent molecules can be coupled to antibodies to bind selectively to particular macromolecules. This enables both monitoring of both intracellular protein distribution and protein-protein interactions. Nolkrantz et al. developed a method using glass pipettes biased at high voltages (~10 kV) to electroporate single cells and a plurality of cells patterned in PDMS microwells for functional screening of intracellular proteins. Again, like the Huang et al. approach, this single cell electroporation method suffers from low throughput because only one cell can be accessed at a time and micromanipulation of a pipette is required. More recently, various academic groups are working on single-cell electroporation lab-on-a-chip platforms. The BIOS lab at the University of Twente in the Netherlands, for example, is working on silicon and glass based single cell electroporation chips. Valero et al. showed that they could make a vertical glass system with 4 um holes. They demonstrated that propidium iodide entering the cell after an hour of permeabilization, but resealing and cell viability has not yet been demonstrated. Furthermore, they have not yet introduced electrically addressable cell trapping sites [Valero]. Lee et al at Sandia national labs developed a prototype chip for single vesicle electroporation. The silicon chip, manufactured in a similar approach to Huang's, supports a 1 μm thick dielectric silicon nitride membrane with a 6 μm vertical pore patterned that connects the two fluidic chambers. This platform is limited to a single pore per substrate [Lee].

The single cell electroporation approach described herein differs significantly from existing technology, with several distinct advantages. With respect to Huang et al's approach, the present microfluidic chip design offers a simpler, more cost-effective, and faster batch manufacturing approach. Instead of a multilayered silicon device that requires precise two side alignment, wafer bonding, and KOH etching to manufacture, a simple micromolding procedure is used to fabricate elastomeric devices. Suitable elastomeric compounds include but are not limited to polydimethylsiloxane (PDMS), silicone, fluorinated silicone, Teflon, Nafion, and the like. Whereas cells are consecutively addressed in the Huang et al device, in one embodiment the chips described herein include an array such that a plurality of cells can be simultaneously sequestered and electroporated. A next batch of cells can then be moved in and porated. The microfluidic electroporation devices described herein can be mated to 96-well plates such that compounds and cells can be easily introduced. In the same amount of time it takes to manipulate one cell in the flow-through design of Huang et al., the present design can manipulate an entire array of cells (e.g. fifteen or more cells; fifty or more cells, etc.). Moreover, in one embodiment the chip design enables the monitoring of several cells side by side in the same field of view for a direct comparison.

Using a lateral cell trapping approach allows trapped cells to be arrayed with a distance of, for example, only 20 μm, increasing the cell density in the active area of the device by two orders of magnitude over existing microfabricated electroporation setups. In one embodiment the lateral trapping sites of the chip are less than 100 μm apart. In another embodiment, the lateral trapping sites are less than 25 μm apart. In a further embodiment, the lateral trapping sites are less than 5 μm apart. Furthermore, the chip design can readily accommodate multiple capillary channels feeding into the cell trapping channel for multiplexing of intracellular reagents. Additionally, the present chip design provides for the cell's deformation into the trapping capillary such that the deformation is in the same horizontal optical plane as the cell body. As such, the entry of compounds from the electroporated patch into the cell body can be easily visualized. In one embodiment, the transparent elastomer PDMS, unlike opaque silicon, enables fluorescent detection and monitoring throughout the whole process.

With respect to Nolkrantz et al.'s approach, the platform described herein does not require manipulation of pipettes (and vibration isolation equipment), high voltages, or adherent cells. In one embodiment using cells in suspension facilitates work on ex vivo cells that have been dissociated from tissue samples. The entire device can be encased in a microfluidic enclosure and readily automated. In one embodiment, recording of current through the porated membrane suing a patch clamp amplifier (via Ag/AgCl electrodes) allows accurate current traces not commonly reported. In traditional electroporation set-ups (large parallel electrode setups), the bulk of the current is carried by the extracellular electrolyte solution, making it impossible to record the current through a single cell. Existing studies on single cells either do not record current through the high voltage electrodes [Hass, Nolkrantz (Functional Screening)] or do not focus on detailed measurements of current changes during poration [Valero]. In contrast, use of the system described herein focuses on the analysis of changes in cell resistance due to electroporation by assaying current jumps due to membrane poration, which will improve yield and controllability of the procedure. Furthermore, the system can include feedback controls based on changes in membrane resistance due to electroporation, which can improve cell resealing and controllability of the electroporation procedure.

It is envisioned that the electroporation system described herein provides for real-time electrical and optical monitoring before, during, and after electroporation. Additionally, the system provides for real-time feedback control to promote membrane resealing and cell viability.

Electroporation Conditions for Resealing

Figure 24:
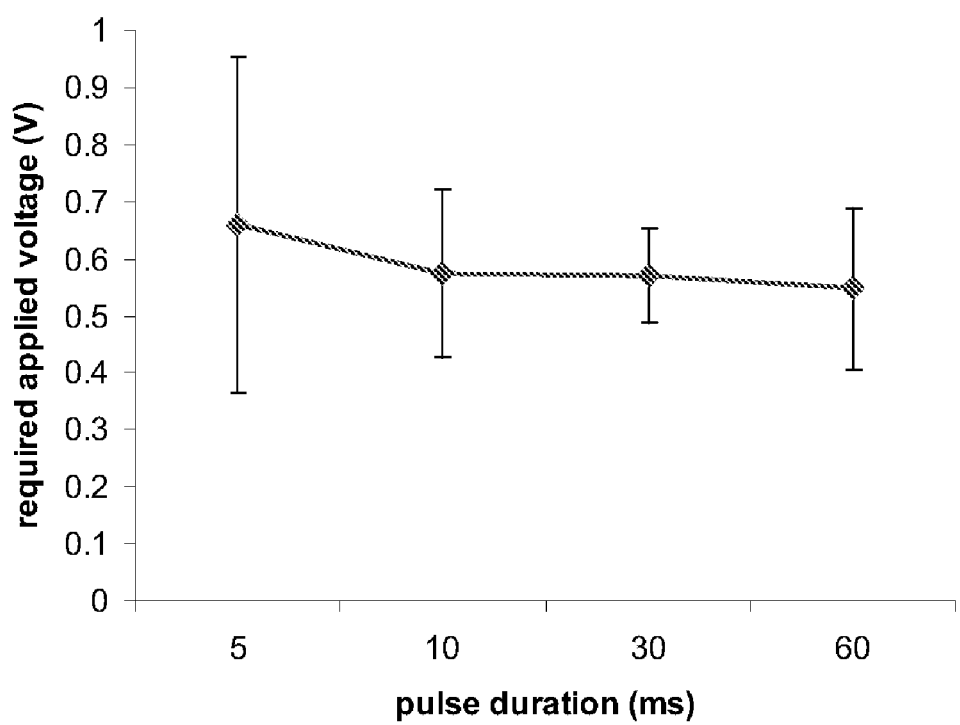
FIG. 24 is a graph showing applied voltage required for electroporation versus pulse duration according to specific embodiments of the invention.
Figure 25:
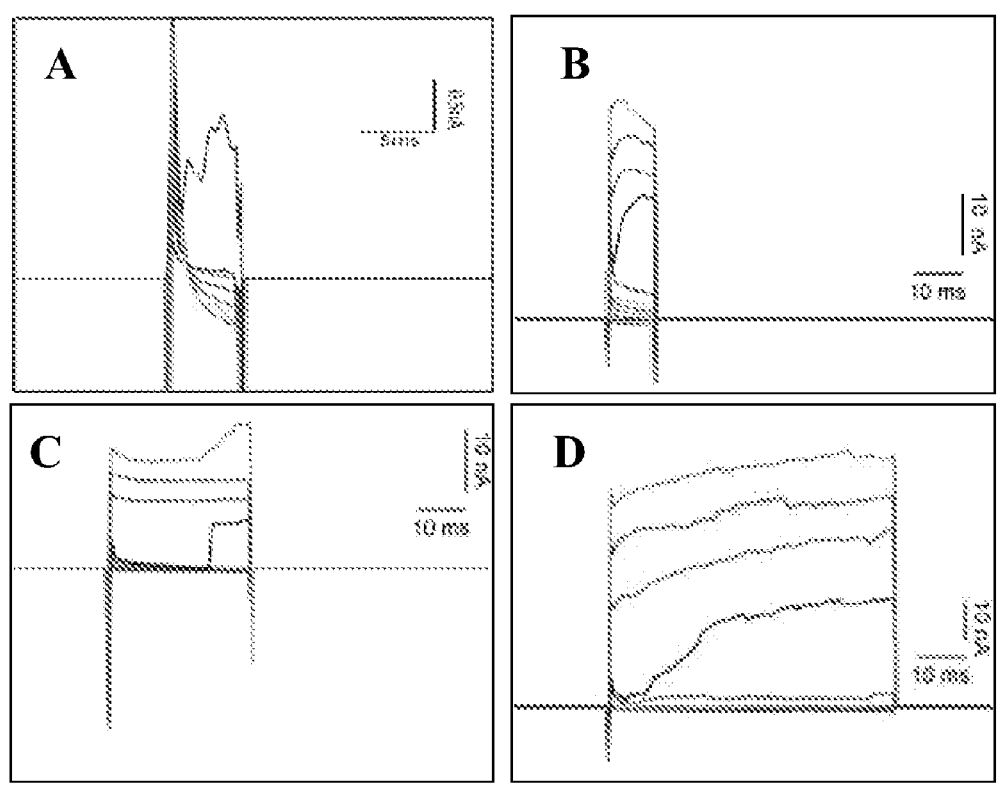
FIG. 25A-D show exemplary graphs of current versus time results in response to applied voltages square waves of varying durations according to specific embodiments of the invention.

To determine optimal electroporation conditions, various parameters were tested. For example, pulse time lengths from 5 ms to 60 ms, with voltage step sizes of 0.1V from 0V to 1.0V. As shown in FIG. 24, when using shorter pulse widths, higher voltages are required to achieve electroporation. As indicated, variations from cell to cell can be appreciable. Examples of resulting current traces (shown as nA in the y-axis) versus time (shown as ms in the x-axis) are shown in FIG. 25. The examples shown in FIG. 25 represent applied voltage of varying durations, from 5 ms to 60 ms. The characteristic jump in current is indicative of pores opening and ions passing. Resealing is defined as the resumption of high resistance due to the closing of the pores, as determined by impedance measurements described in herein.

Figure 21:
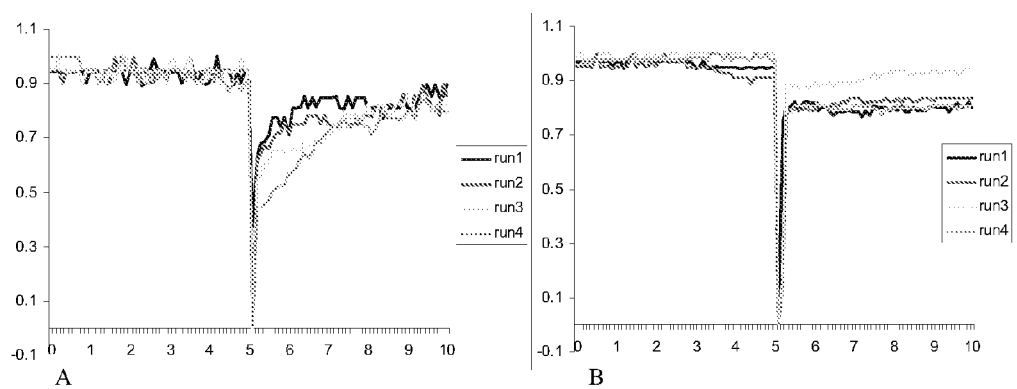
FIG. 21A is a graph showing resealing after electroporation of a cell without a control loop.
FIG. 21B is a graph showing resealing after electroporation of a cell with a control loop.
Figure 27:
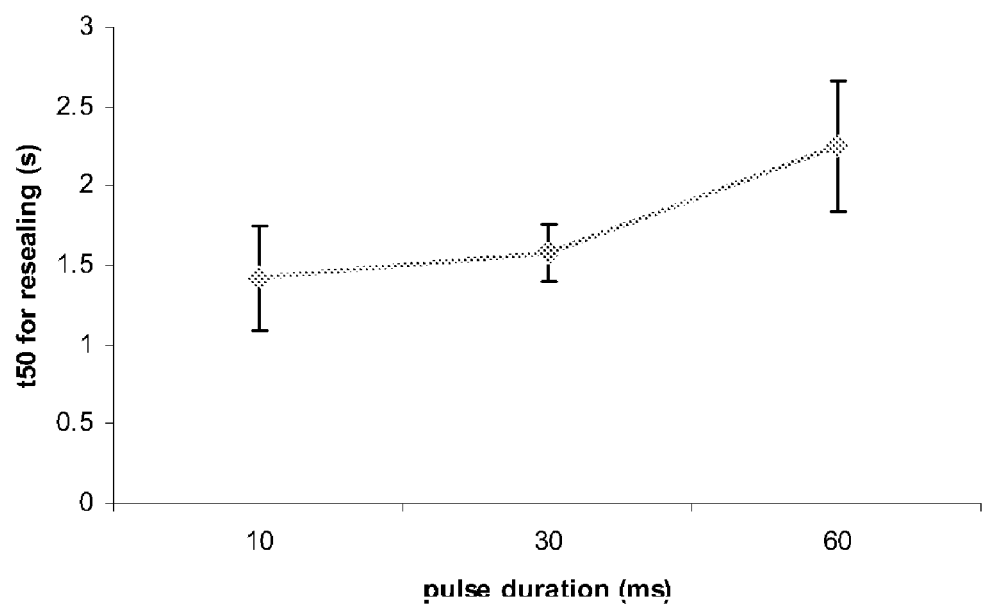
FIG. 27 is another graph showing resealing results as a function of pulse duration according to specific embodiments of the invention.
Figure 28:
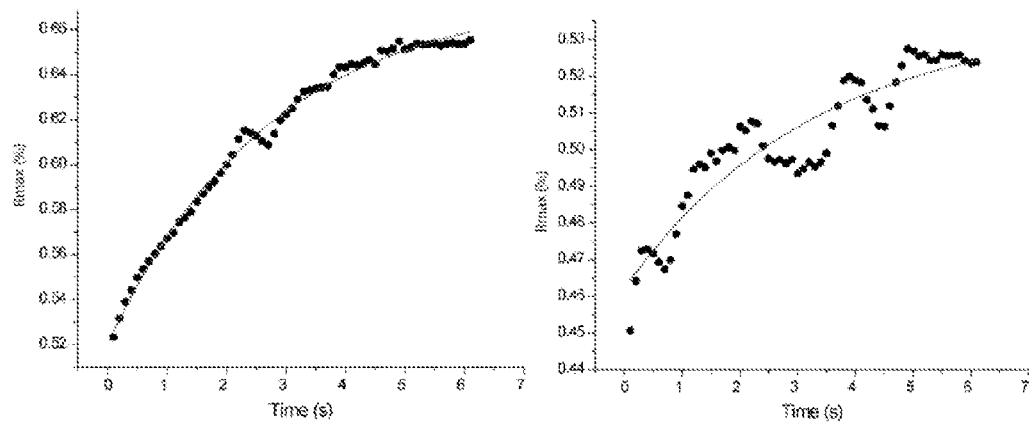
FIG. 28 shows graphs of resealing kinetics for two cells according to specific embodiments of the invention.

The time constant for resealing is calculated by the time to achieve 50% of the original resistance value. Examples of the resealing data are shown in FIG. 21. In FIG. 21 the percentage of resealing for HeLa cells (without a control loop) in relation to pulse duration in ms is shown. In FIG. 21, the average percentage of resealing (shown in the y-axis) as f function of pulse duration (shown as ms in the x-axis) are indicated. As shown, longer pulse widths typically result in less resealing, though as in most biological systems, the spread is large. In the example shown in FIG. 21, the resealing study tested HeLa cells without a control loop during electroporation. The correlation between the pulse duration and t50 to resealing are shown in FIG. 27. Longer pulse widths, as expected, require longer times for the cells to reseal on average. FIG. 28 includes plots for two individual cells that illustrate the resealing kinetics. By fitting the resealing resistance as a function of time to an exponential, the time constants can be determined.

Figure 29:
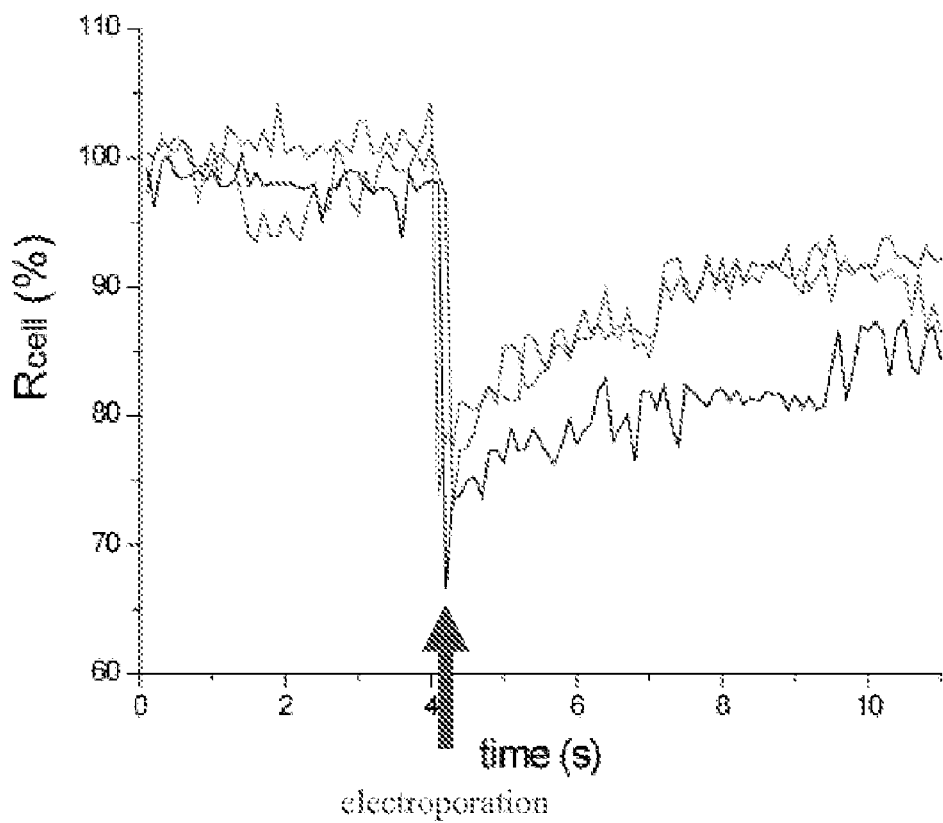
FIG. 29 is a graph showing cell resistance values in relation to electroporation.

Impedance Measurements to Monitor a Cell Both During and Directly after Electroporation As shown in FIG. 29, by holding a cell at a low voltage immediately after applying the electroporation protocol, resealing kinetics can be resolved. The resistance of a cell is measured by holding it with a low voltage (10 mV). Immediately after the cell is electroporated, the holding voltage resumes and the resistance out-putted.

Use of an Automated Control Loop

Figure 30:
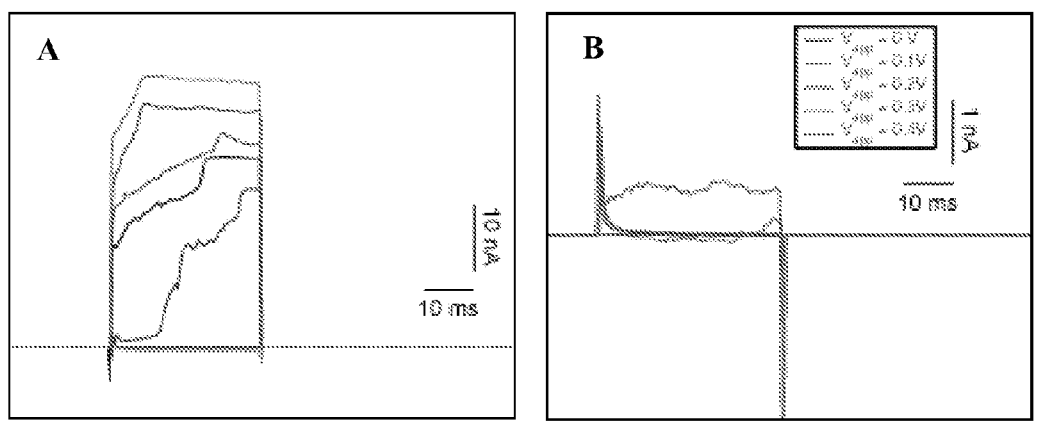
FIG. 30A is a graph showing results upon application of an electric field without a control loop.
FIG. 30B is a graph showing results upon application of an electric field with a control loop.

An automated LabVIEW program was used that releases the electric field when the current 'jumps' to a value greater than 1.5× the pre-poration current. This corresponds to an electroporation event. As shown in FIG. 30A, without a control loop, the cell continues to undergo electroporation as indicated by increasing resistance (shown as nA in the y-axis) over time (shown as ms in the x-axis). In contrast, as shown in FIG. 30B, where a control loop is employed, the voltage is turned off after the jump in current (in the example, at 0.4V). The increase in current corresponds to a decrease in membrane resistance when the cell is electroporated. By reducing or turning off the applied voltage after the electroporation is detected, cell/membrane integrity is preserved.

As is evident from FIGS. 21A and B, in which the same cell was electroporated without the control loop 4 times (see FIG. 21A) and then 4 times with the control loop (see FIG. 21B). The intensity was renormalized after each subsequent run. The resealing kinetics improve dramatically with the feedback loop. With this algorithm, electroporation conditions need not be set a priori using test cells, but can be set such that after the cell is electroporated, the electric field is released. In this way it can be ensures that the cell is electroporated (e.g., the voltage can be increased until electroporation occurs and then backed down immediately after this event).

Figure 31:
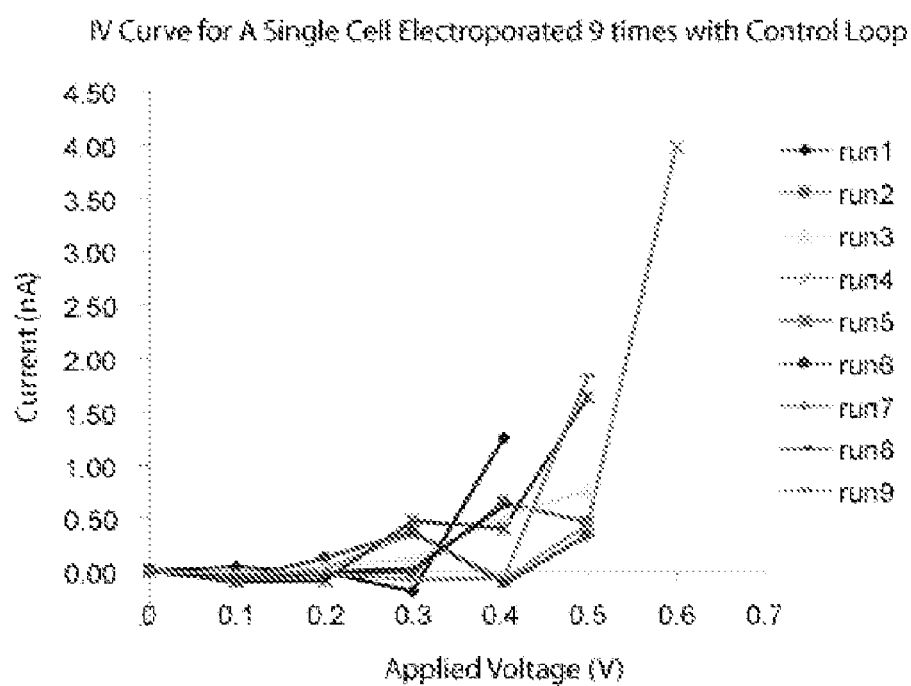
FIG. 31 is a graph showing results after repeated electroporation of a cell with a control loop.

As shown in FIG. 31, using the feedback control loop program, a cell was successfully electroporated up to nine times. Such was not previously achievable without the control loop. Eventually, after about 4 electroporation events, the resistance of the cell membrane remained low for over 30 s, thereby indicating that resealing was no longer occurring and the cell was no longer viable. Thus, the control loop enables a number of multiple electroporation events without irreversible damage to the cell.

Verification of Material Introduction Via Fluorescence Analysis

Figure 32:
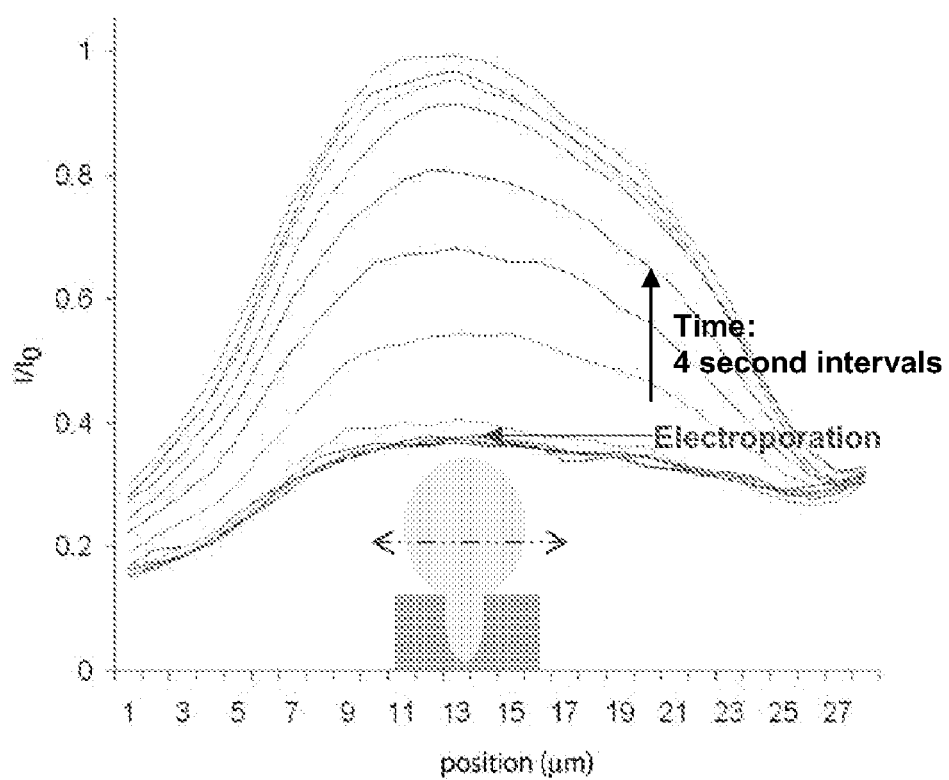
FIG. 32 is a graph of results of electroporation using a fluorescent dye.
Figure 33:
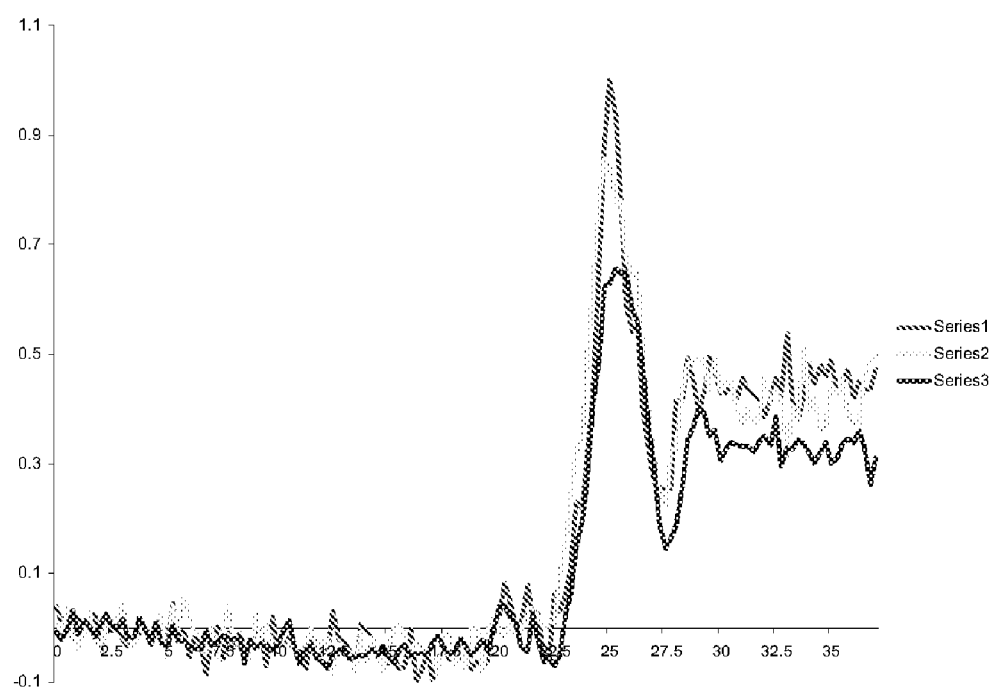
FIG. 33 is another graph of results of electroporation using a fluorescent dye.

Otherwise impermeable dyes were tested for introduction into a cell after electroporation. To quantify how much material goes into the cell per a given pulse condition, a number of experiments were performed. As shown in FIG. 33, in a photomicrograph of one example of such an experiment, an array of HeLa cells are trapped and cell-impermeable calcein is introduced by electroporation. It is envisioned that the two different chip designs described herein are both useful for introducing material intracellularly. In one case the backside perfusion design can be used and in another extracellularly introducing material can be introduced via an external perfusion channel. In one embodiment, after a first small portion of the cell is electroporated, it is possible to additionally electroporate the outer membrane. As shown in FIG. 32, the fluorescent dye calcein demonstrably enters the cell via a backside perfusion channel electroporation. FIG. 33 shows the dosing of two electroporated cells (the series 1 and the series 2 lines) versus a control cell (the series 3 line). This graph demonstrates that some of the dye is either getting into the cells or is sticking to the cell membrane so there is some degree of increased intensity before electroporation. However, as is shown in FIG. 32, this fluorescence level remains relatively constant over time unless the cell is electroporated. The time for the dye to enter the cell does not correlate with the membrane resealing time. Optimization of the pulse conditions can include altering conditions such that the pores would remain open for longer or shorter periods, and/or the compounds can be introduced more rapidly or slowly.

On-Chip Cell Culture

Figure 34:
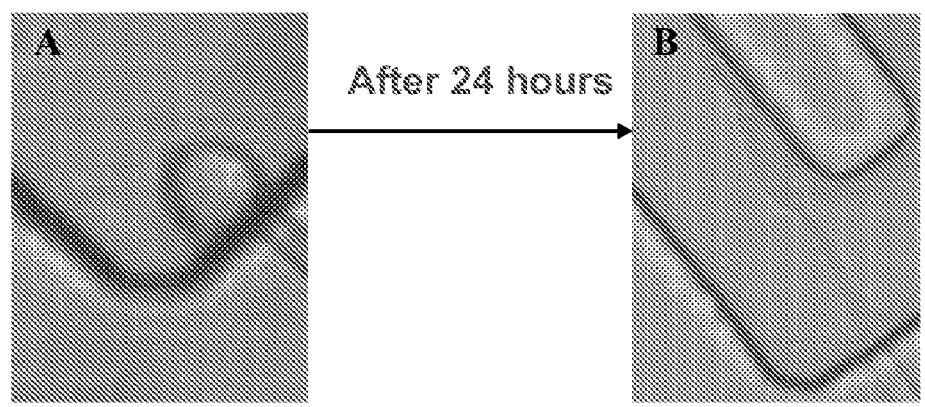
FIG. 34A-B show photomicrographs of a cell in a microfluidic device over time according to specific embodiments of the invention.

It is envisioned that in some cases it will be desirable to culture cells on chip (i.e. within the microfluidic device) after they have been trapped in a trapping channel. The trapping event, it is conceivable, could damage the cell such that it would not be healthy enough to be cultured. To determine if the trapping event was damaging the cells, cells were trapped and cultured. As indicated in FIG. 34, the cells plate within 24 hours, demonstrating that cells can be cultured within the device post-trapping.

Electroporation of Various Cell Types

Using the interface system described herein, electroporation of the following cell types was achieved: Chinese hamster ovary, (CHO), human cervical cancer (HeLa), human breast cancer (MM468 breast cancer), epithelial (16HBE14o), mouse fibroblast (NIH 3T3), and endothelial cells (data not shown).

Efficient electroporation conditions can include but are not limited to, for example: the cell membrane is porated 99% of the time (by monitoring voltage dependent current responses, i.e. measuring the resistance of the cell membrane), the cell membrane reseals 95% of the time (by monitoring currents at low applied holding voltages over longer time durations), the cells plate at least 80% of the time.

Experimental results have shown it is possible to achieve electroporation up to and including 93% of the time. Electroporation yield depends on pulse parameters, and for 60 ms pulses, electroporation can be achieved 100% of the time. Electroporation may not be successful at times because of a very low sealing resistance between the cell and the trapping channel walls.

Figure 26:
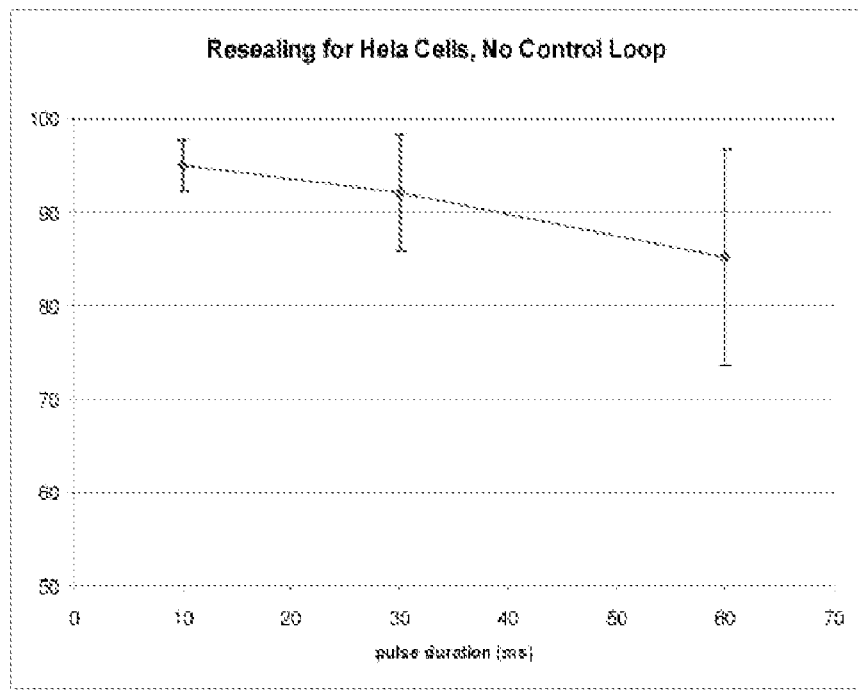
FIG. 26 is a graph showing resealing results as a function of pulse duration according to specific embodiments of the invention.

Further experimental results have also shown there is a tradeoff between resealing and electroporation yield. For resealing 10 ms pulses work best, and resealing 95% of the time was achieved for this pulse length (see FIG. 26).

It is envisioned that optimal dosing can be achieved if uniform doses are consistently applied across cells with variability in dosage, for example, below 10% and such can be achieved over a range of doses (e.g., over 3 orders of magnitude).

It is envisioned that the device design for multiplexing and high-throughput can support trapping and record from N>8 cells automatically and introduction of from N>8 compounds automatically into the cell cytoplasm. In one embodiment, N is >20. In another embodiment, N is >100. in a further embodiment, N is >1000.

Cell Tracking Pre- and Post-Experiment

In one embodiment, the microfluidic chip design is such that cells can be collected from off the chip. In one example, the design supports the collection of one cell per well. Cells can be released from the trapping channels simply by applying a positive pressure to the channels. The challenge in bringing the cells off-chip is the issue of dilution. For example, where only 15 cells are electroporated, keeping track of the 15 cells in milliliter volumes is a challenge. As such, in one embodiment a chip is provided that contains a collection channel with a small volume. Suitable collection channel volumes can range from about 0.5 nl to 1000 nl. In one embodiment the collection channel volume ranges from 1 nl to 100 nl. After all the cells are trapped in their respective trapping sites, the main channel can be washed through with solution lacking cells. Subsequently, the main channel can be closed off. Positive pressure can then be applied to the trapping channels as the collecting channel is opened for entry of the cells. In this manner, cells can be contained within a collection channel for subsequent collection as desired. Variations on collecting channel design enable optional sorting of cells as well as collecting cells in individual channels leading to individual wells. Chip design can be done using AutoCAD® software and masks and subsequently wafers (molds) can be produced. The molds can then be used in soft lithography to produce chips.

In one embodiment, collection of cells from off the chip can includes successful expelling of cells from trapping channels >50% of the time. In related embodiment, successful expelling of cells from trapping channels occurs >75% of the time. In a further embodiment, successful expelling of cells from trapping channels occurs >90% of the time. In another embodiment, successful expelling of cells from trapping channels occurs >99% of the time.

In another embodiment, collecting cells from off the chip includes a sorting step wherein fluorescently-labeled "loaded" cells can be sorted from "non-loaded" cells. In this manner, sorting can be used to separately collect cells successfully electroporated with compounds ("loaded") from "non-loaded" cells.

It is anticipated that in one embodiment, the chip design supports collection of >25% of the original loaded cells. In another embodiment, the chip design can support collection of >50% of the original loaded cells. In a further embodiment, the chip design can support collection of >70% of the original loaded cells. In another embodiment, the chip design can support collection of >90% of the original loaded cells.

In another embodiment where rare and precious cells are involved, efficient cell trapping and sorting of cells is provided. Because rare cells such as stem cells and certain types of primary cells cannot typically be provided in high concentrations, a means to use very low concentrations of cells with the chips is desirable. Moreover, cells expressing a certain protein, for example, may need to be separated from other cells targeted for electroporation, again presenting the situation where the cells are in very low concentration. Working with such low concentrations of cells can be achieved with a cell concentrating mechanism. In one embodiment, using an optical feedback mechanism and an algorithm, an automatic cell detector can signal to open one channel while closing the other such that the targeted cell is directed to the trapping channels, separating them from the bulk volume of solution. It is envisioned that an automated algorithm can be implemented for use with the chip such that selective trapping of mostly or only fluorescently labeled cells is achieved. In one embodiment, the chip design supports cell trapping with cell densities <1×10$^5$ cells per ml. In another embodiment, the chip design supports cell trapping with cell densities $<1\times10^2$ cells per ml. In a related embodiment, the chip design supports cell trapping with cell densities $<1\times10^1$ cells per ml.

Such simple algorithms can also be deployed to automatically trap fluorescent cells or separate cells expressing different proteins. Suitable computer algorithms can detect the cells and automatically control the flow of the cells on the chip.

Chip Design for Higher-Throughput and Lower Volumes of Reagents

Where plate loading is performed manually and cell trapping uses hardware switches, trapping and electroplating substantially 15 cells in parallel can take approximately 30 min per quadrant. This rate amounts to a throughput of about 300 electroporation experiments per work day. To be useful for many biotechnology applications, throughput must be increased significantly over this value. It is envisioned that the microfluidic chip design of the interface system described herein can be designed to accommodate the trapping and electroporation of a plurality of single cells in parallel whereby the time required per experiment is significantly reduced. In one embodiment, the chip design accommodates trapping and electroporating about 2 cells to about 50 cells in parallel. In another embodiment the chip design accommodates trapping and electroporating about 50 cells to about 500 cells in parallel. In a further embodiment, the chip design accommodates trapping and electroporating greater than about 500 cells in parallel. In a particular embodiment, the chip design accommodates trapping and electroporating substantially 15 cells in parallel.

Throughput can be achieved most easily by trapping small populations of cells and electroporating them in parallel. The electrical response will be that of the collective cells, the average of the individual cells. Likewise, feedback can be based on the cells' average electrical response. Another means of achieving significantly higher throughput is to progress to a 384 or 1536 well format. It is envisioned that other well formats in excess of 1536 wells could also be used to achieve higher throughput.

Throughput can also be increased in other ways. Provided that individual cell control and membrane resistance measurement feedback are necessary, throughput can be increased significantly by automating the plate loading/handling and pressure application. The device format described herein accommodates plate handling to be performed by existing high throughput robotic workstations, which can also deliver fluid to the input wells. The interface can also be incorporated in a robotic arm, and pressure can be controlled by electromagnetic valves. Such a system can provide dramatic increases in single cell electroporation throughput, to values above 3000 events per work day.

It is further envisioned that the chip design of the system can accommodate small volumes of reagents. Theoretically, the minimum volume that the chip can hold is the volume of the channels. In one embodiment, the volume of the channels is less than 20 μl. In another embodiment, the channel volume is less than 1 μl. In a further embodiment the channel volume is less than 0.1 μl. To accommodate such small volumes, the volume of critical reagents could be loaded first. Subsequently, the rest of the fluidic connection could be made with filler buffer. Alternatively, the perfusion chamber electrode configuration could be designed such that the electrodes sit in a smaller compound reservoir. This would reduce the volume in the chamber by as low as 1-10 μl. In addition, it is envisioned that using a 384, 1536, or a greater number well format, with consequently closer spaced wells, significantly smaller volumes of reagents would be necessary. For example, by moving to a 384 well format, with closer spaced wells, significantly smaller volumes would be necessary. The minimum volume for 384 well plates is 10 uL. In one embodiment, small reagent volumes are accommodated using the backside perfusion channel that can be loaded with very small volumes of reagents. This can be advantageous where expensive test reagents are used.

It is envisioned that a minimum reagent volume can be determined based on the minimum volume of reagent necessary to continuously perfuse a cell for >1 minute. In one embodiment the minimum reagent volume is determined based on the volume needed to continuously perfuse a cell for >5 minutes. In another embodiment the minimum reagent volume is determined based on the volume needed to continuously perfuse a cell for >10 minutes.

Integration of Electroporation with Electrophysiology

In general, in one aspect, a comprehensive electroporation/electrophysiology platform is provided. The benefits of such a system for transfection of ion channels or the insertion of kinases that modulate channel activity and then subsequent patch clamp measurements of said ion channels are apparent. For hERG screening, the electroporation can be used to deliver the blocking compound into the cell rapidly. Using the platform described herein, it is possible to perform an IC50 with hERG-modulating compound, both intracellularly and extracellularly, and compare fidelity.

In one embodiment an interface system is provided for trapping an array of cells, electroporating the cells and introducing compounds into the cells, followed by performing electrophysiology (e.g., patch clamp) measurements. Combining the electroporation platform described herein with electrophysiology would enable the delivery of compounds of interest into the cell, followed immediately by performance of electrophysiology (e.g., patch clamp, cell attached patch clamp, whole cell voltage clamping and whole cell current clamping) experiments.

Since the amount and rate of compound delivery depends on the permeabilization of the cell membrane, which is a function of the pulse conditions (width and magnitude), optimal pulse conditions must be determined. As such, in one embodiment optimal pulse conditions for a given cell are determined as described herein. Since it is important to ensure that the electroporation pulse does not destabilize the high-resistance seal necessary for patch-clamp measurements, the optimal pulse conditions can include maintenance of a stable high-resistance seal for patch-clamp measurements. It is envisioned that optimal pulse conditions further provide that enough of the cell membrane is porated so compounds can be rapidly delivered into the cell.

Figure 35:
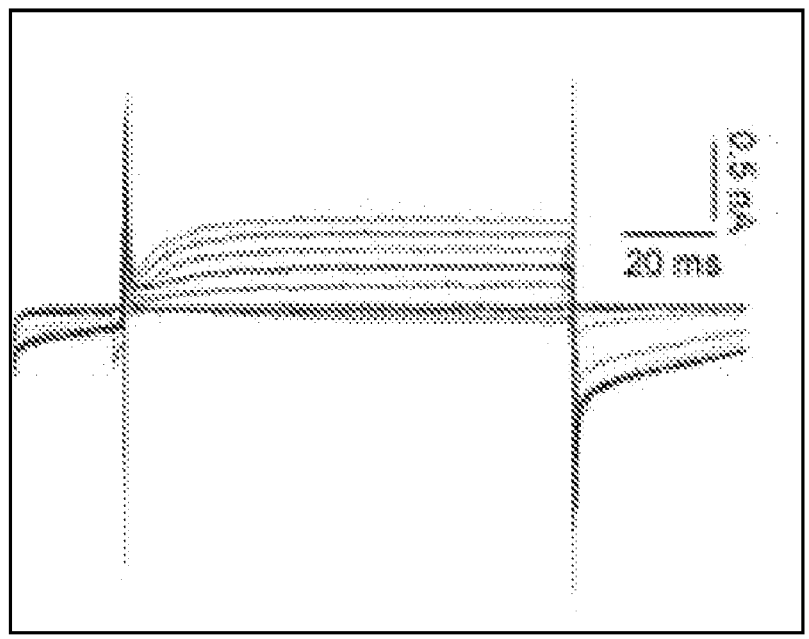
FIG. 35 shows ion channel recordings in relation to a microfluidic device according to specific embodiments of the invention.

As shown in FIG. 35, with respect to performing electrophysiology, the microfluidic chips described herein are also suited to ion channel recordings. In the example shown, a chip can provide recordings relating to KV2.1 ion channels from CHO cells.

Figure 36:
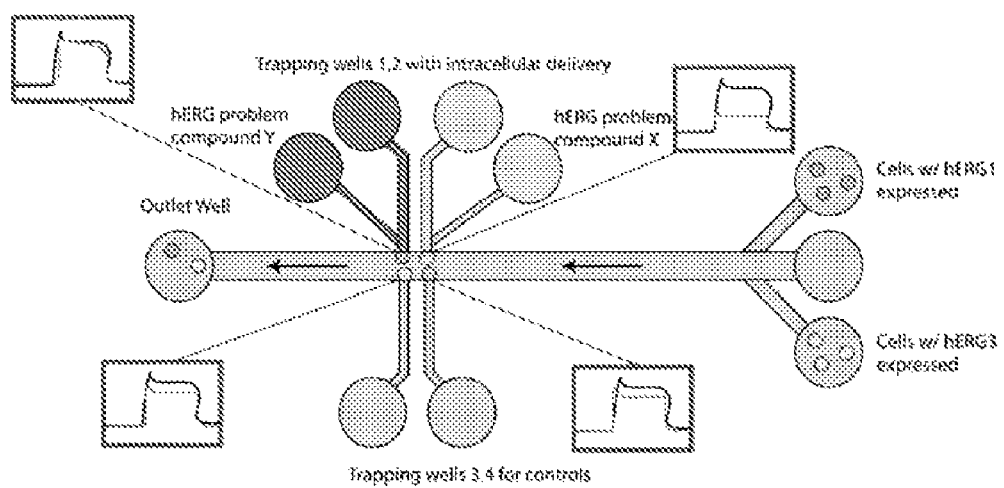
FIG. 36 is a schematic of screening for hERG using a microfluidic device according to specific embodiments of the invention

Exemplary methods of integrating electroporation with the electrophysiology platform described herein include methods to screen for hERG. In FIG. 36 a schematic is shown of how the system described herein can be used to screen for hERG. Using the intracellular perfusion channel of the system, hERG screening could be achieved rapidly by introducing the compounds from the inside out. Screening of different hERG mutants and different compounds could all be achieved simultaneously in the same chip. The process flow is outlined in FIG. 36. Different hERG mutants (e.g., hERG1 and hERG2) can be flown into the main channel and trapped sequentially in designated trapping channels. An array of control measurements (same mutant, no drugs introduced)

can be used for baseline recordings. For the intracellular delivery channels, after the cell is electroporated, the compound can be introduced and the rest of the compounds in the channel can be washed away, after which patch measurement can be taken.

Electroporation pulse conditions can be optimized for delivery of compounds and patch clamp measurements. Because the amount and rate of compound delivery depends on the permeabilization of the cell membrane, which is a function of the pulse conditions (width and magnitude), optimal pulse conditions can be determined. Factors to consider include but are not limited to ensuring that the electroporation pulse does not affect the ability of cellular membranes to form a seal necessary for patch-clamp measurements. Additionally, pulse conditions ensuring that enough of the membrane is porated so compounds can be rapidly delivered into the cell can be determined.

Another exemplary method of integrating electroporation with the electrophysiology platform involves delivery of siRNA into single cells. For example, in one embodiment a specific siRNA sequence is delivered into the cell. In one embodiment, a finite element model (Femlab) is provided that quantifies the delivery of ligands into the cytoplasm based on the principles of diffusion or diffusion with electrophoresis (depending on delivery method) using the Nernst-Planck equations. The model ideally correlates with empirical experiments as well as parametric analyses. Verification of the model of delivery into the cytoplasm can be achieved using fluorescently labeled siRNA molecules that are introduced and quantified based on fluorescent intensity. The compound can be introduced under two conditions, with the electric field on and after it has been turned off to separate the delivery by diffusion and the added effect of electrophoresis. The delivery mechanism can be quantified based on the correlation between the model and empirical measurements.

In another embodiment, detection of RNA-induced gene silencing is envisioned. Silencing of the target protein would conclusively prove the siRNA was delivered satisfactorily. In one example a method of detecting the silencing of β-actin using anti-β actin (Ambion) and a fluorescein labeled secondary antibody is provided. For a given input siRNA concentration, uniformity in dosage can be evaluated by measuring fluorescent intensity. Then, siRNA mediated silencing efficacy can be determined by assessing the silencing of β-actin using a kit from Ambion®, Inc. The degree of down regulation can be determined via fluorescence intensity measurements. In addition the dose dependence on silencing can be determined. Silencing efficiency has been shown to depend on the amount of siRNA inserted into the cytoplasm. As such, varying amounts of siRNA targeting β-actin can be inserted into cells (0.1-5.0 μg). By looking at the percentage of β-actin expression, the amount of expression inhibition can be assessed.

In one embodiment, the platform described herein is used to efficiently deliver siRNA into cells in a controlled and efficacious manner such that it will silence the targeted gene either completely or partially. It is envisioned that critical therapeutic targets whose silencing can be measured using real time PCR or Western blot can then be investigated.

In another embodiment, relating to the integration of electroporation with the electrophysiology platform described herein, the platform can be used to monitor a cells' seal resistance measurements in real time, thereby allowing determination if the electroporation pulse deteriorates the high seal necessary for patch-clamp measurements. In one embodiment pulse conditions can be adjusted to sustain the pores for a desired time period, either longer or shorter based on conditions. In one embodiment a cell is resealed as quickly as possible to ensure the cell's interior does not diffuse out. However, the time for resealing can be manipulated such that the pores remain open long enough for the desired compound to be introduced.

Material Properties of Microfluidic Chips

In one embodiment, the chip's material properties in terms of adsorption of test compounds onto PDMS is optimized. Compounds potentially can stick to polymer substrates. The polyvinyl tubing used in traditional patch clamp experiments are plagued with the same problem. It becomes problematic when there is a very low concentration of a compound in the elastomer enclosure; some of it will stick to the walls and change the effective concentration. The system described herein has advantages since it is a flow-through system. As such, given enough time, compound concentration in the bulk will equilibrate with concentration on the surfaces, and remain at a desired value. Since residue on the walls might seep back out after a compound is washed away, such can be anticipated by waiting different times between repeats of the same compound applied. Testing with various fluorescent compounds and measuring the change in intensity can be used quantify any seepage. For example, calibration experiments can be run with fluorescent compounds to verify and quantify adsorption at various experimental flow-rates. Additionally, X-ray photoelectron spectroscopy (XPS) of the PDMS material can be performed after flowing the compound through the chip to quantify adsorption. Furthermore, compounds of different charges, molecular weights, lipophilicity and concentrations can be tested to compare adsorption.

Precluding Compounds from Adsorbing onto the Chip's Substrate

In another embodiment, the material properties of PDMS can be altered to improve the amount of compound absorption through the PDMS. For example, it has been shown that by simply varying the ratio of PDMS base to curing agent, a significant reduction in absorption is achieved [Chang, W. J.]. Other forms of surface modification, including selectively depositing a surface coating onto the PDMS is also possible [Shin, Lehnert]. In addition to PDMS other materials can be useful as a chip substrate for use with the system described herein. For example, other polymers such as silicones, fluorinated silicones, Teflon, Nafion, and the like can be used. In addition, glass or quartz can be used. Alternatively, it is envisioned that micromachining of Teflon or use of a hard plastic such as zeonor or to glass could be suitable.

hERG Blocker Screening

In general, in one aspect, a hERG blocker screening platform is provided. Because hERG interaction cannot be structurally predicted, various assays have been developed to screen for possible modulation either in vitro, in vivo, or in animal models. hERG channel activity can be investigated in vitro using transfected cell lines expressing hERG. Channel activity on these transfected cells can then be assayed either indirectly using radioactive tracers, such as Rubidium efflux assay, or directly using voltage patch clamping (manual or automated). The limitation on the tracers is that they can result in many false positives and false negatives, necessitating mandatory manual retests.

Manual patch clamping is the gold standard, affording time resolution and control (both electrical and chemical) over the channels not afforded by indirect assays. The limitation is the very limited throughput (~10 data points/day) and the requirement of a highly skilled trained operator.

Automated patch clamp systems with hERG screening capabilities include Molecular Devices PatchXpress® and Quattro® Pro, Sophion QPatch™, and Flyion Flyscreen®

[Razvi]. These are large, expensive robotic based machines that yield throughputs from 250 to 3000 data points/day. The only two commercially available system for hERG screening affordable to academic researchers is Nanion's Port-a-Patch© and Cellectricon's DynaFlow™ System. The Port-a-Patch© system is a more manual system with limited throughput: each disposable substrate only patches one cell. Cellectricon's DynaFlow™ system is an add-on to an existing patch clamp rig: the cells are still patched manually with a glass pipette. The DynaFlow™ system is comprised of perfusion channels with different compounds loaded and the cells are scanned in front of the different channels for perfusion.

As previously mentioned, the rate limiting step in the screening process is the slow diffusion times, which can far exceed the high-resistance patch seal necessary for the electrophysiology measurements. One approach around this issue is maximizing seal resistance, with the implicit understanding that the seal will degrade over time. While seals of ~200 MOhms are adequate for hERG screening as the potassium channel currents are large (nAmps) [Moore], many systems strive for gigaOhms seals with the orifices such that, even with time dependent degradation, a reasonable seal can be sustained by the time the compound reaches the binding site.

The platform for hERG blocker screening described herein addresses many of the limitations above described systems.

Short Interfering RNA (siRNA) Screening

In general, in another aspect, a rapid siRNA delivery platform is provided. Studies have shown that, so long as functioning siRNA enters the cell, it completely suppresses expression of the targeted gene in that particular cell; ineffective gene silencing has in most cases been attributed to poor delivery [SuperArray Bioscience Corporation]. While lipid-mediated transfection is the most commonly used delivery method, its efficacy is poor for certain cell types such as primary cells. Conventional bulk electroporation is often used for these difficult-to-transfect cell types. With the high inhomogeneous electric fields inherent to bulk electroporation, transfection yields are typically low, with most cells not viable. In the case of transfecting DNA, the cells that are transfected are typically grown back up until ample expression is achieved. Because siRNA does not replicate with the cells, this is not a luxury researchers can afford. Moreover, cell response has been shown in some instances to be siRNA dose-dependent. The rapid siRNA delivery platform described herein addresses these issues. Specifically, the platform can work universally across cell lines, enable rapid transfection, provide real-time feedback and monitoring, provide controllable dosing and improve cell viability.

The three main types of siRNA delivery are lipofection, viral delivery and electroporation. The most common method of siRNA delivery is lipofection, in which the nucleic acid encased in a cationic liposomal or polymer reagent is endocytosed by the cell. However, while lipid-mediated delivery works for many cell types, such as immortalized cell lines, it does not work so well for others, including primary and neuronal cell lines. The lipofection reagent is cell type and concentration dependent, thereby requiring testing various reagents per each new cell line. The siRNA tends to remain in its lipid vessels inside the cell even hours after transfection [Byrom]. The process is therefore slow, typically requiring incubation of a couple of days. Viral delivery systems using lentivirus, retrovirus or adenovirus can introduce siRNA into difficult to transfected cell types, including primary cells. However, infection with viruses could activate inflammatory or antiviral responses that, potentially compromising the intended specificity [Lieberman]. Electroporation is a technique that uses high electric fields to induce structural rearrangements of the cell membrane. Pores result when the transmembrane potential exceeds the dielectric breakdown voltage of the membrane (0.2-1.5V) [Weaver]. Advantages of using electroporation for siRNA delivery include its instantaneous delivery, its ability to transfect hard to transfect cells, and its non-dependence on cell division.

Controlled siRNA Delivery to Multiple Cells Individually

In another aspect, single cell electroporation arrays for controlled delivery of siRNA are provided. A first consideration is the efficiency of electroporation conditions. Typical protocols to deliver plasmid DNA into the cell's nucleus require higher voltages than delivering siRNA into the cell's cytoplasm. For each cell type the ranges of pulse amplitude and of pulse width such that the pores open and reseal (based on impedance monitoring) for siRNA delivery can be determined. The minimum value is one in which there is an initial jump in current. The maximum value is determined by finding the parameters, based on impedance monitoring, at which the pores no longer reseal. To this end, in one embodiment a method is provided for demonstrating that the cell's impedance has returned to its original value for appropriate pulse parameters, and showing that intracellular content has ceased to diffuse back out of the cell through the membrane. Then, the pulse parameters for the optimal dosing of siRNA can be determined as discussed herein.

In one embodiment, pore size and number of pores are determined as a function of time for a given pulse amplitude/pulse width conditions. For a given set of pulse parameters, pore size and lifetime can be used to determine the amount of siRNA entering the cell. Pulse parameters can also determine the survivability of cells post electroporation. A pulse parameter table can be prepared that quantifies siRNA delivery into the cytoplasm and cell viability for each pulse amplitude/pulse width condition. An optimal and repeatable electroporation protocol can be prepared based on empirical cell based experiments. The pulse parameters can first be determined by varying conditions, starting with conditions previously shown to successfully electroporate HeLa cells (e.g., a DC square pulse of ~0.7 V amplitude and 6.5 ms duration). To start the electroporation experiments, the compounds can be loaded into the backside perfusion capillaries and closed off. The rest of the channels in the chip can then be filled with electroporation buffer solution while taking extra care to expel any air bubbles in the tubing. The linear resistance of the open channel can be measured via the amplifier. The cell suspension can then be introduced into the device after trypsinization with a syringe; the injection is controlled to allow cell trapping by applying negative pressure on the trapping channel. Once a cell is trapped, a current-voltage trace program written in, for example, LabVIEW is run to input the specified pulses while recording current at a sampling rate of 10 kHz. A range of acceptable combinations of pulse amplitudes/pulse widths for different cell types (e.g., HeLa, Chinese hamster ovary (CHO), and primary cell lines) and compounds (e.g., of varying molecular weight and charge) can be determined. An optimal condition with respect to pore duration, pore size, compound size, and reseal ability can be determined by fluorescent assays and electrical measurements. With each pulse condition, cell impermeable fluorescent-labeled siRNA can be introduced. From this, the average size of the pores and number the pores can be determined via fluorescence measurements within the cell (based on the number of molecules that accumulate inside the cell). Also, by plating cells on chip post electroporation, cell viability can be determined as a function of voltage application protocol. Based on this, calibration curves can be developed in relation to: pore size as a function of applied potential and cell viability/resealing as a function of applied potential for each cell type. The control can be the introduction of the compounds without applying an electric field. Based on a quantified set-point for starting the electroporation experiments, a real-time feedback control loop can be included. In one embodiment the real-time feedback control loop can monitor current and voltage can be applied accordingly.

A matrix of pulse conditions (amplitude and width) versus cell types can be developed. For each cell type, an acceptable range of pulse conditions such that the membrane porates most of the time and reseals in a timely manner can be established. Because of cell to cell variability, not every cell will be porated successfully using pre-set protocols. Therefore, an electrical monitoring and feedback system can be implemented to ensure the cell is electroporated. If resealing/viability rates are not high enough, adjustments to the electroporation parameters/conditions can be made until suitably high survivability is achieved.

In one embodiment, empirical measurements and parametric analyses can be used to determine dosing conditions. In a particular embodiment the delivery of siRNA into the cytoplasm can be numerically modeled. Such models can be tested by measuring intracellular perfusion of siRNA attached to fluorescent reporter molecules. In one embodiment, a finite element modeling (Femlab) is provided that quantifies the delivery of ligands into the cytoplasm based on the principles of diffusion or diffusion with electrophoresis (depending on delivery method) using the Nernst-Planck equations. The model must correlate with empirical experiments as well as parametric analyses. In one embodiment a method of demonstrating the delivery of a specific siRNA sequence into the cell is provided. For example, a particular embodiment the efficacy of the approach can be shown by real-time monitoring of siRNA delivery into the cell. This can be accomplished by labeling the siRNA sequence with a fluorescent label (e.g., Cy3). Introduction into the cell can thus be visualized, for example Cy3-labeled siRNA can be detected by a red fluorescence visible in fluorescence microscopy or other detection apparatus.

As discussed herein, other embodiments provide for detection of siRNA-induced gene silencing and determination of the dose dependence of gene silencing.

In another embodiment, a method is provided to ensure cell viability after electroporation. In one embodiment impedance measurements can be used to monitor the cell during and directly after electroporation. A critical element in the efficient delivery of siRNA is cell viability. Therefore, in one embodiment real time electrical measurements can be used to monitor the health of the cell and its electroporation condition. It is envisioned that cell membrane resealing can occur at least 95% of the time for, for example, n>10 cells (by monitoring currents at low applied holding voltages over longer time durations). In one embodiment a method of testing for membrane resealing includes incubating the cells in the device for 24 hours and assessing cell viability. For example, in one embodiment a comparison can be made regarding cell viability after electroporation of primary cells versus immortalized cells. Viable cells should plate in the device. Non-viable cells would not plate and can be washed away. In another embodiment it can be assessed whether cells plate at least 80% of the time after electroporation when measured after 24 hours. The viability of various cell lines can be compared and electroporation conditions can be recalibrated to optimize cell plating post-electroporation.

In one embodiment optimal buffer conditions are provided to ensure proper osmotic balance. In a particular embodiment to ensure the cell's intracellular vital constituents are not fatally depleted, buffer condition can be varied. Optimal buffer conditions may be different depending on the cell type. In one embodiment real time electrical measurements can be used to monitor the health of the cell and its electroporation condition. For example, using a patch-clamp amplifier system, the voltage can be clamped and the current can be measured. Low applied voltages (e.g., 10 mV) can be used to monitor the current response immediately after the electroporation for extended periods of time (e.g., minutes) to ensure resealing.

Controlled siRNA Delivery Via Single Cell Electroporation Arrays

Figure 37:
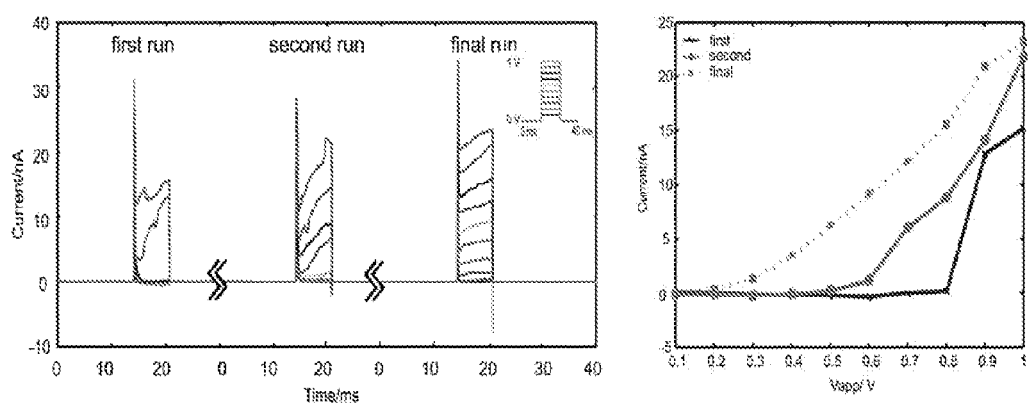
FIG. 37 shows graphs providing evidence of reversible electroporation.

In a test study, siRNA was introduced into HeLa cells. Seventeen HeLa cells were sequentially electroporated using a pulse duration of approximately 6.5 ms. A characteristic 'jump' in current was observed in 15 of the 17 cells. The voltage was varied from 0 to 1 V in 0.1 V intervals (FIG. 37A, inset), in order to determine the threshold voltage required for electroporation. A typical resulting current trace from one of the cells is shown in FIG. 37A. Leak current, i.e. the current that goes around the cell because the seal resistance is not infinite, was subtracted to isolate the current across the cell. The leak resistance, Rleak, was measured for each cell from initial current traces at low voltages and assumed to be constant (about 35 MΩ). A significant jump in current was evident at 0.8 V. The average applied voltage of electroporation for the 15 cells that show jumps was 0.76±0.095 V. The average transmembrane potential for the population of cells was 0.51±0.13 V. This is within the voltage range (0.2-1.5 V) of dielectric breakdown suggested by most published data [Weaver, Haas].

The data also provide evidence for the occurrence of cell resealing. Resealing was observed within 60 seconds (time between runs); this is within the range reported for phospholipid bilayers to reseal [Nolkrantz (Functional Screening)]. After the first sequence of pulses was applied, the membrane was permeated as the current jumps to a relatively high level (FIG. 31). However, when the second sequence of pulses was applied after 60 seconds, small applied voltages (<0.6 V) again result in very low currents, similar to those of the first sequence of pulses. The most likely explanation for this is that the pores shrink after release from the electric field. In the subsequent run, the current jump occurred sooner than in the first run because the pores still exist; therefore, it is easier to reopen them with the electric field than to create new ones. The final run in the sequence is presented to compare the resealing capabilities with the more linear response of a cell that has lost its ability to reseal (FIG. 37B).

In another study the ability to culture the cells on chip was demonstrated (see FIG. 36). This lays the foundation for culturing the cells immediately following electroporation/siRNA introduction—right at their trapping sites. Such an approach would eliminate the time consuming and difficult step of transporting the cells from the electroporation cuvette to a cell culture chamber.

Figure 38:
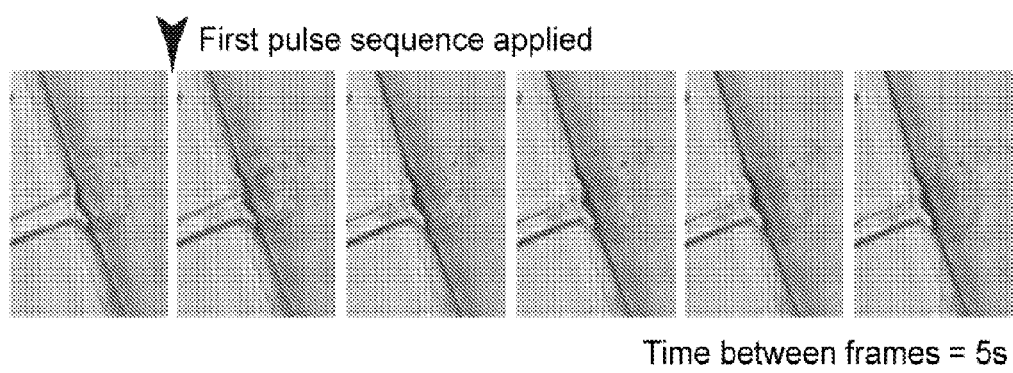
FIG. 38 shows photomicrographs of a cell undergoing electroporation in the presence of a dye using a microfluidic device according to specific embodiments of the invention.
Figure 39:
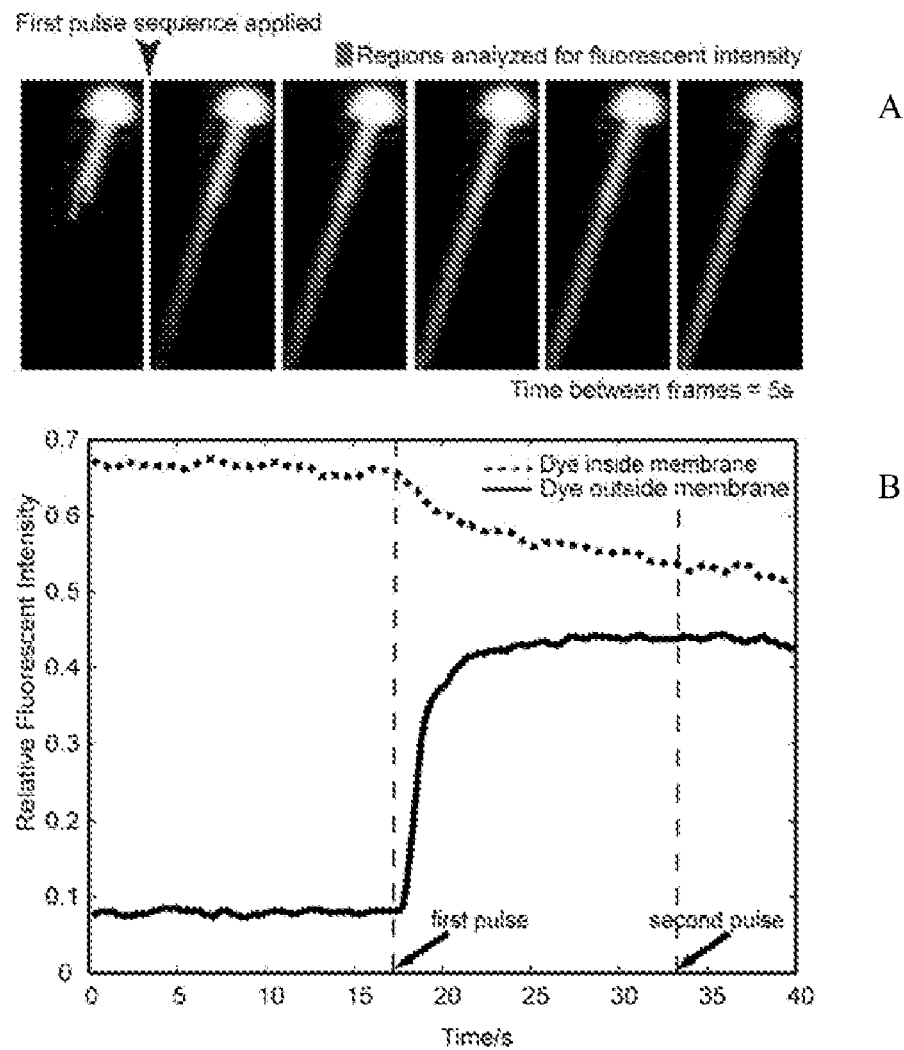
FIGS. 39A-B are respectively a photomicrograph and graph relating to a cell undergoing electroporation in the presence of a dye using a microfluidic device according to specific embodiments of the invention.

As found in a further study, in addition to electrical measurements, time-lapsed images show electroporation and introduction of material into the cell based on Trypan blue dye movement into the cell (FIG. 38) and Calcein dye out of the cell (FIG. 39). The color of the membrane impermeant dye Trypan blue is normally undetectable at low concentrations; once the membrane is permeabilized the dye can accumulate within the cell, a dark blue color becomes apparent. Therefore, by using the Trypan blue assay, the electro-permeated area can be readily visualized. Calcein dye movement through the porated membrane over time is shown in FIG.

39A. It can be seen from the fluorescent images that the trapped cell is porated when the pulse sequence is applied. It is clear that the dye is escaping through the cell membrane within the channel indicating maximum pore formation over that region. The fluorescent dye begins to escape within 1 second after the pulse. Analysis of the changes in fluorescent intensities of one of the cells is presented in FIG. 39B. The interval between frames is 5 s, and the pulse sequence is applied after the first frame. The initial non-zero intensity outside the membrane indicates some background fluorescence in the system. Rapid (within 3 s) initial convergence of the intensities within the trapped region (Intinside) and outside the trapped region (Intoutside) indicates that the pulse application creates pathways for dye diffusion across the membrane. The delay between the initiation of the drop (Intinside) and the initiation of the rise (Intoutside) is believed to be due to the time delay required for the dye to escape the membrane. It should be noted that the fluorescent intensities Intoutside and Intinside do not completely converge even after repeated voltage application. This is likely due to Calcein dye binding to cytoplasmic structures. The fluorescent signal does not provide information about membrane resealing because dye concentrations within and outside of the cell reach equilibrium after the first pulse sequence is applied. The majority of dye transfer occurs after the short voltage pulse, indicating that diffusion is the predominant transfer mechanism. This is in agreement with previous observations [Neumann]. The fluorescent intensity curves do not completely converge even after repeated runs, suggesting calcein dye binding to cytoplasmic component. The fluorescent result does not provide information about membrane resealing because the dye diffusion reaches equilibrium after the first pulse sequence. The 'second run' thus has no effect on the dye gradient.

Figure 40:
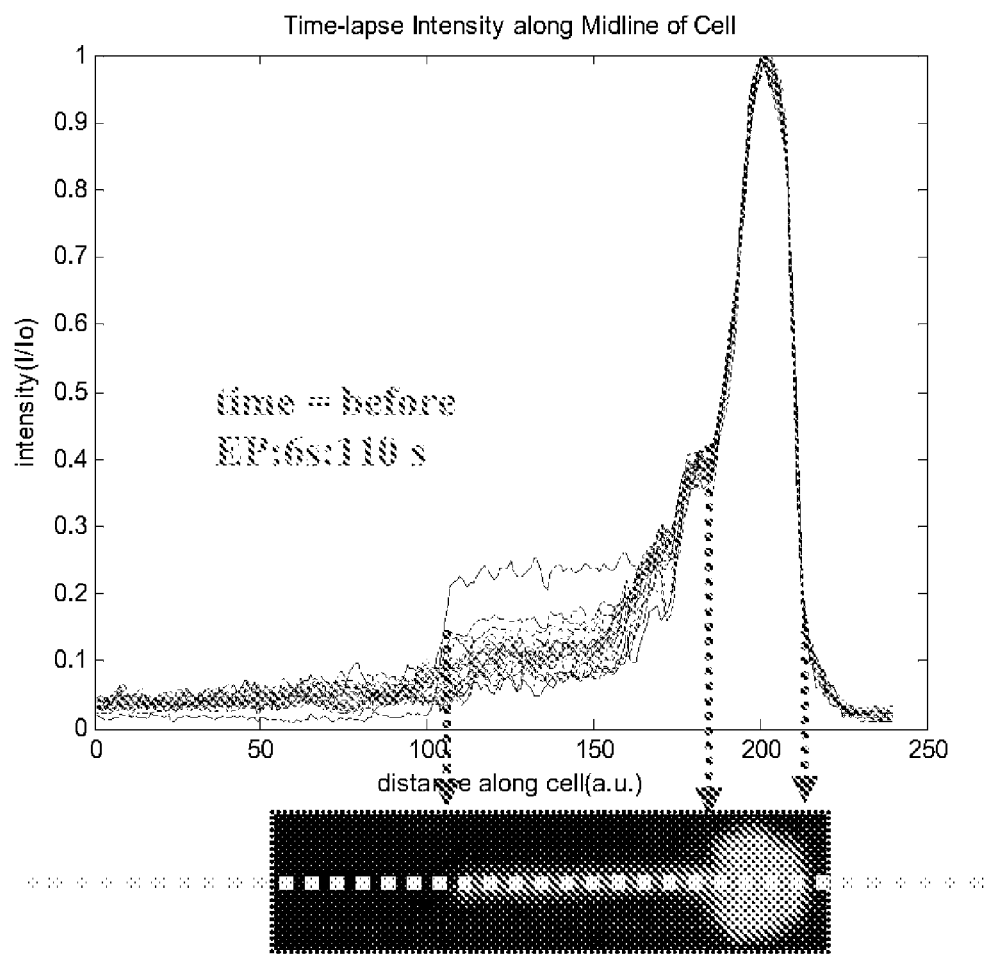
FIG. 40 is a graph relating to a cell undergoing electroporation in the presence of a dye using a microfluidic device according to specific embodiments of the invention.

A closer look at the diffusion mechanism is presented in FIG. 40. A cell preloaded with Calcein was electroporated and the intensity of the cell along its midline was plotted over time. Immediately after electroporation, it is quite apparent that the magnitude and slope of the intensity at the porated membrane changes as the dye is now allowed to diffuse out of the cell.

Shear Stress Assays

A further application area for microfluidic devices integrated with fluid reservoirs is the measurement of cellular adhesion and/or rolling to a substrate of choice. Microfluidics and precise flow control permit the generation of statistical data on cellular adhesion and response to shear stress.

Figure 42:
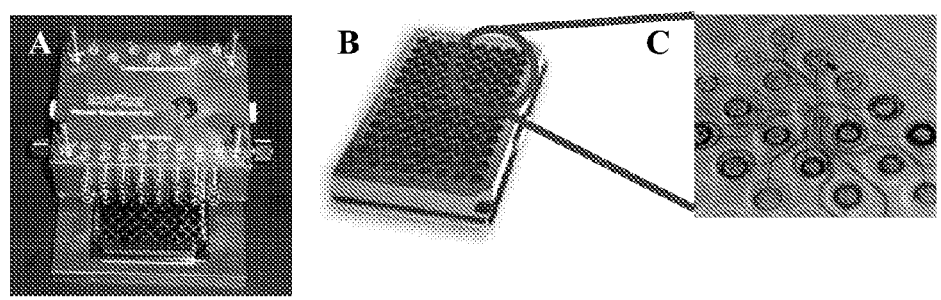
FIG. 42A illustrate an exemplary layout for a microfluidic device and a pressure interface.
FIGS. 42B-C illustrate an exemplary microfluidic device and plate combination of the invention.

An exemplary layout for the microfluidic devices is presented in FIG. 42. In one embodiment, the device consists of a microfluidic layer bonded to a plate structure containing reservoirs. The microfluidic layer may be irreversibly bonded to the plate structure. The upper structure of the device can be an essentially flat plate with holes disposed therein. The holes are used as reservoirs and may serve for loading of the particle sample, cell growth media and any other compounds required in the experiment. The top plate may then be irreversibly bonded to a microfluidic layer containing microscale channels, such that access ports to the said channels are within the bottom of said reservoirs. After the particle suspension in introduced in the microscale channel, imaging may be performed in the shear assay observation area (FIG. 42) as a readout of particle characteristics. The characteristics may be particle adhesion or, if cells are being used, cell motility, morphology and fluorophore distribution within the cell volume.

In general, in one aspect, the invention provides a method for measuring the characteristics of particles in the presence of shear forces including: dispensing a particle suspension into on or more wells of a microfluidic device, introducing said suspension into one or more microfluidic channels of the device, providing flow (e.g. driving flow) through one or more of the microfluidic channels, and may include measuring a characteristic of the particle suspension before, during or after the application of flow. In one embodiment the invention may be applied to particles including beads, cells, bacterial cells, vesicles, oocytes, collections of cells and embryos. In some embodiments, the flow in the apparatus of the invention is laminar flow.

In a particular embodiment of the invention, the microfluidic device consists of a perforated plate containing wells irreversibly bonded to a microfluidic layer containing microscale channels, and wells of the perforated plate may be in fluidic contact with the inputs/outputs of microscale channels of the microfluidic layer.

In general, in one aspect flow is driven by applying a pressure or vacuum to the air-fluid interface in the wells of the microdevice or by an electrokinetic force.

In one embodiment of the invention, the microfluidic channels are defined as having heights generally between 0.1-500 um and widths of 1-2000 um. In another embodiment of the invention, the microfluidic channels are defined as having heights generally between 10-100 um and widths between 40-500 um.

In general, in one aspect, the measurement of the particle characteristics may be based on acquiring images of the particle suspension before, during and/or after applying flow. Images may be acquired while particles reside in a section of a microfluidic channel. In one embodiment, the measured characteristic of the particle suspension may be selected from the group consisting of: measuring the adherence of particles to substrates during flow, measuring the adherence of flowing particles to static substrate-bound particles during flow, measuring the detachment of particles due to flow after an initial static attachment period, measuring the migration of particles during flow, and measuring the morphology of particles.

In general, in one aspect, the invention provides for a device for performing shear force experiments at multiple shear rates including a microfluidic layer that may containing a channel that is irreversibly bonded to a plate containing reservoirs, a microfluidic channel that branches into a number of microfluidic channels of different fluidic resistance, and may contain an observation area in which the different channels exhibit different shear forces simultaneously.

As illustrated in FIG. 3, a pressure interface may be reversibly attached to the microfluidic device via a gasket, and serve to apply pressure to the air-fluid interface in each of the wells. In this embodiment (FIG. 3), a gasket is used in conjunction with mechanical pressure applied in order to provide an essentially air-tight seal between the tubing connected to the interface and the reservoirs in the upper part of the microfluidic device. In other embodiments, the gasket may be sealed to the plate by applying a vacuum in the space between fluid reservoirs, which will initial a tight seal between the said gasket and the rim of the reservoirs (FIG. 15B). As previously described, the reservoir structure is irreversibly bonded to a microfluidic layer where the assay takes place. Tubing connects the interface to a pressure source and both air and fluid may be driven through the system by applying a differential pressure.

Figure 44:
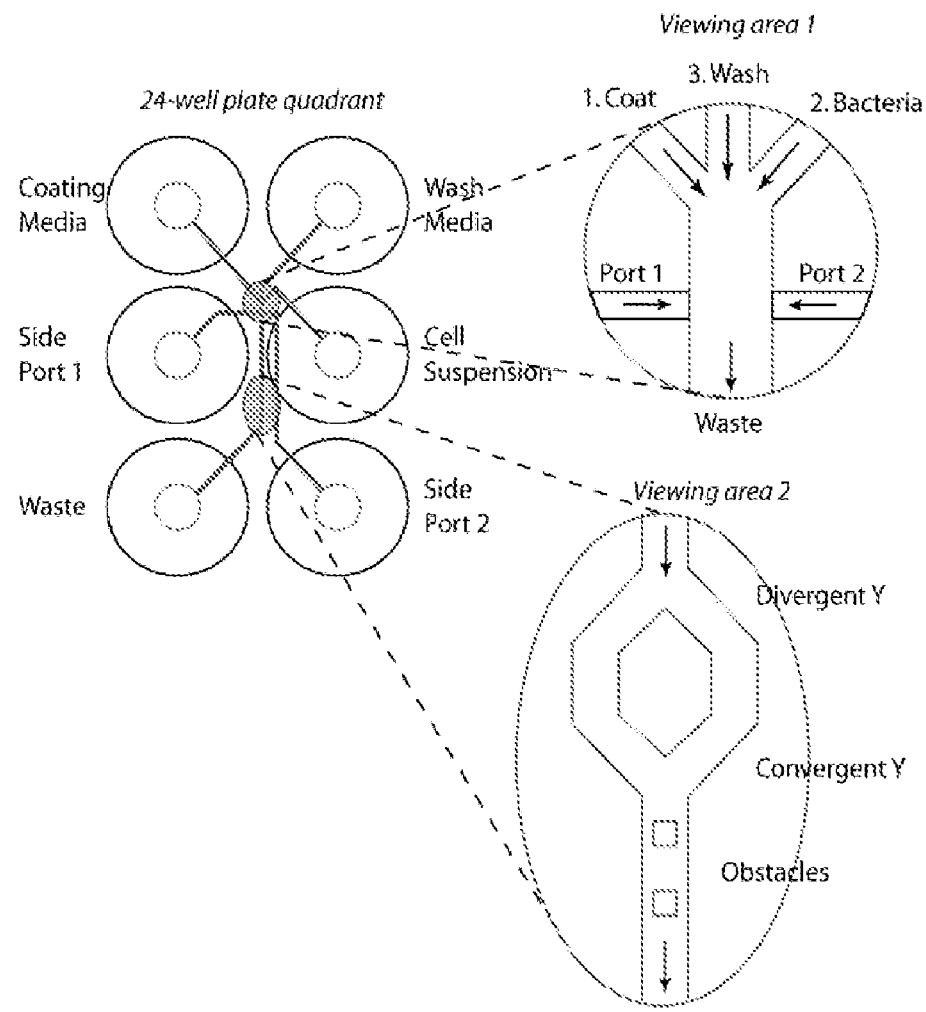
FIG. 44 presents a proposed layout for a 6-well quadrant of a standard 24-well plate of one embodiment of the invention.

One embodiment has been reduced to practice, and an image of this interface design is shown in FIG. 44, along with a device mounted in the interface. The general layout of the interface is described in a previously filed provisional patent application Ser. No. 60/744,034, filed Mar. 31, 2006, which is incorporated herein by reference in its entirety. In the present case, the reservoir structure is a bottomless 96-well plate bonded to a microfluidic layer. A view from the bottom of the plate (Zoom-in) shows an exemplary fluidic layout for a 24-well section of the plate (1 quadrant) in this embodiment. In this embodiment, each plate quadrant acts as an independent device, meaning that 4× experiments may be run on any 96-well plate. The observation region is the section where all of the side channels meet, at the bottom of a well which is not being used as a fluid reservoir.

Figure 43:
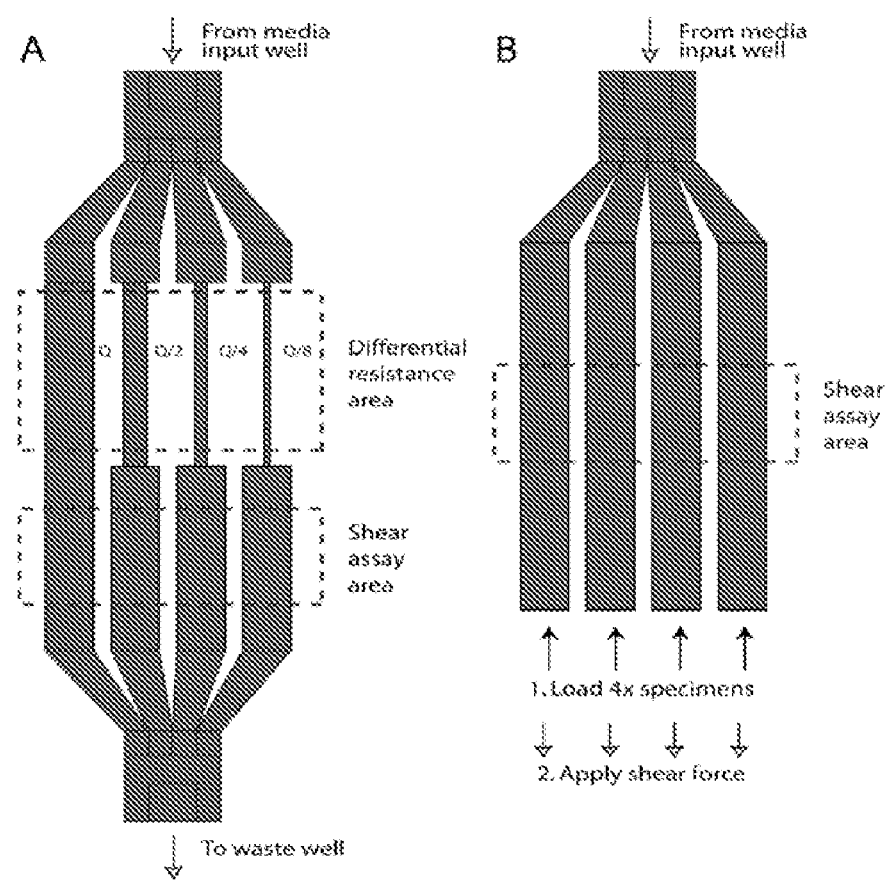
FIGS. 43A-B illustrate alternative microfluidic device designs of the invention.

As illustrated in FIG. 45, higher experimental throughput and parallelism may be achieved by implementing microfluidic designs that have a few different experimental parameters being assayed in parallel. Although 4 channels are illustrated in FIG. 45, it is envisioned that any number of channels can be included, for example, 2 or more channels, 4 or more channels or 8 or more channels. An exemplary design for assaying 4 different flow rates on the same specimen is shown in FIG. 43A. A branch point is provided along the main channel where it splits into a number of different fluid paths. Each fluid path has a different fluidic resistance, imposed by differing cross sectional branch dimensions in a section labeled 'Differential resistance area'. In the design FIG. 43A the resistances are matched such that the flow in each channel is a fraction of the flow in the largest channel, Q. Accordingly, flow rates of Q, Q/2, Q/4 and Q/8 are sampled simultaneously. In the 'shear assay area' (See FIG. 43A), which may be under microscope observation, all branches can optionally include the same cross sectional area. The channel walls (and particles) experience a shear force proportional to the total flow rate in this region. A number of other designs for looking at different shear forces simultaneously may be employed, such as those described by Lu, et al (2004).

Another exemplary design for observing a number of different specimens under the same shear force is shown in FIG. 43B. In one embodiment, 4 different specimens from wells connected to bottom channels are loaded, one in each branch of the main channel. Subsequently, the flow direction is reversed and they are exposed to the same media/shear rate by flowing from the top channel, with data collected from the shear assay area. This is similar to a design described by Lu, et al. (2004), with the exception that each channel is fluidically connected to a well. An important variation of this design is an embodiment where each of the branches containing a specimen has its own input and output well, such that there is no mixing. The application of pressure can still be multiplexed however, with each well receiving pressure (e.g., Vacuum) from the same pressure input and remaining in air pressure communication throughout the experiment.

As illustrated in FIG. 44, in other embodiments, the upper structure of the microfluidic device may follow the layout of a 6-well quadrant of a standard 24-well plate. The device is also meant to perform shear force assays on cells, but the larger input/output channels provide the possibility for long-term unidirectional media flow (and shear force application) without the need to refill channels. Input wells are used for channel coating, cell seeding, and shear media. As illustrated in FIG. 44, the junction of the different input channels, as well as side ports can be observed in 'viewing area 1'. In this embodiment, the 3 input ports are used for coating media, inoculation media containing a cell or other particle suspension and for media used to apply flow and shear to the particles. Side ports are used to apply compounds. As illustrated in FIG. 44, a second viewing window may be used to observe the response to more complex flow profiles ('viewing area 2'). This layout is designed to accommodate individual experiments on a specific cell type with a good amount of flexibility, including Y junctions and flow obstacles to obtain turbulent flow. All of the main channel inputs (e.g., inlets) and compounds can be routed to the 'waste' well.

In general, in one aspect, the invention provides a method for performing multiple shear experiments including: the introduction of a particle suspension into a number of branches of one microfluidic channel, the application of a shear force to said particles by applying flow in the channel branches, and the measurement of a characteristic of the said particles in response to the applied shear forces.

Particles used in the assay may be selected from the group consisting of beads, cells, bacterial cells, vesicles, oocytes, collection of cells and embryos. In one embodiment of the invention, measurement of the particle characteristics may be based on acquiring images of the particle suspension before, during and/or after applying flow.

In one embodiment of the invention, images may be acquired while particles reside in a section of a microfluidic channel.

In general, in one aspect, the invention provides for measurements wherein the measured characteristic of the particle suspension can include: measuring the adherence of particles to substrates during flow, measuring the adherence of flowing particles to static substrate-bound particles during flow, measuring the detachment of particles due to flow after an initial static attachment period, measuring the migration of particles during flow, and measuring the morphology of particles.

In general, in one aspect, the invention provides a device for measuring the effects of shear forces on a number of different specimens which may include: a plurality of microfluidic channels in fluidic communication with a number of wells in a perforated plate; wherein the microfluidic channel dimensions are such that an applied pressure to one of the wells results in essentially the same shear force being applied to the interior channel surfaces; and a section of the said microfluidic channels with dimensions larger than said specimens where essentially same shear force is applied to the interior channel surfaces.

In general, in one aspect, the invention provides a method for measuring the effects of shear forces on a number of different specimens including: dispensing a plurality of specimens into the wells of a microfluidic devices; introducing the plurality of specimens into microfluidic channels of the said microfluidic device, applying essentially the same shear force to said specimens simultaneously by providing flow through the microfluidic channels. The method may include measuring a characteristic of said specimens before, during and/or after the application of flow. The method may include using a microfluidic device including a perforated plate containing wells irreversibly bonded to a microfluidic layer containing microscale channels.

In one embodiment the method may apply to specimens including beads, cells, bacterial cells, vesicles, Oocytes, collection of cells and embryos.

The methods described herein may use a microfluidic device including a perforated plate and a microfluidic layer, wherein the wells of the perforated plate are in fluidic contact with the inputs/outputs of microscale channels of the microfluidic layer. Flow within the microfluidic device may be driven by applying a pressure or vacuum to the air-fluid interface in the wells of the microdevice. In another embodiment, flow may be driven by an electrokinetic force. In one embodiment of the device, microfluidic channels are defined as having heights between 0.1-500 um and widths of 1-2000 um.

The device may be used for measurements of particle characteristics based on acquiring images of the particle suspension before, during and/or after applying flow. Such images may be acquired while particles reside in a section of a microfluidic channel. Further, the measured characteristic of the particle suspension may belong to a group which includes: measuring the adherence of particles to substrates during flow, measuring the adherence of flowing particles to static substrate-bound particles during flow, measuring the detachment of particles due to flow after an initial static attachment period, measuring the migration of particles during flow, and measuring the morphology of particles.

In general, in one aspect, the invention provides a method for measuring the effects of compounds on particles under shear stress, including: dispensing a suspension of particles into one or more wells of a microfluidic device; dispensing one or more compounds into wells of the microfluidic device; introducing the said particles into microfluidic channels of the said microfluidic device; applying shear forces to said particles by providing flow through the microfluidic channels; exposing said particles to compounds either before, during or after the application of shear stress, and measuring a characteristic of said specimens before, during or after the application of shear stress and compounds.

In general, in one aspect, system designs are provided a complete, easy-to-use solution for studying biofilms under shear. The system comprises an instrument with software control and replaceable, sterile multi-well plates (BioPlates) that contain all fluidics. All reagents, including media, inoculant, and test compounds, are pre-loaded in the wells for long-term unattended operation. Fluxion's pneumatic fluid control design eliminates the need for cumbersome fluid-filled tubing.

In one embodiment, the included temperature control system ensures that the flow chamber is kept at the proper temperature for optimal growth and study. The BioPlates include microfluidic channels for inoculant and media addition, biofilm formation, and compound addition. Precise shear rates are maintained by the system's advanced electronic pressure control system. Each BioPlate is constructed with a cover-slip glass bottom to ensure optimal microscopic image quality. Each BioPlate is designed to run either a single or multiple experiments, with as many as 4 experiments running simultaneously to increase experimental throughput.

One example of the system provided can include the following benefits. Ease of use: The BioFlux system is a complete solution, with all components necessary to set up and run biofilm experiments. Sterile fluidics: All fluid paths can be contained within a fully disposable BioPlate that can be supplied fully sterilized—obviating a need for autoclaving of tubing, fittings, and flow chambers. Flexibility: the BioFlux system can support, for example, shear stress changes, automatic inoculation and media addition, automatic compound addition and removal at specified time points, and simultaneous running of a control channel. Easy operation: A simple, intuitive graphical user interface can be included that allows multiple protocols to be established and retrieved easily. A user need only specify, for example, the desired shear rate profile, inoculation period, and timing of compound addition. All system control can be handled automatically. Automated Imaging: BioFlux software can initiate multi-wavelength image acquisition and storage at user-specified intervals.

One example of the system provided has the following specifications:

| System | |
| --- | --- |
| Layout | Main control box with flexible connection to plate interface. Disposable microfluidic 24-well plates mount in interface. |
| Microscope stage support | System mounts to standard inverted microscopes |
| Instrument Control | BioFlux software |

| -continued | |
| --- | --- |
| Instrument-computer connectivity | USB cable (included) |
| Flow control | Pneumatic pressure via 0.2 um filtered sterile air |
| Plate-interface seal | Single-use sterilized gasket. Interface connects to ½ of plate at a time. |
| Power requirement | 100-240 V AC, 50/60 Hz, 2 A |
| System dimensions | 12" × 10" × 12" |
| | System Control |
| Software | Windows 2000 and XP compatible |
| Inoculation, media, and compound addition | Automatic. Protocols defined as storable methods in software. |
| Manual override of software | Included. |
| Data capture | Automatically saves flow rate data at user-selected frequencies |
| Image Control | Automatic imaging trigger output for time-lapse imaging |
| | BioFlux Plates |
| Plate format | SBS standard 24-well plates, 3 ml volume per well |
| Materials of construction | Polystyrene, PDMS, glass |
| Flow chamber imaging | Flow chamber bottom is 170 um cover slip glass |
| Media filtration | 0.2 um filter at media well outlet |
| Experimental format | 4 experiments per half plate, including one control |
| Compound addition wells | 3 per half plate + 1 control |
| Plate temperature control | Included, ambient to 37° C., programmable |
| Flow chamber dimensions | 6 mm (length) × 200 μm (width) × 50 μm (height) |
| | Performance |
| Run time | 128 hours at 10 dyn/cm² |
| Refill capability | <1 minute by raising interface manually |
| Shear rate range | 0-50 dyn/cm² |

This method may make use of a microfluidic device including a perforated plate containing wells irreversibly bonded to a microfluidic layer containing microscale channels. Fluidic inputs may be provided by wells of the perforated plate are in fluidic contact with the inputs/outputs of microscale channels of the microfluidic layer. In one embodiment, microfluidic channels are defined as having heights between 0.1-500 um and widths of 1-2000 um. Further, the method may be applied to particles belonging to a group including of beads, cells, bacterial cells, vesicles, Oocytes, collection of cells and embryos. In one aspect of the invention, measurement of the particle characteristics is based on acquiring images of the particle suspension before, during and after applying flow and before, during or after exposure to compounds. In one aspect of this method, the measured characteristics of the particle suspension belongs to the group of: measuring the adherence of particles to substrates during flow, measuring the adherence of flowing particles to static substrate-bound particles during flow, measuring the detachment of particles due to flow after an initial static attachment period, measuring the migration of particles during flow, and measuring the morphology of particles.

In one embodiment, flow in the device is driven by applying a pressure or vacuum to the air-fluid interface in the wells of the microdevice. In another embodiment, flow is driven by an electrokinetic force.

In one aspect of this method, images are acquired while particles reside in a section of a microfluidic channel.

In general, in one aspect the invention provides for a system for performing shear force experiments on particles, including: a microfluidic device containing one or more microfluidic channels irreversibly attached to a plate containing reservoirs; a flow actuation system that can introduce a population of particles into a microfluidic channel; a flow actuation system that can apply shear stress to said particles; a measurement system for determining one or more characteristics of the said population of particles. For this system, particles may be selected from the group consisting of beads, cells, bacterial cells, vesicles, oocytes, collection of cells and embryos.

In this system, the microfluidic channel may be part of a microfluidic network. In one embodiment, the inlet and outlet of the microfluidic channel(s) are in fluidic contact with said reservoirs. One useful configuration contains wells disposed in a standard well plate format, for example, 6-well, 24-well, 96-well, 384-well, or 1536-well plates.

Further, in one embodiment, the flow actuation system consists of a pressure application apparatus. In another embodiment, the flow actuation system consists of an electrokinetic flow apparatus.

In one embodiment of the system, the measurement acquisition solution includes an imaging acquisition system including of a standard microscope equipped with a CCD camera. In another embodiment, the measurement acquisition system includes a microscope objective and a CCD camera, mounted in an enclosure. The enclosure may be a microscope chassis, and the image analysis system may include a microprocessor and a software application.

In one embodiment of the system, the measurement of the particle characteristics may be based on acquiring images of the particle suspension before, during and/or after applying flow. The measured characteristic of the particle suspension may belong to a group consisting of: measuring the adherence of particles to substrates during flow, measuring the adherence of flowing particles to static substrate-bound particles during flow, measuring the detachment of particles due to flow after an initial static attachment period, measuring the migration of particles during flow, and measuring the morphology of particles.

In one embodiment, the interface may be placed on top of most inverted microscope stages, or can be part of a custom imaging system. In one embodiment of the system, well plates are used and one quadrant is used at a time, each quadrant representing an independent device. For example, in a 24-well footprint, 6 wells are contained in a quadrant and constitute a device, and typical operation can proceed as follows:

For experiments that require pre-coating of the channel surface before cell attachment, the solution can be loaded into the 'coating media' well and incubated in the channel over the needed time frame. A particle suspension is then loaded in the disposable microfluidic cartridge 'input' well, as well as media for applying shear flow in the 'wash' well (See FIG. 44).

After the coating time has elapsed, the particle suspension (cells, bacteria, platelets, leukocytes, etc) may be flowed into the observation area of the cartridge. The experiment can then be performed as desired, depending on whether it is an adhesion, removal or mechanotransduction experiment. Both the sequence of compound introduction and flow rates may be controlled from the software interface, and programmed ahead of time.

In one embodiment, time lapse images of the cells under shear stress are acquired on the user's own microscope for later analysis. If multiple locations in the flow channels need to be monitored, an automated stage can be used to move the objective to the monitoring sites.

Multiple locations in the microfluidic network can be used to assay different responses of the same seeded population. Some examples are: different flow rates, different flow patterns, and applied compounds. Compound application to selected regions of the main flow channel can be performed by applying pressure to the two side ports (see FIG. 3). The advantage of this design is that any compound effect has a built-in control experiment in the region upstream of the compound introduction channel.

A useful design for high throughput experimentation on bacterial biofilms is exemplified in FIG. 45. In a first embodiment (see FIG. 45A), each pair of wells (1, 2) can be used as a separate experiment. Bacteria can be loaded into the input well (1), and driven through the connecting channel to the outlet well (2) in order to establish a biofilm under flow in the microfluidic channel. The interface can then be removed, and a compound of interest can be dispensed into the inlet well (1), and flowed through to determine biocide efficacy. Flow can be either unidirectional or bi-directional, and each channel may be observed over time on the stage of a standard inverted microscope. In a second embodiment (see FIG. 45B), a set of three wells form an experimental unit. Well (3) may be loaded with a compound of interest. The inlet well can be loaded with bacteria of interest and flow driven to the outlet well (2) resulting in biofilm growth in the channel. Addition of a compound of interest by providing flow from well (3) may be used to assay compound activity without the need for disengaging the interface.

An exemplary embodiment of the full experimental system setup used is illustrated in FIG. 5. The microfluidic device (1) is contacted by the pressure interface (2) and controlled by a custom pressure controller (3) that controls flow patterns within the microfluidic network. In turn, the controller accepts programmable signals from a microprocessor device (5) that can determine flow patterns in the microfluidic device. The assay methodology may also include a standard microscope setup or custom optical setups meant to record images of the particle suspension under shear stress inside a microfluidic channel.

An exemplary system for data recording by a microprocessor device and transmission thereof over a network is presented in FIG. 4. The microprocessor device may be used to control experimental analysis, as well as to acquire and analyze assay data. The data may in turn be transmitted to a remote user via either a communication medium or a data storage medium, such as disk storage.

In one embodiment, a microfluidic system is provided including a structure including a plurality of bottomless reservoirs; a substrate comprising microfluidic channels on one side, said substrate coupled to the structure with the channel side facing the substrate, and the microfluidic channels in alignment with the bottomless reservoirs of the structure such that the reservoirs of the structure are in fluidic communication with the microfluidic channels.

In another embodiment, a microfluidic device is provided including a structure including a plurality of reservoirs, a substrate coupled with the structure and comprising one or more main flow channel, a plurality of trapping channels and a detection zone for viewing cells microscopically, wherein one or more reservoir is in fluid communication with one or more trapping channel, and wherein each trapping channel is in fluid communication with one or more main flow channel, and wherein the detection zone is adapted for viewing cells using an upright microscope or an inverted microscope.

In the proposed system, microfluidic device design is used to modulate flow patterns and apply reagents during shear force experiments. The fluidics are mated to standard well plates for ease of use and fluid path sterility. The plates may be disposable or reusable. This system can be utilized for a number of cellular biology experiments where control of shear forces is paramount. Some examples include applications involving bacterial biofilms, platelet adhesion, neutrophil adhesion, cell adhesion, motility and migration, as well as tumor cell adhesion. Other examples of applications are neurite outgrowth, chemotaxis, selective cell trapping via adhesion.

In current practice, such experiments are chiefly based on larger, reusable laminar flow chambers (Brown and Larson, 2001). Disposable polystyrene flow chambers have been introduced recently but at large per experiment cost (approx. $60) and limited value added features (straight laminar flow, single flow rate).

The advantages of one embodiment of the microfluidic system of the invention can be divided into two categories: workflow advantages and unique features. Workflow advantages include a change from common practice where the functionality of the device is comparable to that of laminar flow chambers, wherein the ease of use and simplicity of the experimental setup of the invention lead to increased productivity. Unique features include access to new parameter space for shear force experiments and the implementation of parallel microfluidic designs that result in dramatic throughput increases for certain classes of experiments. Both categories are described below. Multi-shear experiments conducted simultaneously on the same cellular system at a variety of flow rates is enabled by designs where the branches of the same channel have different flow rates in the observation window (see FIG. 2A). A 4 point shear curve can be created quickly by performing a single experiment. Multi-sample experiments (e.g. using a number of different cellular samples, including mutants of the same bacterial organism) can be introduced in each branch. Because all branches are driven from the same pressure source, each specimen can be provided the same shear rate and differences in adhesion/migration can be readily quantified. Expanded range of laminar shear is supported since flow in the small channel dimensions (approx. 1/10 the height of regular flow chambers) remains laminar in the channels to much higher values (i.e. 40 $dyn/cm^2$). Biomimetic flow profiles can be provided as found in vivo in the vasculature. This is useful since a number of bacterial seeding/infection events happen at branches in the vasculature. The disclosed microfluidic designs can mimic such branch points, increasing the physiological relevance of the results. Flexible, computer controlled flow time course can be provided. In one embodiment, the flow control system uses pressure actuators that can be operated in real time from the software interface. As such, complex time dependent flow can be programmed in. In addition to the application time and magnitude of laminar flow, time dependence can be used to mimic cardiovascular flow profiles or create more complex flow ramps.

In respect to throughput, a number of workflow advantages are envisioned. One proposed embodiment of the invention provides a fully contained, disposable fluid path. Because the consumable microfluidic plates of the invention can contain both microfluidic channels and standard well plate reservoirs, the fluid path is fully enclosed in the disposable cartridge. This provides for simple sterilization and safe disposal of all wetted surface. The pressure interface does not come in contact with fluid under normal operation (see FIG. 3). Plates be provided sterilized and sealed. Reductions in cellular and reagent requirements are envisioned. Severely reduced chamber dimensions result in small dead volumes and low consumption during flow. Overall, the reduction in reagent requirements can be about 1000-fold. Online compound addition can be provided. Branched channels provide the ability to apply compounds at will to the cell attachment surfaces in a time resolved manner (see FIG. 46). This will aid in a wide range of studies elucidating cellular response to chemical stimuli under shear stress. Parallel interface and software controlled protocols are also provided. An interface and pneumatic control system can provide a pressure interface to all of the channel input/outputs (e.g., inlets/outlets) at once. In one exemplary embodiment, when connected to the computer controlled pressure actuator, any of two or more user selected pressures can be applied to any six or more channel inputs simultaneously, setting flow/compound application parameters.

Experiments using embodiments of the invention have been achieved with bacterial biofilms. Biofilms can be formed by bacterial populations attached to the walls of the shear flow channel; they typically form an organized architecture and exhibit antibiotic and biocide resistance. Channels of the device were coated with plasma proteins by introducing a plasma protein solutions into the device and incubation at 37° C. Post incubation, the flow channel was inoculated with bacteria (*pseudomonas flourescens, pseudomonas A.*) by introducing a bacterial suspension into the channel and incubating for 30 minutes. After bacteria adhesion, resistance to shear was assayed. Fluid flow was controlled using a pressure regulator to drive fluid through the device at calibrated velocity and shear rates. Venous flow was initiated (shear stress of 2 $dynes/cm^2$) and adherent bacteria were imaged in a 60 minute time series at 37° C. using epifluorescent microscopy. It was determined that different bacterial strains have different resistance to shear stress, and that attachment/detachment kinetics can be observed in the devices using standard microscopy techniques.

A number of different biofilms grown in the device are shown in FIG. 46. Representative biofilms supported are *pseudomonas aeruginosa* (A), *pseudomonas flourescens* (B), and *candida* (C), yeast—a fungus (see FIG. 46).

Interface and Pneumatic Control of a Microfluidic Shear Force Apparatus

FIG. 48 is illustrative of a useful system diagram for the shear force apparatus. One embodiment of the proposed product would consist of the following components: (A) a disposable microfluidic device including input and output well(s) and a microfluidic channel connecting the two, (B) an imaging system including a standard microscope, (C) a pressure interface to the microfluidic device that connects to (D) a computer controlled pressure source. A PC can be used to control shear force and acquire images from the microscope's camera. The acquired image stack (both bright field (BF) and fluorescent data) is then processed in order to determine rates of adhesion/removal from the channel walls, as well as the response of cells to shear forces. Cellular response can be assayed using a variety of methods from morphology and motility determination to genetic and protein expression profiles of the cells after a period of applied shear force.

FIG. 3 illustrates the parts of the system for applying shear to particles as described herein. In the side view (A), a device including a microfluidic layer and a structure containing reservoirs is shown. The structure can be irreversibly bonded to the fluidic layer. The pressure interface can be reversibly mated to the top of the reservoir structure to form a pressure seal. Tubing can be used to apply pressure to the reservoirs. A top-down view of the device only (no interface) is shown in (B). The corresponding reservoirs in the upper structure, the microfluidic channels and viewing area for image acquisition are all identified.

In another embodiment, a result obtained using the methods described herein is used to determine reactivity to a compound (e.g., a drug) and/or diagnose a disease state of an individual, for example, a patient. In a particular embodiment, determining reactivity to a compound includes reviewing or analyzing data relating to the reactivity of an individual's cell or cells to a compound. In one embodiment, the method of diagnosing a disease comprises reviewing or analyzing data relating to the presence and/or the concentration level of a target in a sample. In any case, a conclusion can be provided to a patient, a health care provider or a health care manager, the conclusion being based on the review or analysis of data regarding reactivity to a compound and/or a disease diagnosis. It is envisioned that in another embodiment the providing a conclusion to a patient, a health care provider or a health care manager includes transmission of the data over a network.

In practicing the methods of the present invention, many conventional techniques in molecular biology are optionally utilized. These techniques are well known and are explained in, for example, Ausubel et al. (Eds.) Current Protocols in Molecular Biology, Volumes I, II, and III, (1997), Ausubel et al. (Eds.), Short Protocols in Molecular Biology: A Compendium of Methods from Current Protocols in Molecular Biology, 5th Ed., John Wiley & Sons, Inc. (2002), Sambrook et al., Molecular Cloning: A Laboratory Manual, 3rd Ed., Cold Spring Harbor Laboratory Press (2000), and Innis et al. (Eds.) PCR Protocols: A Guide to Methods and Applications, Elsevier Science & Technology Books (1990), all of which are incorporated herein by reference.

Kits comprising reagents useful for performing described methods are also provided.

In some embodiments, a kit comprises microfluidic chip system as described herein and reagents for a compound (e.g., drug) screening platform. In other embodiments, a kit comprises a microfluidic chip system as described herein and reagents for an electroporation and/or electrophysiological platform.

The components of a kit can be retained by a housing. Instructions for using the kit to perform a described method can be provided with the housing, and can be provided in any fixed medium. The instructions may be located inside the housing or outside the housing, and may be printed on the interior or exterior of any surface forming the housing that renders the instructions legible. A kit may be in multiplex form for screening different compounds and/or electroporating different compounds (e.g., siRNA).

Figure 47:
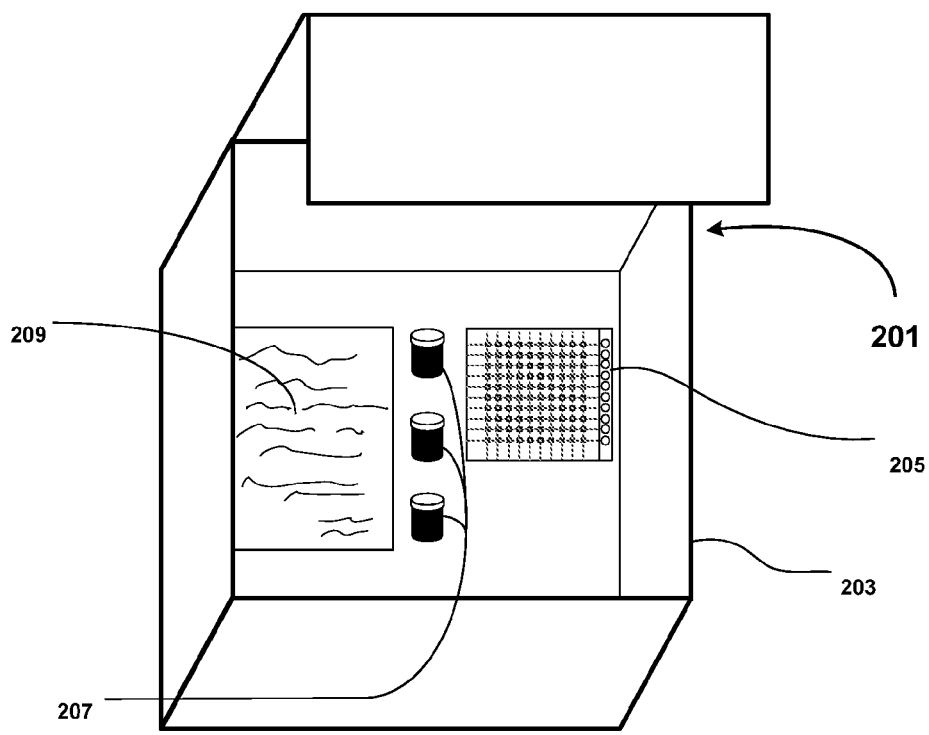
FIG. 47 is a block diagram showing a representative example of a kit.

As described herein and shown in FIG. 47, in certain embodiments a kit 903 can include a housing or container 902 for housing various components. As shown in FIG. 47 and described herein, the kit 903 can optionally include control interface and chip device 900, instructions 901 and reagents 905 (e.g., electroporation reagents and/or compounds). Other embodiments of the kit 903 are envisioned wherein the components include various additional features described herein.

In general, in another aspect, life sciences business systems and business methods are provided. A business method can include various embodiments of the system and methods described herein. In one embodiment a business method is provided wherein the system or methods described provides for intracellular delivery of substances and/or electrophysiology analysis of particles (e.g., cells or vesicles) in response to delivered substances. The results from the analysis can be used to identify, for example, therapeutic or diagnostic lead products useful, for example, for treatment of an individual. The business method can further include the step of collaboratively or independently, marketing the therapeutic or diagnostic products.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

REFERENCES CITED

Bonetta, L. (2005). "Flow cytometry smaller and better." Nature Methods 2(10): 785-+.

Cottingham, K. (2005). "Incredible shrinking flow cytometers." Analytical Chemistry 77(3): 73a-76a.

Ionescu-Zanetti, C., L. P. Wang, et al. (2005). "Alkaline hemolysis fragility is dependent on cell shape: Results from a morphology tracker." Cytometry Part A 65A(2): 116-123.

Long, X., W. L. Cleveland, et al. (2006). "Automatic detection of unstained viable cells in bright field images using a support vector machine with an improved training procedure." Computers in Biology and Medicine 36(4): 339-362.

Bennett, P. B. and H. R. E. Guthrie, Trends in ion channel drug discovery: advances in screening technologies. Journal of Biomolecular Screening, 2003.8(6): p. 660-667.

Byrom, M. et al. (2005) Visualizing siRNA in Mammalian Cells: Fluorescence Analysis of the RNAi Effect. Ambion TechNotes, 9, 3.

Chang, D. C. et al (1992) Guide to Electroporation and Electrofusion (Academic Press).

Chang, W. J. et al. (2003). Poly(dimethylsiloxane (PDMS) and Silicon Hybrid Biochip for Bacterial Culture, Biomedical Microdevices 5:4, 281-290.

Denyer, J., et al., HTS approaches to voltage-gated ion channel drug discovery. Drug Discovery Today, 1998.3(7): p. 323-332.

Entzeroth, M., Emerging trends in high-throughput screening. Current Opinion in Pharmacology, 2003. 3(5): p. 522-529.

Fertig, N., et al., Activity of single ion channel proteins detected with a planar microstructure. Applied Physics Letters, 2002. 81(25): p. 4865-4867.

Fertig, N., R. H. Blick, and J. C. Behrends, Whole Cell Patch Clamp Recording Performed on a Planar Glass Chip. Biophysical Journal, 2002. 82(6): p. 3056-3062.

Haas, K. et al. (2001) Single-cell electroporation for gene transfer in vivo Neuron 29:583-591.

Huang, Y, Rubinsky B. (2003) Flow-through micro-electroporation chip for high efficiency single-cell genetic manipulation, Sensors and Actuators A104, 3, 205-212.

Immke, D. and S. J. Korn, Ion-ion interactions at the selectivity filter—Evidence from K+-dependent modulation of tetraethylammonium efficacy in Kv2.1 potassium channels. Journal of General Physiology, 2000. 115(4): p. 509-518.

Ionescu-Zanetti, C., et al., Mammalian Electrophysiology on a Microfluidic Platform. PNAS, 2005. 102(26): p. 9112-9117.

Khine, M., Lau, A., Seo, J., and Lee, L. P. (2005) A Single-Cell Electroporation Array for Efficient Intracellular Delivery. IEEE EMBS Oahu, Hi. May 12-15, 2005.

Khine, M., Lau, A. D., Ionescu-Zanetti, C., Seo, J., Lee, L. P. (2005) A Single Cell Electroporation Chip. Royal Society of Chemistry Lab on a Chip, 5, 38-43.

Klemic, K. G., et al., Micromolded PDMS planar electrode allows patch clamp electrical recordings from cells. Biosensors and Bioelectronics, 2002. 17: p. 597-604.

Lee, E. et al. (2006) Microfluidic electroporation of robust 10 μm vesicles for manipulation of picoliter volumes. Bioelectrochemistry, 69, 117-125.

Lieberman, J. (2003) Interfering with disease: opportunities and road block stocks harnessing RNA interference, TRENDS in Molecular Medicine, 9, 9, 397-403.

Lin, Z., T. Kerle, and T. P. Russel, Structure Formation at the Interface of Liquid/Liquid Bilayer in Electric Field. Macromolecules, 2002. 35(10): p. 3971-3976.

Lundqvist, J. A., Sahlin, F., Aberg, M. A. I., Stromberg, A., Eriksson, P. S., Orwar, O. (1998). Altering the biochemical state of individual cultured cells and organelles with ultramicroelectrodes. Proc. Natl. Acad. Sci. U.S.A. 95: 10356-10360.

Moore, P. (2005) Ion channels and stem Cells, Nature, 438, 699-702.

Neumann, E., K. Toensing, S. Kakorin, P. Budde and J. Frey, Mechanism of Electroporative Dye Uptake by Mouse B Cells Biophys. J., 1998, 74, 98-108.

Nolkrantz, K. et al. (2001) Electroporation of Single Cells and Tissues with an Electrolyte-filled Capillary, Analytical Chemistry, 73, 4469-4477.

Nolkrantz, K. et al. (2002) Functional Screening of Intracellular Proteins in Single Cells and in Patterned Cell Arrays Using Electroporation. Analytical Chemistry, August 15, 74, 4300-4305.

Rae, J. L., Levis, R. A. (2002) Eur. J. Physiol., 443, 664-670.

Razvi, E. (2005). hERG Technology and Market Analysis, D&MD Publications.

Sackmann, B. and E. Neher, Single Channel Recording. 1983, New York: Plenum. (page 2 of specification)

Seo, J., et al., Integrated Multiple Patch-Clamp Array Chip via Lateral Cell Trapping Junctions. Applied Physics Letters, 2004. 84(11): p. 1973-1975.

Shaffer, C., Emerging Technologies for Ion Channels. Genetic Engineering News, 2005. 25(19): p. 15-17.

Shin, Y. S. et al. (2003). PDMS-based micro PCR chip with Parylene coating, J Micromech Microeng. 13, 768-774.

Southhan, A., I. F. James, and D. Cronk, Ion Channels—New Opportunities for an Established Target Class. Drug Discovery World, 2005: p. 18-23.

SuperArray Bioscience Corporation: Choosing the Right RNA Interference Method for Your Research (http://www.superarray.com/newsletter.rnai.html).

Tsong, T. Y. (1991) Electroporation of cell membranes. Biophysical Journal, 60: 297-306.

Valero, A. et al. (2005) Flow-through Microfluidic Chip for Cell Transfection by Electropermeabilization, Proceedings from MicroTAS, Boston, USA, October 9-13.

Wang, X. B. and M. Li, Automated electrophysiology: High throughput of art. Assay and Drug Development Technologies, 2003.1(5): p. 709-717.

Weaver, J. C. (1993) Electroporation: A general phenomenon for manipulating cells and tissues. J. Cell. Biochem 51:426-435.

Brown, D. C. and R. S. Larson (2001). "Improvements to parallel plate flow chambers to reduce reagent and cellular requirements." BMC Immunol 2: 9.

Lu, H., L. Y. Koo, et al. (2004). "Microfluidic shear devices for quantitative analysis of cell adhesion." Anal Chem 76(18): 5257-64.

What is claimed is:

1. A system comprising:
a microfluidic device having a plurality of trapping areas configured to trap a cell, wherein each trapping area includes a first channel and a plurality of second channels intersecting the first channel, wherein the first channel and the plurality of second channels are horizontal channels defined in part by a common surface, and wherein the first channel has a first height and the plurality of second channels have a second height, less than the first height, wherein at least one of the plurality of second channels is a horizontal channel configured to connect the first channel to a reservoir;
a well plate bonded to the microfluidic device, wherein the well plate defines a plurality of wells, wherein a respective grouping of the plurality of wells is associated with each of the trapping areas, and wherein each respective grouping includes a first well in fluid communication with the first channel and a plurality of second wells each in communication with a respective one of the plurality of second channels; and
an interface coupled to the well plate, wherein the interface is configured for individually addressing the first well and the plurality of second wells within at least one of the respective groupings, and wherein the interface is configured to apply pneumatic pressures to the first well and at least one of the second wells sufficient to move a fluid within the microfluidic device.

2. The system of claim 1, wherein the well plate comprises a microplate, the microfluidic device is integrated into the microplate and the microplate is selected from the group consisting of a 24-well, 96-well, 384-well, and a 1536-well microplate.

3. The system of claim 1, wherein the interface is coupled to at least a section of the well plate.

4. The system of claim 1, wherein the trapping areas comprise regions of the microfluidic device adapted for immobilizing a plurality of cells.

5. The system of claim 1, wherein the trapping areas comprise a region of the microfluidic device that is optically accessible.

6. The system of claim 1, wherein the trapping areas comprise a region of the microfluidic device that is optically accessible microscopically during patch clamp measurements.

7. The system of claim 1, further comprising an electrode array in electronic communication with the microfluidic device, wherein the electrode array comprises electrodes, and wherein at least one electrode extends into at least one of said wells when the well plate and interface are coupled.

8. The system of claim 7, wherein the electrodes are substantially cylindrical.

9. The system of claim 8, wherein the substantially cylindrical electrodes comprise an end, wherein a section cut out of the end of at least one electrode extends at least partially into the microfluidic device.

10. The system of claim 7, wherein the electrode array is adapted for electrophysiological analysis of plurality of cells.

11. The system of claim 10, wherein the electrophysiological analysis comprises recording selected from the group consisting of whole-cell recording and patch clamp recording.

12. The system of claim 7, wherein the interface is adapted to act as a shield for ambient electromagnetic waves.

13. The system of claim 7, wherein the interface is connectable to a patch clamp amplifier.

14. The system of claim 1, wherein the interface provides an aperture for optical access.

15. The system of claim 1, further comprising a current measurement system in electrical communication with the microfluidic device.

16. The system of claim 1, wherein said plurality of second channels intersect said first channel at respective lateral openings for immobilizing particles, wherein the distance between said lateral openings is substantially below 0.1 mm.

17. The system of claim 16, wherein the particles are selected from cells, vesicles and oocytes.

18. The system of claim 17, wherein the particles are cells.

19. The system of claim 18, wherein a plurality of the cells can be simultaneously observed microscopically.

20. The system of claim 19, further comprising one or more compound streams in fluid communication with the immobilized cells wherein the plurality of the cells is exposed to the same compound stream.

21. The system of claim 1, wherein said well plate comprises at least a portion of a wellplate having at least 96 wells, and wherein said interface is configured to provide at least 96 simultaneous pressure connections to individual ones of said 96 wells.

22. The system of claim 1, wherein said interface comprises a detachable interface configured to reversibly mate to said well plate.

23. The system of claim 1, wherein said interface comprises a gasket configured to at least partially cover said well plate and tubing configured to transport a gas into the at least one reservoir.

24. A system comprising:
   a microfluidic device comprising:
      a substrate;
      a main flow channel having a first height in said substrate adapted to hold cells in a fluidic medium;
      at least one lateral opening in a side of said main flow channel;
      at least one horizontal trapping channel in said substrate operatively connected to said lateral opening, wherein the horizontal trapping channel has a second height less than the first height, and wherein the main flow channel, the at least one lateral opening, and the at least one horizontal trapping channel are defined in part by a same surface; and
      at least two electrical connections on a same side of said substrate, one connected to said main flow channel and one connected to said trapping channel;
   wherein a particle in the main flow channel can be immobilized at said lateral opening by negative pressure in the trapping channel;
   at least one reservoir in fluid communication with the microfluidic device, wherein said at least one reservoir comprises at least a portion of a wellplate, wherein the wellplate is bonded to the microfluidic device; and
   a pneumatic interface coupled to the microfluidic device, wherein the interface is adapted for moving material within the microfluidic device at least in part by applying a pressure to an air-fluid interface in the reservoir, wherein said interface is configured to provide simultaneous pressure connections to individual wells of the wellplate.

25. The system of claim 24, wherein the particles are selected from the group consisting of cells, vesicles and oocytes.

26. The system of claim 25, wherein the particles are cells.

27. The system of claim 26, wherein a plurality of the cells can be simultaneously observed microscopically.

28. The system of claim 25, further comprising one or more compound streams in fluid communication with the immobilized cells wherein a plurality of the cells is exposed to the same compound stream.

29. The system of claim 26, wherein the detected characteristic of a cell is an ion-flux activity.

30. The system of claim 29, wherein the ion-flux activity is hERG activity.

31. The system of claim 24, wherein the main flow channel comprises an array of lateral openings, and the distance between lateral openings is substantially below 0.1 mm.

32. The system of claim 24, wherein said at least a portion of a wellplate has at least 96 wells, and wherein said interface is configured to provide at least 96 simultaneous pressure connections to individual ones of said 96 wells.

33. The system of claim 24, wherein said interface comprises a detachable interface configured to reversibly mate to said at least one reservoir.

34. The system of claim 24, wherein said interface comprises a gasket configured to at least partially cover said at least one reservoir and tubing configured to transport a gas into the at least one reservoir.

* * * * *